(12) United States Patent
Tomoda et al.

(10) Patent No.: US 8,519,128 B2
(45) Date of Patent: Aug. 27, 2013

(54) PYRIPYROPENE DERIVATIVES HAVING AN ACAT2-INHIBITING ACTIVITY

(75) Inventors: Hiroshi Tomoda, Tokyo (JP); Tohru Nagamitsu, Tokyo (JP); Satoshi Omura, Tokyo (JP)

(73) Assignee: The Kitasato Institute, Tokyo (JP)

( * ) Notice: Subject to any disclaimer, the term of this patent is extended or adjusted under 35 U.S.C. 154(b) by 41 days.

(21) Appl. No.: 12/810,545

(22) PCT Filed: Dec. 17, 2008

(86) PCT No.: PCT/JP2008/073501
§ 371 (c)(1),
(2), (4) Date: Feb. 17, 2011

(87) PCT Pub. No.: WO2009/081957
PCT Pub. Date: Jul. 2, 2009

(65) Prior Publication Data
US 2011/0184173 A1 Jul. 28, 2011

(30) Foreign Application Priority Data
Dec. 25, 2007 (JP) ................. 2007-331444

(51) Int. Cl.
C07D 493/04 (2006.01)
C07D 493/14 (2006.01)
C07D 401/14 (2006.01)

(52) U.S. Cl.
USPC ........ 544/310; 544/364; 544/405; 546/268.4; 546/283.1

(58) Field of Classification Search
None
See application file for complete search history.

(56) References Cited

U.S. PATENT DOCUMENTS
5,807,721 A * 9/1998 Omura et al. ................. 435/119

FOREIGN PATENT DOCUMENTS
JP 8259569 A 10/1996
JP 8269065 A 10/1996
WO 20060129714 A1 12/2006

OTHER PUBLICATIONS

Tomoda et al, caplus an 1995:664560.*
Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Obata et al., caplus an 2000:291483.*
Obata et al., Journal of Antibiotics, 2000, 53(4), 422-425.*
Patani et al., Chem. Rev., 1996, 96, 3147-3176.*
Tamio Teramoto, "Development of Novel Drugs for Treatment of Hyperlipidemia", in Lifestyle Related Diseases, 2001, p. 119-121, Nakayama Shoten Publisher.
Farese, Jr., "The Nine Lives of ACAT Inhibitors", Arterioscler. Thromb. Vasc. Biol., 2006, pp. 1684-1686, vol. 26.
Bell, III, et al., "Dietary Fat Induced Alterations in Atherosclerosis Are Abolished by ACAT2-Deficiency in ApoB100 Only, LDLr / Mice", Arterioscler. Thromb. Vasc. Biol., 2007, pp. 1396-1402, vol. 27.
Tomoda, et al., "Pyripyropenes, Novel Inhibitors of Acyl-CoA: Cholesterol Acyltransferase Produced by *Aspergillus fumigatus*", Journal of Antibiotics, Feb. 1994, pp. 148-153, vol. 47, No. 2.
Chang, et al., "Human Acyl-CoA: Cholesterol Acyltransferase (ACAT) and its Potential as a Target for Pharmaceutical Intervention Against Atherosclerosis", Acta Biochimica et Biophysica Sinica, 2006, pp. 151-156, vol. 38, No. 3.
Meuwese, et al., And then there were acyl coenzyme A:cholesterol acyl transferase inhibitors, Curr. Opin. Lipidol., vol. 17, pp. 426-431 (2006).
29M-pm12, The Pharmaceutical Society of Japan Nankai Yoshishu, Mar. 5, 2007, p. 6, vol. 127, No. 4.
030[H]-080, The Pharmaceutical Society of Japan Nenkai Yoshishu, Mar. 6, 2006, p. 21, vol. 126, No. 3.
Ohshiro et al., "Selectivity of Microbial Acyl-CoA: cholesterol Acyltransferase Inhibitors toward Isozymes", The Journal of Antibiotics, 2007, pp. 43-51, vol. 60, No. 1.
Cho et al., "Mass-production of human ACAT-1 and ACAt-2 to screen isoform-specific inhibitor: a different substrate specificity and inhibitory regulation", Biochemical and Biophysical Research Communications, 2003, pp. 864-872, vol. 309.
Lada et al., "Identification of ACAT1- and ACAT2—specific inhibitors using a novel, cell-based fluorescence assay: individual ACAT uniqueness", Journal of Lipid Research, 2004, pp. 378-386, vol. 45.
Obata et al., "Structure-activity Relationships Study of Pyripyropenes: reversal of Cancer Cell Multidrug Resistance", The Journal of Antibiotics, Apr. 2000, pp. 422-425, vol. 53, No. 4.
Obata et al., "Chemical Modification and Structure-activity Relationships of Pyripyropenes 3. Synthetic Conversion of Pyridine-pyrone Moiety", The Journal of Antibiotics, Mar. 1997, pp. 229-236, vol. 50., No. 3.
Obata et al., "Chemical Modification and Structure-activity Relationships of Pyripyropenes 2. 1,11-Cyclic Analogs", The Journal of Antibiotics, Nov. 1996, pp. 1149-1156, vol. 49, No. 11.
Obata et al., "Chemical Modification and Structure-activity Relationships of Pyripyropenes 1. Modification at the Four Hydroxyl Groups" The Journal of Antibiotics, Nov. 1996, pp. 1133-1148, vol. 49, No. 11.
Tomoda et al., "Pyripyropenes, Novel ACAT Inhibitors Produced by *Aspergillus fumigatus* IV. Structure Elucidation of Pyripyropenes M to R", The Journal of Antibiotics, Mar. 1996, pp. 292-298, vol. 49. No. 3.

(Continued)

Primary Examiner — Sun Jae Loewe
(74) Attorney, Agent, or Firm — The Webb Law Firm

(57) ABSTRACT

The present invention is a compound having the general formula (I), (II), or (III) or a pharmacologically acceptable salt, solvate, or hydrate thereof, and a pharmaceutical composition containing such a compound, or its pharmacologically acceptable ester, or other pharmacologically acceptable derivative thereof as an active ingredient. The compound has an excellent ACAT 2-inhibiting activity by a mechanism different from that of a statin drug and is useful as a therapeutic or prophylactic agent for obesity, adiposis, hyperlipidemia, hypercholesterolemia, disorder of lipid metabolism, and arteriosclerosis, as well as obesity-derived hyperlipidemia, hypercholesterolemia, disorder of lipid metabolism, arteriosclerosis, and hypertension.

2 Claims, No Drawings

(56) References Cited

OTHER PUBLICATIONS

Obata et al., "Structure-activity Relationships Study of Pyripyropenes Fungal Acyl-CoA: Cholesterol Acyltransferase Inhibitors", The Journal of Antibiotics, Jul. 1995, pp. 749-750, vol. 48, No. 7.

Obata et al., "Chemical Modification and Structure-activity Relationships of Pyripyropenes; Potent, Bioavailable Inhibitor of Acyl-CoA: Cholesterol O-Acyltransferase(ACAT)", Bioorganic & Medicinal Chemistry Letters, 1995, pp. 2683-2688, vol. 5, No. 22.

* cited by examiner

PYRIPYROPENE DERIVATIVES HAVING AN ACAT2-INHIBITING ACTIVITY

TECHNICAL FIELD

The present invention relates to pyripyropene A derivatives having an improved inhibitory activity against acyl-CoA cholesterol acyltransferase (hereinafter abbreviated as ACAT) isozyme 2 and more particularly it relates to such derivatives having substituted by 7-acyl or by 1,11-cyclic acetal and 7-acyl.

BACKGROUND ART

The number of patients with hyperlipemia or arteriosclerosis in Japan is said to be as much as thirty million including subjects having no rational symptoms. These disorders are associated with a high risk of highly mortal diseases such as heart infarction and cerebral apoplexy. Even at the present time when the Guidelines for Prevention of Atherosclerotic Cardiovascular Diseases have been revised by the Japan Atherosclerosis Society, death due to these diseases ranks high in the causes of death in Japan. Hyperlipemia and arteriosclerosis are significant health problems not only in Japan but also in Europe and the Americas. The drugs which are most widely used at present for prevention and treatment of arteriosclerosis are statin drugs which specifically inhibit hydroxy-3-methylglutaryl coenzyme A (hereinafter abbreviated as HMG-CoA) reductase. Three statin drugs rank in the top ten in worldwide sales of drugs. However, in point of fact, it has been found that these drugs exhibit an effect on prevention of onset in 30%-40% of patients and produce no suppression of cardiovascular diseases or the like in about a half of patients which received treatment with such a drug ("Lifestyle Related Disease" by Tamio Teramoto, Nakayama Shoten, 2001, p. 119).

The reasons why HMG-CoA reductase inhibitors which are currently used as agents for prevention and treatment of arteriosclerosis cannot sufficiently suppress cardiovascular diseases or the like are thought to relate to the fact that the mechanism of onset of arteriosclerosis is complicated, the onset mostly being caused by heredity, diabetes, drugs, and other various factors acting in combination. Therefore, diagnosis and treatment of this disease need to be performed in accordance with the pathology of each patient. Accordingly, there is an urgent desire for the development of a drug having a new mechanism of activities which can be expected to have an effect on suppression of onset of a disorder in the coronary artery or degeneration of a lesion in the coronary artery. However, development of a drug as a substitute for statin drugs has not progressed much until now.

ACAT is an enzyme which catalyzes the introduction of an acyl group into cholesterol, and it is considered to be a target of a drug which is expected to be developed for treatment of statin-resistant arteriosclerosis or tailor-made treatment in accordance with individual pathological conditions. This enzyme has attracted attention for years as an important target molecule of a drug for prevention and treatment of arteriosclerosis, and a number of synthetic ACAT inhibitors have been developed. However, these inhibitors have not yet put into clinical use due to side effects or insufficient effects (Meuwese et al., Curr. Opin. Lipidol., Vol. 17, pp. 426-431, 2006).

It has recently been revealed that ACAT exists in the form of two isozymes, ACAT 1 (expressed in many cells and tissues) and ACAT 2 (expressed specifically in the small intestine and liver), which have different in vivo functions from each other. Therefore, in the development of a new drug targeted at ACAT, the importance of specifying its selectivity is recognized (Chang et al., Acta. Biochim. Biophys. Sin., vol. 38, pp. 151-156, 2006).

It has been found that synthetic agents which were abandoned in the middle of their development have an activity which selectively inhibits ACAT 1 (such as Wu-V-23) or which inhibits both ACAT 1 and ACAT 2 (such as avasimibe and pactimibe) (Farese, Arterioscler. Thromb. Vasc. Biol., vol. 26, pp. 1684-1686, 2006).

Also taking the recently reported results of knockout mice (Bell et al., Arterioscler. Thromb. Vasc. Biol., vol. 27, pp. 1396-1402, 2007) into consideration, there is a strong expectation that a new drug will be developed from the family of selective ACAT 2 inhibitors.

It is reported that pyripyropene A which was already reported as an ACAT inhibitor (Tomoda et al., J. Antibiot. Vol. 47, pp. 148-153, 1994) selectively inhibits ACAT 2 isozyme (Lada et al., J. Lipid Res., vol. 45, pp. 378-386, 2004). However, up to the present time, there has been no research of development of a new drug with a selective ACAT 2 inhibitor as a main active agent.

DISCLOSURE OF THE INVENTION

The object of the present invention is to provide an agent which is effective for prevention and treatment of arteriosclerosis having a mechanism of activities which is different from that of a statin drug.

As a result of years of research, the present inventors found that novel pyripyropene A derivatives have a selective and high inhibitory activity against ACAT2, which has drew attention as a target of a drug for prevention and treatment of arteriosclerosis, and they thereby accomplished the present invention. Thus, the present invention is a compound having the following general formula (I):

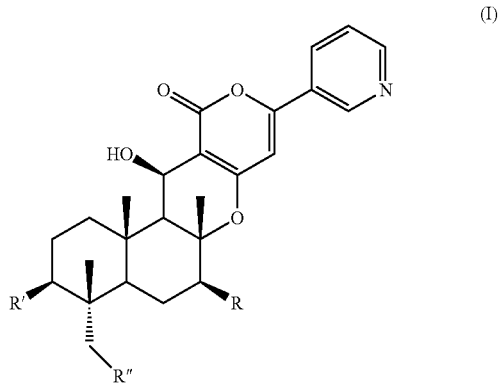

wherein R, R', and R" each represents a lower acyloxy, substituted lower acyloxy, aromatic acyloxy, substituted arylacyloxy, arylacyloxy, heteroarylacyloxy, substituted heteroarylacyloxy, lower alkoxy, substituted lower alkoxy, carbamoyl, lower alkylaminoacyloxy, substituted alkylaminoacyloxy, lower alkylsulfonyl, substituted lower alkylsulfonyl, aromatic sulfonyl, lower alkyl, substituted lower alkyl, aromatic sulfanyl, substituted aromatic sulfanyl, tetrazoyl, substituted tetrazoyl, triazoyl, substituted triazoyl, azide, amino, cyano, substituted amino, or halo group, and a pharmaceutically acceptable salt, solvate, or hydrate thereof.

Also, the present invention is a compound having the following formula (I):

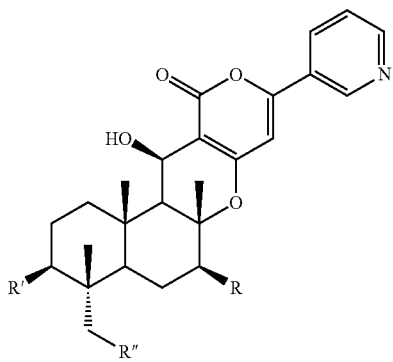

(I)

wherein R, R', and R" may the same or different from each other and each represents acetoxy, 2-aminoacetoxy, 2-hydroxyacetoxy, 2-acetamide, n-propionyloxy, i-propionyloxy, n-butyryloxy, i-butyryloxy, s-butyryloxy, t-butyryloxy, n-valeryloxy, cyclopropanecarboxyl, cyclobutanecarboxyl, cyclohexanecarboxyl, 1-adamantanecarboxyl, benzoyloxy, 2-methoxybenzoyloxy, 3-methoxybenzoyloxy, 4-methoxybenzoyloxy, 2-iodobenzoyloxy, 3-iodobenzoyloxy, 4-iodobenzoyloxy, 2-methylbenzoyloxy, 3-methylbenzoyloxy, 4-methylbenzoyloxy, 2-chlorobenzoyloxy, 3-chlorobenzoyloxy, 4-chlorobenzoyloxy, 2-cyanobenzoyloxy, 3-cyanobenzoyloxy, 4-cyanobenzoyloxy, 2-fluorobenzoyloxy, 3-fluorobenzoyloxy, 4-fluorobenzoyloxy, 3-vinylbenzoyloxy, 4-vinylbenzoyloxy, 2-bromobenzoyloxy, 3-bromobenzoyloxy, 4-bromobenzoyloxy, 3-methylthiobenzoyloxy, 4-methylthiobenzoyloxy, 4-ethylbenzoyloxy, 4-nitrobenzoyloxy, 4-azidebenzoyloxy, 4-aminobenzoyloxy, 4-(O-triisopropylsilyloxy)benzoyloxy, 4-hydroxybenzoyloxy, 3-fluoro-4-cyanobenzoyloxy, 3,5-diiodo-4-(O-triisopropylsilyloxy)benzoyloxy, 3,5-diiodo-4-hydroxybenzoyloxy, 4-biphenylcarboxyl, benzo[b]thiophene-2-carboxyl, 1-naphthylcarboxyl, 2-naphthylcarboxyl, 2,2-difluorobenzo[d][1,3]dioxol-5-carboxyl, phenylcarboxyl, 4-chlorophenycarboxyl, methoxymethyloxy, ethoxymethyl, methoxyethoxymethyloxy, benzyloxymethyloxy, methanesulfonyl, p-toluenesulfonyl, methoxy, ethoxy, benzyloxy, phenyloxy, phenylcarbonate, 4-chlorophenylcarbonate, 4-cyanophenylcarbonate, fluoro, chloro, bromo, iodo, methylsulfanyl, ethylsulfanyl, phenylsulfanyl, 1-p-methoxyphenyl-1,1-tetrazoylylsulfanyl, 1-phenyl-1H-tetrazoyl, or 1-methyltetrazoyl, and a pharmaceutically acceptable salt, solvate, or hydrate thereof.

Also, the present invention is a compound having the following general formula (II):

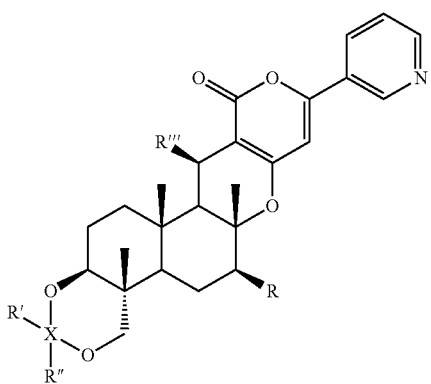

(II)

wherein R and R''' each represents a lower acyloxy, substituted lower acyloxy, aromatic acyloxy, substituted arylacyloxy, arylacyloxy, heteroarylacyloxy, substituted heteroarylacyloxy, lower alkoxyacyloxy, substituted lower alkoxyacyloxy, carbamoyl, lower alkylaminoacyloxy, substituted alkylaminoacyloxy, lower alkylsulfonyl, substituted lower alkylsulfonyl, aromatic sulfonyl, lower alkyl, substituted lower alkyl, aromatic sulfanyl, substituted aromatic sulfanyl, substituted tetrazoyl, triazoyl, substituted triazoyl, azide, amino, to cyano, substituted amino, or halo group, R' and R" may be the same or different from each other and each represents a hydrogen atom, a straight- or branched-chain alkyl group, a cyclic alkyl group, or an aromatic ring, and X represents a carbon or a silicon atom, and a pharmaceutically acceptable salt, solvate, or hydrate thereof.

Also, the present invention is a compound having the following formula (II):

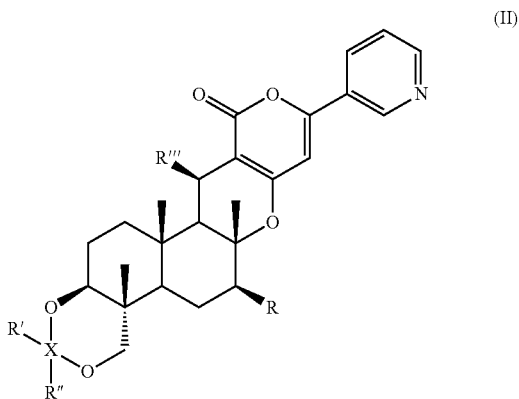

(II)

wherein R and R''' each represents acetoxy, 2-aminoacetoxy, 2-hydroxyacetoxy, 2-acetamide, n-propionyloxy, i-propionyloxy, n-butyryloxy, i-butyryloxy, s-butyryloxy, t-butyryloxy, n-valeryloxy, cyclopropanecarboxyl, cyclobutanecarboxyl, cyclohexanecarboxyl, 1-adamantanecarboxyl, benzoyloxy, 2-methoxybenzoyloxy, 3-methoxybenzoyloxy, 4-methoxybenzoyloxy, 2-iodobenzoyloxy, 3-iodobenzoyloxy, 4-iodobenzoyloxy, 2-methylbenzoyloxy, 3-methylbenzoyloxy, 4-methylbenzoyloxy, 2-chlorobenzoyloxy, 3-chlorobenzoyloxy, 4-chlorobenzoyloxy, 2-cyanobenzoyloxy, 3-cyanobenzoyloxy, 4-cyanobenzoyloxy, 2-fluorobenzoyloxy, 3-fluorobenzoyloxy, 4-fluorobenzoyloxy, 3-vinylbenzoyloxy, 4-vinylbenzoyloxy, 2-bromobenzoyloxy, 3-bromobenzoyloxy, 4-bromobenzoyloxy, 3-methylthiobenzoyloxy, 4-methylthiobenzoyloxy, 4-ethylbenzoyloxy, 4-nitrobenzoyloxy, 4-azidebenzoyloxy, 4-aminobenzoyloxy, 4-(O-triisopropylsilyloxy)benzoyloxy, 4-hydroxybenzoyloxy, 3-fluoro-4-cyanobenzoyloxy, 3,5-diiodo-4-(O-triisopropylsilyloxy)benzoyloxy, 3,5-diiodo-4-hydroxybenzoyloxy, 4-biphenylcarboxyl, benzo[b]thiophene-2-carboxyl, 1-naphthylcarboxyl, 2-naphthylcarboxyl, 2,2-difluorobenzo[d][1,3]dioxol-5-carboxyl, phenylcarboxyl, 4-chlorophenycarboxyl, methoxymethyloxy, ethoxymethyl, methoxyethoxymethyloxy, benzyloxymethyloxy, methanesulfonyl, p-toluenesulfonyl, methoxy, ethoxy, benzyloxy, phenyloxy, phenylcarbonate, 4-chlorophenylcarbonate, 4-cyanophenylcarbonate, fluoro, chloro, bromo, iodo, methylsulfanyl, ethylsulfanyl, phenylsulfanyl, 1-p-methoxyphenyl-1H-tetrazoylylsulfanyl, 1-phenyl-1H-tetrazoyl, or 1-methyltetrazoyl, and a pharmaceutically acceptable salt, solvate, or hydrate thereof.

Also, the present invention is a compound having the following general formula (III):

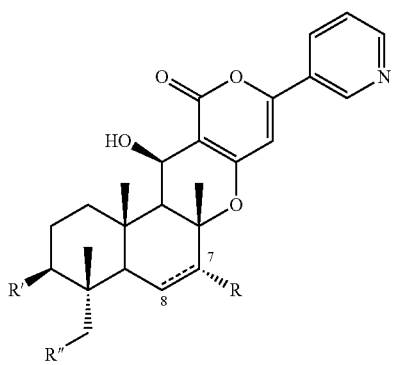

wherein R, R', and R" each represents a lower acyloxy, substituted lower acyloxy, aromatic acyloxy, substituted arylacyloxy, arylacyloxy, heteroarylacyloxy, substituted heteroarylacyloxy, lower alkoxyacyloxy, substituted lower alkoxyacyloxy, carbamoyl, lower alkylaminoacyloxy, substituted alkylaminoacyloxy, lower alkylsulfonyl, substituted lower alkylsulfonyl, aromatic sulfonyl, lower alkyl, substituted lower alkyl, aromatic sulfanyl, substituted aromatic sulfanyl, triazoyl, substituted triazoyl, azide, amino, cyano, substituted amino, or halo group, and a pharmaceutically acceptable salt, solvate, or hydrate thereof.

Also, the present invention is a compound having the following formula (III):

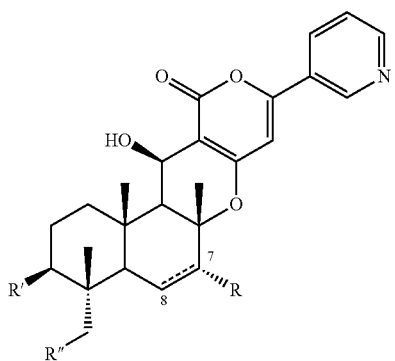

wherein R and the hydrogen atom at the 8 position may not exist such that the compound has a double bond between the 7 and 8 positions, and R, R', and R" may the same or different from each other and each represents acetoxy, 2-aminoacetoxy, 2-hydroxyacetoxy, 2-acetamide, n-propionyloxy, i-propionyloxy, n-butyryloxy, i-butyryloxy, s-butyryloxy, t-butyryloxy, n-valeryloxy, cyclopropanecarboxyl, cyclobutanecarboxyl, cyclohexanecarboxyl, 1-adamantanecarboxyl, benzoyloxy, 2-methoxybenzoyloxy, 3-methoxybenzoyloxy, 4-methoxybenzoyloxy, 2-iodobenzoyloxy, 3-iodobenzoyloxy, 4-iodobenzoyloxy, 2-methylbenzoyloxy, 3-methylbenzoyloxy, 4-methylbenzoyloxy, 2-chlorobenzoyloxy, 3-chlorobenzoyloxy, 4-chlorobenzoyloxy, 2-cyanobenzoyloxy, 3-cyanobenzoyloxy, 4-cyanobenzoyloxy, 2-fluorobenzoyloxy, 3-fluorobenzoyloxy, 4-fluorobenzoyloxy, 3-vinylbenzoyloxy, 4-vinylbenzoyloxy, 2-bromobenzoyloxy, 3-bromobenzoyloxy, 4-bromobenzoyloxy, 3-methylthiobenzoyloxy, 4-methylthiobenzoyloxy, 4-ethylbenzoyloxy, 4-nitrobenzoyloxy, 4-azidebenzoyloxy, 4-aminobenzoyloxy, 4-(O-triisopropylsilyloxy)benzoyloxy, 4-hydroxybenzoyloxy, 3-fluoro-4-cyanobenzoyloxy, 3,5-diiodo-4-(O-triisopropylsilyloxy)benzoyloxy, 3,5-diiodo-4-hydroxybenzoyloxy, 4-biphenylcarboxyl, benzo[b]thiophene-2-carboxyl, 1-naphthylcarboxyl, 2-naphthylcarboxyl, 2,2-difluorobenzo[d][1,3]dioxol-5-carboxyl, phenylcarboxyl, 4-chlorophenycarboxyl, methoxymethyloxy, ethoxymethyl, methoxyethoxymethyloxy, benzyloxymethyloxy, methanesulfonyl, p-toluenesulfonyl, methoxy, ethoxy, benzyloxy, phenyloxy, phenylcarbonate, 4-s chlorophenylcarbonate, 4-cyanophenylcarbonate, fluoro, chloro, bromo, iodo, methylsulfanyl, ethylsulfanyl, phenylsulfanyl, 1-p-methoxyphenyl-1H-tetrazoylylsulfanyl, 1-phenyl-1H-tetrazoyl, or 1-methyltetrazoyl, and a pharmaceutically acceptable salt, solvate, or hydrate thereof.

Also, the present invention is an ACAT 2 inhibitor comprising as an active ingredient a compound selected from the compound groups recited above or a pharmaceutically acceptable salt, solvate, or hydrate thereof. Also, the present invention is a pharmaceutical composition for ACAT 2 inhibition comprising as an active ingredient a compound selected from the compound groups recited above or a pharmaceutically acceptable salt, solvate, or hydrate thereof.

DEFINITIONS

The terms "lower alkyl", "lower alkoxy", and "lower acyloxyl" used herein as a group or a part of a group indicate a straight- or branched-chain alkyl, alkoxy, and acyloxy group, respectively, having 1 to 6 and preferably 1 to 4 carbon atoms. Examples of a "lower alkyl" as a group or a part of a group include methyl, ethyl, n-propyl, isopropyl, n-butyl, i-butyl, s-butyl, t-butyl, n-pentyl, neopentyl, i-pentyl, t-pentyl, n-hexyl, i-hexyl, and the like. Examples of a "lower alkoxy" as a group or a part of group include methoxy, ethoxy, n-propoxy, i-propoxy, n-butoxy, s-butoxy, t-butoxy, n-pentyloxy, neopentyloxy, i-pentyloxy, t-pentykoxy, n-hexyloxy, i-hexyloxy, and the like. Examples of a "lower acyloxy" as a group or a part of group include aceoxy, n-propionyloxy, i-propionyloxy, n-butyryloxy, i-butyryloxy, s-butyryloxy, t-butyryloxy, n-valeryloxy, neovaleryloxy, i-valeryloxy, t-valeryloxy, n-caproyloxy, i-caproyloxy, and the like.

The term "halogen atom" used herein indicates a fluorine, chlorine, bromine, or iodine atom. The term "cycloalkyl" used herein includes cyclopropyl, cyclobutyl, cyclopentyl, cyclohexyl, and the like. The term "aryl" used herein as a group or a part of group indicates phenyl and naphthyl.

The term "heteroaryl" used herein as a group or a part of a group indicates a 5- or 6-membered aromatic heterocyclic or heteropolycyclic compound having one or more hetero atoms which may be the same or different and are selected from the group consisting of nitrogen, oxygen, and sulfur. Preferably, it includes furan, pyrrole, imidazole, thiazole, triazole, tetrazole, thiadiazole, pyridine, pyridazine, pyrimidine, indole, thionaphthene, and the like.

A pharmaceutical composition according to the present invention can be formulated by any method known to those skilled in the art. For example, a compound according to the present invention may be combined with a pharmaceutically acceptable carrier or medium which is appropriately selected from sterilized water, physiological saline, vegetable oils, emulsifiers, suspending agents, surfactants, stabilizers, flavors, excipients, vehicles, preservatives, and binders, and mixed in unit dosage form which is required for generally accepted pharmaceutical practice.

For oral administration, a compound according to the present invention or its salt can be formulated in the form of a tablet, pill, sugar-coated tablet, capsule, liquid, gel, syrup, slurry, suspension or the like by mixing it with a pharmaceutically acceptable carrier which is well known in the art. Any carrier which has heretofore been known in the art can be used. Examples of such a carrier include excipients such as lactose, sucrose, sodium chloride, glucose, urea, starch, calcium carbonate, kaolin, crystalline cellulose, and silica; binders such as water, ethanol, propanol, simple syrup, glucose solution, starch solution, gelatine solution, carboxymethylcellulose, shellac, methylcellulose, potassium phosphate, and polyvinylpyrrolidone; disintegrating agents such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, and lactose; disintegration suppressors such as sucrose, stearin cacao butter, and hydrogenated oils; absorbefacients such as quaternary ammonium salts and sodium lauryl sulfate; humectants such as glycerin and starch; adsorbents such as starch, lactose, kaolin, bentonite, and colloidal silica; lubricants such as purified talc, stearic acid salts, boric acid powder, and polyethylene glycol; and the like. In addition, tablets may be in the form of tablets having a conventional coating such as sugar-coated tablets, gelatine-encapsulated tablets, enteric coated tablets, film-coated tablets, or multi-coated tablets with two or more coating layers.

For parenteral administration, a compound according to the present invention or its salt can be formulated in accordance with a conventional formulating practice using a pharmaceutically acceptable vehicle which is well known in the art. Examples of a water-soluble vehicle for use in injections include physiological saline and isotonic solutions containing glucose or other adjuvant such as D-sorbitol, D-mannose, D-mannitol, or sodium chloride. It may be used along with a suitable solubilizer, for example, an alcohol such as ethanol, a polyhydric alcohol such as propylene glycol or polyethylene glycol, or a nonionic surfactant such as polysolvate 80™ or HCO-50. An oily vehicle includes sesame oil and soybean oil, and it may be used along with a solubilizer such as benzyl benzoate or benzyl alcohol. In addition, a buffer such as a phosphate buffer solution or a sodium acetate buffer solution, a soothing agent such as procaine hydrochloride, a stabilizer such as benzyl alcohol or phenol, and an antioxidant may be added. An injection which is prepared is usually packaged in appropriate ampoules.

An appropriate route of administration of a pharmaceutical composition according to the present invention includes, but is not limited to, oral, intrarectal, mucosal, or intraintestinal administration and intramuscular, subcutaneous, intramedullary, intrathecal, direct intraventricular, intravenous, intravitreous, intraperitoneal, intranasal, or intraocular injection. The route of administration can be appropriately selected depending on the patient's age, condition, and other medicines which are also administered to the patient. A dose of a pharmaceutical composition according to the present invention in each administration can be selected in the range of from 0.001 mg to 10 mg per kg of body weight. Alternatively, a dose in each administration can be selected in the range of from 0.1 mg to 100 mg. A dose is not necessarily limited to these ranges. The dose and dosage regimen can be suitably selected by the accompanying medical practitioner in view of the body weight, age, and condition of a patient and other medicines which are also administered to the patient.

Effect of the Invention

A pyripyropene derivative represented by the formula (I), (II), or (III) and its pharmacologically acceptable salt has improved ACAT 2 inhibitory activity. A pharmaceutical composition comprising as an active ingredient a compound according to the present invention, its pharmacologically acceptable salt, its pharmacologically acceptable ester, or other pharmacologically acceptable derivative thereof is useful as a prophylactic or therapeutic agent for arteriosclerotic diseases.

BEST MODE FOR CARRYING OUT THE INVENTION

The present invention will be described with respect to preparation and examples, but the present invention is not restricted by these examples.

A compound of Formula (I) according to the present in which R' and R" are acetoxy and R is an acyloxy group can be prepared in accordance with the following scheme.

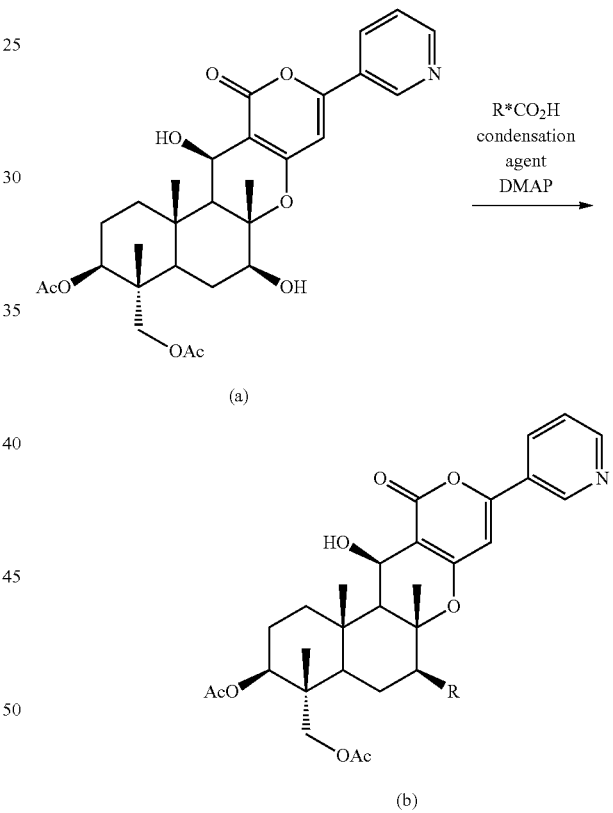

In the above scheme, R*CO$_2$H is the carboxylic acid corresponding to the acyloxy group (R=R*CO$_2$) defined by Formula (I).

Compound (a) in the above scheme can be prepared in a conventional manner (see, for example, Obata et al., J. Antibiot. vol. 49, pp. 1133-1148, 1996).

Conversion of compound (a) to compound (b) can be carried out in the following manner. Compound (a) is reacted for from 30 minutes to 2 days at room temperature in a solvent such as dichloromethane, dimethylformamide, tetrahydrofuran, acetonitrile or a mixture of these in the presence of 1 equivalent or excess of the corresponding carboxylic acid R*CO₂H, 1 equivalent or excess of a condensation agent (preferably 1-ethyl-3-(3-dimethylaminopropyl)carbodiimide hydrochloride or dicyclohexylcarbodiimide), and 0.5 equivalents or excess of an organic base (preferably N,N-dimethylaminopyridine). The reaction mixture is post-treated in a conventional manner to give compound (b).

A compound of Formula (II) according to the present in which X is carbon and R is an acyloxy group can be prepared in accordance with the following scheme.

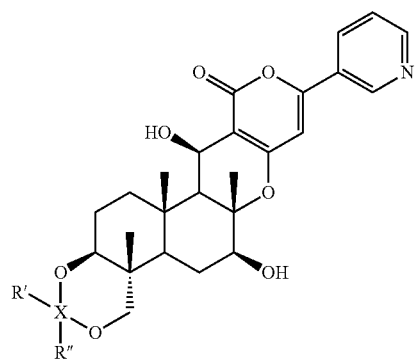

(c)

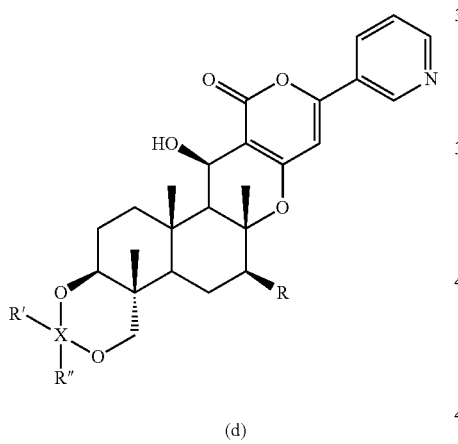

(d)

In the above scheme, R*CO₂H is the carboxylic acid corresponding to the acyloxy group (R=R*CO₂) defined by Formula (II), and X, R', and R" are as defined in Formula (II).

Compound (c) in the above scheme can be prepared in a conventional manner (see, for example, Obata et al., J. Antibiot. vol. 49, pp. 1149-1156, 1996).

Conversion of compound (c) to compound (d) can be carried out in the following manner. Compound (c) is reacted for from 30 minutes to 2 days at room temperature in a solvent such as dichloromethane, dimethylformamide, tetrahydrofuran, acetonitrile or a mixture of these in the presence of 1 equivalent or excess of the corresponding carboxylic acid R*CO₂H, 1 equivalent or excess of a condensation agent (preferably 1-ethyl-3-(3-dimethylaminopropyl)carbodiimide hydrochloride or dicyclohexylcarbodiimide), and 0.5 equivalents or excess of an organic base (preferably N,N-dimethylaminopyridine). The reaction mixture is post-treated in a conventional manner to give compound (d).

Example 1

Preparation of
7-o-methoxybenzoyl-7-deacetylpyripyropene A
(PRD 001)

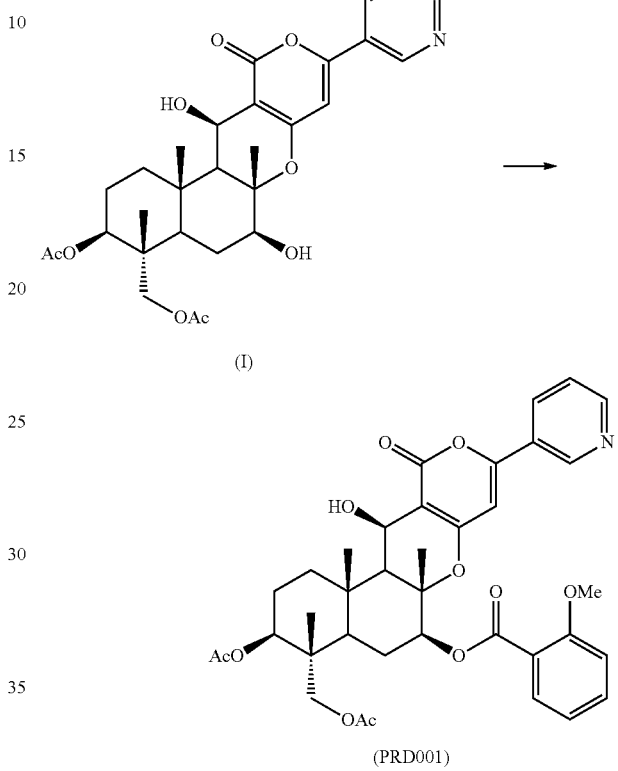

In an argon atmosphere, DCC (17.2 mg, 83.2 μmol), o-anisic acid (9.4 mg, 62.0 μmol), and DMAP (3.4 mg, 27.0 μmol) were added to a solution of compound I (15 mg, 27.7 μmol) in CH₂Cl₂ (0.5 mL) and stirred for 2 hours at room temperature. The reaction mixture was diluted with EtOAc, and undissolved matter was removed by filtration. The filtrate was washed with 1N HCl and water and dried over anhydrous sodium sulfate. The solution was filtered, and the filtrate was concentrated at a reduced pressure. The resulting residue was purified by neutral flash silica gel column chromatography (1×10, MeOH in CH₂Cl₂ 0.5-1.5%) to give PRD 001 (17.1 mg, 91%) as a white solid.

$[\alpha]^{24}_D$ +42.88 (c 1.0, CHCl₃);
¹H NMR (CDCl₃, 300 MHz) δ 8.98 (d, 1H, H-2", J=2.1 Hz), 8.67 (dd, 1H, H-6", J=1.2, 4.5 Hz), 8.09-8.05 (m, 1H, H-4"), 7.93 (dd, 1H, H—Ar, J=1.8, 7.8 Hz), 7.41-7.27 (m, 1H, H-5"), 7.06-7.01 (m, 2H, H—Ar), 6.45 (s, 1H, H-5'), 5.28 (dd, 1H, H-7, J=4.8, 11.1 Hz), 5.03 (d, 1H, H-13, J=4.2 Hz), 4.81 (dd, 1H, H-1, J=5.1, 11.1 Hz), 3.94 (s, 3H, OMe), 3.90 (d, 1H, H-11a, J=11.7 Hz), 3.64 (d, 1H, H-11b, J=11.7 Hz), 2.92 (br s, 1H, OH-13), 2.22-1.46 (m, 8H, H-2, 3, 5, 8, 9), 2.12 (s, 3H, Ac), 2.05 (s, 3H, Ac), 1.84 (s, 3H, Me), 1.49 (s, 3H, Me), 0.91 (s, 3H, Me).
¹³C NMR (CDCl₃, 150 MHz) δ 170.95, 170.50, 164.89, 163.98, 162.29, 159.60, 157.24, 151.39, 146.71, 134.03, 133.02, 132.03, 123.67, 120.15, 119.51, 112.10, 102.91, 99.51, 83.54, 78.06, 73.47, 64.87, 60.30, 55.89, 54.69, 45.46, 40.40, 37.87, 36.12, 25.84, 22.70, 21.11, 20.88, 17.52, 17.44, 15.65, 13.16.

FAB-LRMS m/z 676 (MH+); FAB-HRMS (CHCl3) calcd. for C37H42NO11 676.2758 (MH+). found 676.2756 (MH+).

Example 2

Preparation of
7-m-methoxybenzoyl-7-deacetylpyripyropene A
(PRD 002)

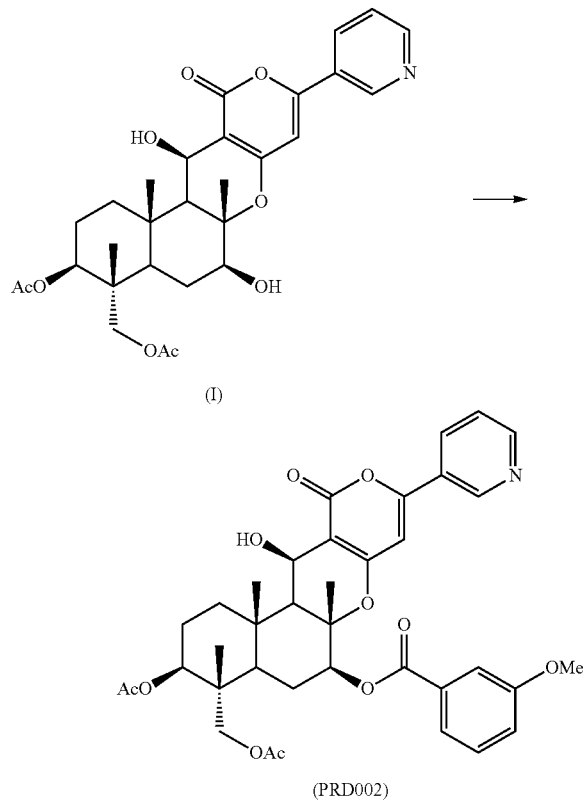

(PRD002)

In an argon atmosphere, EDCI (8.0 mg, 41.6 μmol), m-anisic acid (4.7 mg, 30.5 μmol), and DMAP (1.7 mg, 13.9 μmol) were added to a solution of compound I (15 mg, 27.7 μmol) in CH2Cl2 (0.5 mL) and stirred for 5 hours at room temperature. The reaction mixture was diluted with EtOAc, and the organic layer was washed with 1N HCl and water and dried over anhydrous sodium sulfate. The solution was filtered, and the filtrate was concentrated at a reduced pressure. The resulting residue was purified by neutral flash silica gel column chromatography (1.5×7, MeOH in CH2Cl2 0.5-1.5%) to give PRD 002 (17.5 mg, 94%) as a white solid.

$[\alpha]^{24}_D$ +50.47 (c 1.0, CHCl3);
$^1$H NMR (CDCl3, 300 MHz) δ 8.97 (d, 1H, H-2", J=1.8 Hz), 8.66 (dd, 1H, H-6", J=1.5, 4.8 Hz), 8.08-8.04 (m, 1H, H-4"), 7.72-7.69 (m, 1H, H—Ar), 7.63 (dd, 1H, H—Ar, J=1.5, 2.4 Hz), 7.43-7.35 (m, 2H, H-5", Ar), 7.17-7.13 (m, 1H, H—Ar), 6.43 (s, 1H, H-5'), 5.26 (dd, 1H, H-7, J=5.1, 11.1 Hz), 5.03 (d, 1H, H-13, J=4.2 Hz), 4.82 (dd, 1H, H-1, J=5.1, 11.1 Hz), 3.87 (s, 3H, OMe), 3.75 (d, 1H, H-11a, J=12.0 Hz), 3.54 (d, 1H, H-11b, J=12.0 Hz), 3.01 (br s, 1H, OH-13), 2.22-1.46 (m, 8H, H-2, 3, 5, 8, 9), 2.13 (s, 3H, Ac), 2.05 (s, 3H, Ac), 1.85 (s, 3H, Me), 1.50 (s, 3H, Me), 0.91 (s, 3H, Me).
$^{13}$C NMR (CDCl3, 150 MHz) δ 170.92, 170.51, 165.29, 163.93, 162.18, 159.64, 157.27, 151.38, 146.67, 133.03, 131.42, 123.75, 122.02, 119.47, 114.49, 102.97, 99.44, 83.41, 78.35, 73.52, 64.87, 60.24, 55.47, 54.75, 45.44, 40.39, 37.90, 37.15, 36.15, 29.75, 25.30, 22.70, 21.11, 20.85, 17.50, 16.54, 13.20.
FAB-LRMS m/z 676 (MH+); FAB-HRMS (CHCl3) calcd. for C37H42NO11 676.2756 (MH+). found 676.2756 (MH+).

Example 3

Preparation of
7-p-methoxybenzoyl-7-deacetylpyripyropene A
(PRD 003)

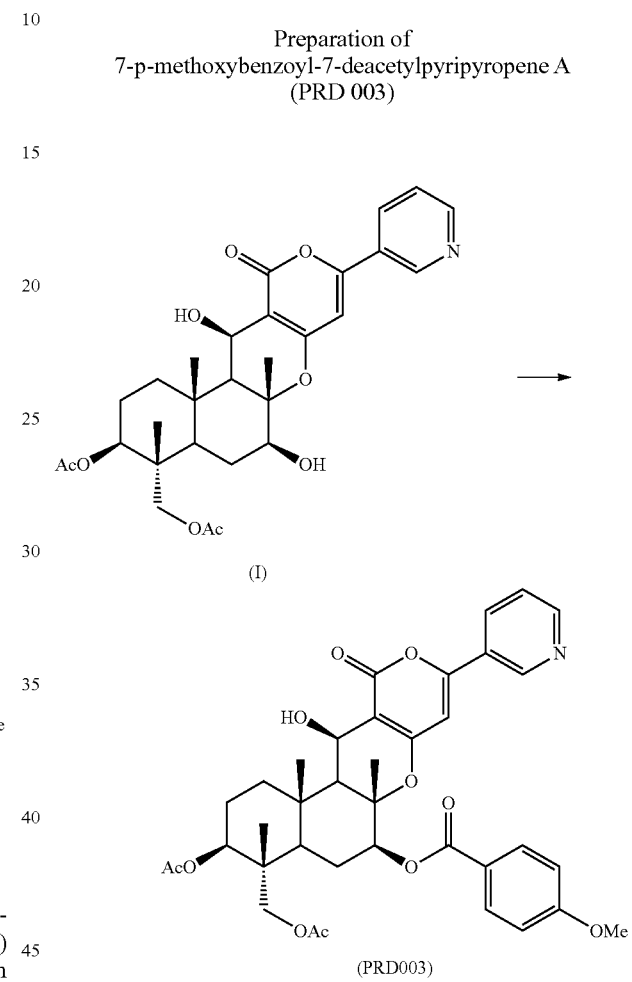

(PRD003)

In the same manner as in Example 2, PRD 003 (18.7 mg, 100%) was obtained as a white solid from compound I (15 mg, 27.7 μmol).

$[\alpha]^{24}_D$ +73.64 (c 1.0, CHCl3);
$^1$H NMR (CDCl3, 300 MHz) δ 8.96 (d, 1H, H-2", J=1.7 Hz), 8.66 (dd, 1H, H-6", J=1.8, 5.1 Hz), 8.09-8.04 (m, 3H, H-4", Ar), 7.40-7.35 (m, 1H, H-5"), 6.97 (dd, 2H, H—Ar, J=4.8 Hz), 6.43 (s, 1H, H-5'), 5.24 (dd, 1H, H-7, J=5.1, 11.1 Hz), 5.03 (d, 1H, H-13, J=3.9 Hz), 4.81 (dd, 1H, H-1, J=5.1, 11.4 Hz), 3.89 (s, 3H, OMe), 3.85 (d, 1H, H-11a, J=12.0 Hz), 3.68 (d, 1H, H-11b, J=12.0 Hz), 3.03 (br s, 1H, OH-13), 2.22-1.45 (m, 8H, H-2, 3, 5, 8, 9), 2.13 (s, 3H, Ac), 2.05 (s, 3H, Ac), 1.85 (s, 3H, Me), 1.49 (s, 3H, Me), 0.91 (s, 3H, Me).
$^{13}$C NMR (CDCl3, 150 MHz) δ 170.94, 170.51, 165.15, 163.95, 163.61, 162.23, 157.22, 151.38, 146.68, 133.03, 131.76, 123.65, 122.48, 115.82, 113.73, 102.95, 99.49, 83.49, 77.86, 73.54, 64.87, 60.27, 55.48, 54.76, 45.44, 41.39, 40.39, 37.90, 36.16, 25.39, 22.71, 21.12, 20.85, 17.50, 16.54, 13.19.

FAB-LRMS m/z 676 (MH+); FAB-HRMS (CHCl3) calcd. for C37H42NO11 676.2756 (MH+). found 676.2753 (MH+).

Example 4

Preparation of 7-o-iodobenzoyl-7-deacetylpyripyropene A (PRD 004)

Example 5

Preparation of 7-m-iodobenzoyl-7-deacetylpyripyropene A (PRD 005)

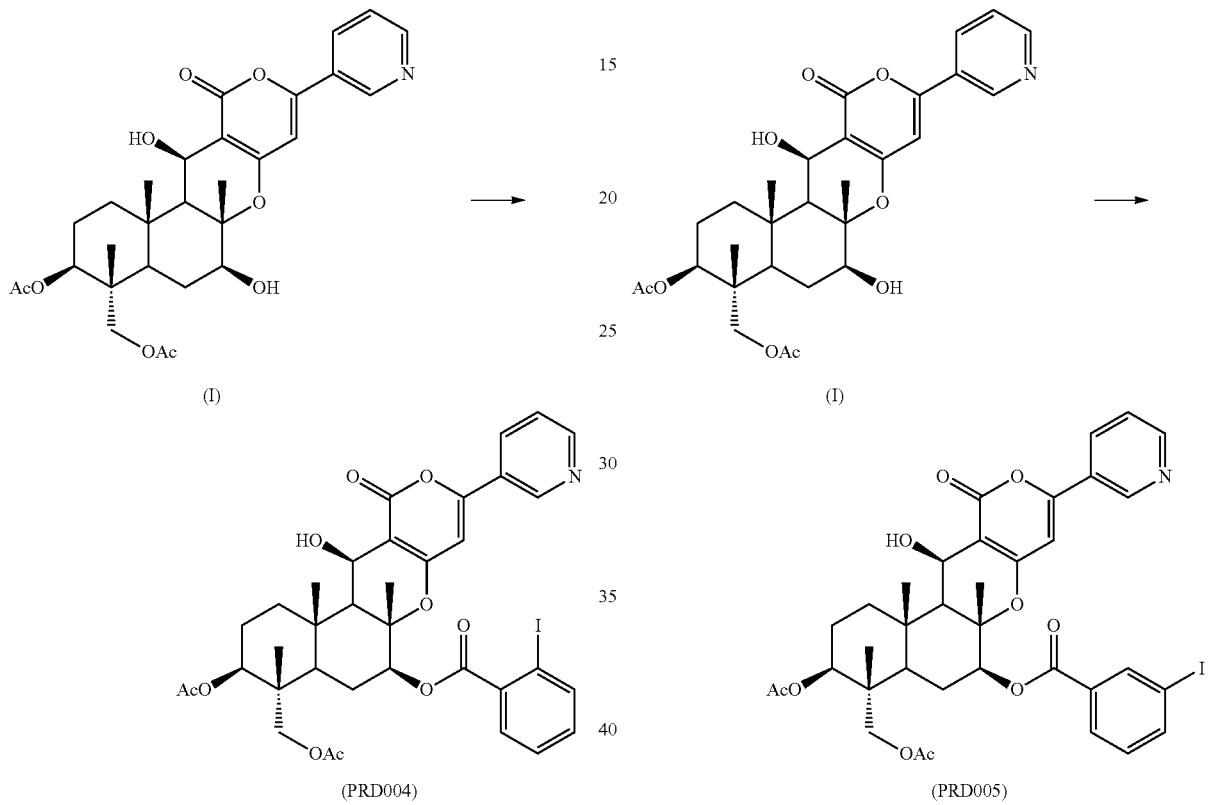

In the same manner as in Example 1, PRD 004 (27.3 mg, 77%) was obtained as a white solid from compound I (25 mg, 46.2 μmol).

$[\alpha]^{24}_D$ +64.58 (c 1.0, CHCl3);

1H NMR (CDCl3, 300 MHz) δ 8.97 (d, 1H, H-2", J=0.9 Hz), 8.67 (dd, 1H, H-6", J=1.8, 4.8 Hz), 8.43 (dd, 1H, H—Ar, J=1.5, 1.8 Hz), 8.09-8.05 (m, 2H, H-4", Ar), 7.96-7.92 (m, 1H, H—Ar), 7.40-7.36 (m, 1H, H-5"), 7.28-7.22 (m, 1H, H—Ar), 6.42 (s, 1H, H-5"), 5.26 (dd, 1H, H-7, J=5.1, 11.1 Hz), 5.04-5.02 (m, 1H, H-13), 4.81 (dd, 1H, H-1, J=5.1, 11.1 Hz), 3.83 (d, 1H, H-11a, J=12.0 Hz), 3.71 (d, 1H, H-11b, J=12.0 Hz), 2.92 (br d, 1H, OH-13, J=1.8 Hz), 2.22-1.38 (m, 8H, H-2', 3', 5', 8', 9'), 2.12 (s, 3H, Ac), 2.05 (s, 3H, Ac), 1.58 (s, 3H, Me), 1.49 (s, 3H, Me), 0.91 (s, 3H, Me).

13C NMR (CDCl3, 150 MHz) δ 170.86, 170.47, 163.95, 163.86, 162.08, 157.33, 151.46, 146.71, 142.05, 138.56, 132.94, 131.98, 130.14, 128.84, 123.58, 102.95, 99.33, 93.87, 83.27, 78.70, 73.49, 64.81, 60.15, 54.73, 45.43, 40.36, 37.88, 36.13, 25.26, 24.88, 22.68, 21.10, 20.81, 17.47, 16.53, 13.19.

FAB-LRMS m/z 772 (MH+); FAB-HRMS (CHCl3) calcd. for C36H39INO10 772.1613 (MH+). found 772.1619 (MH+).

In the same manner as in Example 1, PRD 005 (24.1 mg, 68%) was obtained as a white solid from compound I (25 mg, 46.2 μmol).

$[\alpha]^{24}_D$ +47.62 (c 1.0, CHCl3);

1H NMR (CDCl3, 300 MHz) δ 8.98 (d, 1H, H-2", J=1.8 Hz), 8.67 (dd, 1H, H-6", J=1.8, 4.8 Hz), 8.43 (dd, 1H, H—Ar, J=1.5, 1.8 Hz), 8.09-8.05 (m, 3H, H-4", Ar×2), 7.96-7.92 (m, 1H, H—Ar), 7.40-7.22 (m, 1H, H-5"), 7.24 (s, 1H, H—Ar), 6.43 (s, 1H, H-5"), 5.26 (dd, 1H, H-7, J=5.1, 11.1 Hz), 5.03 (d, 1H, H-13, J=4.2 Hz), 4.82 (dd, 1H, H-1, J=5.1, 11.4 Hz), 3.83 (d, 1H, H-11a, J=12.0 Hz), 3.70 (d, 1H, H-11b, J=12.0 Hz), 3.00 (br s, 1H, OH-13), 2.22-1.34 (m, 8H, H-2', 3', 5', 8', 9'), 2.13 (s, 3H, Ac), 2.05 (s, 3H, Ac), 1.84 (s, 3H, Me), 1.50 (s, 3H, Me), 0.91 (s, 3H, Me).

13C NMR (CDCl3, 150 MHz) δ 178.89, 170.50, 163.98, 163.87, 162.08, 157.22, 151.20, 146.51, 142.08, 138.59, 133.19, 131.99, 130.17, 128.87, 103.03, 99.46, 93.89, 83.32, 78.71, 73.51, 64.84, 60.20, 54.75, 45.46, 40.39, 37.91, 36.16, 25.29, 22.70, 21.12, 20.84, 17.50, 16.54, 13.22.

FAB-LRMS m/z 772 (MH+); FAB-HRMS (CHCl3) calcd. for C36H39INO10 772.1613 (MH+). found 772.1619 (MH+).

Example 6

Preparation of
7-p-iodobenzoyl-7-deacetylpyripyropene A (PRD 006)

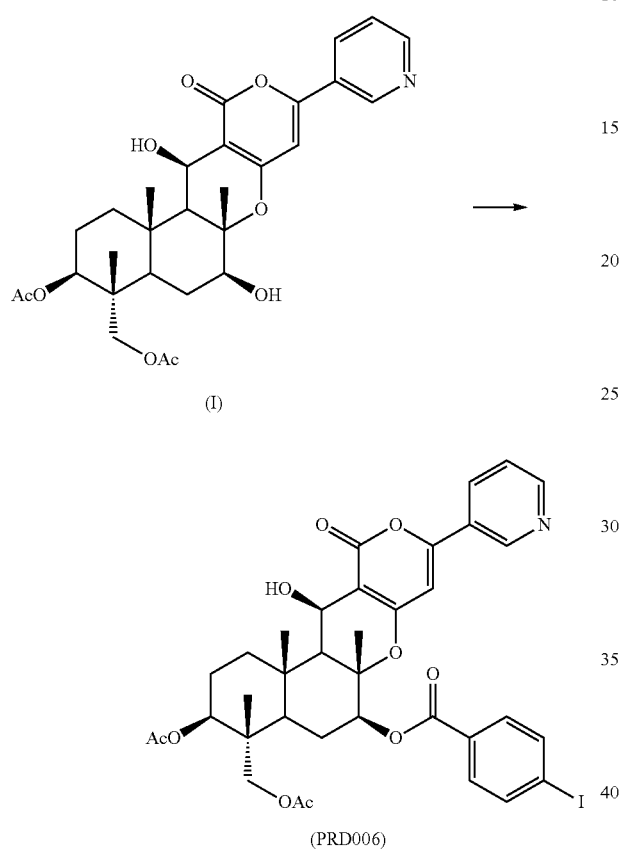

In the same manner as in Example 1, PRD 006 (29.8 mg, 84%) was obtained as a white solid from compound I (25 mg, 46.2 μmol).

$[\alpha]^{24}_D$ +97.46 (c 1.0, CHCl$_3$);

$^1$H NMR (CDCl$_3$, 300 MHz) δ 8.97 (d, 1H, H-2", J=0.9 Hz), 8.67 (dd, 1H, H-6", J=1.8, 4.8 Hz), 8.08-8.04 (m, 1H, H-4"), 7.88-7.79 (m, 4H, H—Ar), 7.40-7.35 (m, 1H, H-5"), 6.41 (s, 1H, H-5'), 5.25 (dd, 1H, H-7, J=4.8, 10.5 Hz), 5.03 (d, 1H, H-13, J=3.9 Hz), 4.82 (dd, 1H, H-1, J=4.8, 11.1 Hz), 3.84 (d, 1H, H-11a, J=12.0 Hz), 3.71 (d, 1H, H-11b, J=12.0 Hz), 3.02 (br s, 1H, OH-13), 2.22-1.46 (m, 8H, H-2', 3', 5', 8', 9'), 2.13 (s, 3H, Ac), 2.05 (s, 3H, Ac), 1.84 (s, 3H, Me), 1.49 (s, 3H, Me), 0.91 (s, 3H, Me).

$^{13}$C NMR (CDCl$_3$, 150 MHz) δ 170.89, 170.48, 164.97, 163.87, 162.09, 157.32, 151.44, 146.69, 137.86, 132.99, 131.11, 129.56, 123.62, 112.51, 102.97, 101.18, 99.33, 83.29, 78.58, 73.50, 64.84, 60.19, 54.74, 45.43, 40.37, 37.88, 36.14, 25.27, 22.68, 21.11, 20.82, 17.48, 16.52, 13.20.

FAB-LRMS m/z 772 (MH$^+$); FAB-HRMS (CHCl$_3$) calcd. for C$_{36}$H$_{39}$INO$_{10}$ 772.1614 (MH$^+$). found 772.1619 (MH$^+$).

Example 7

Preparation of
7-o-methylbenzoyl-7-deacetylpyripyropene A (PRD 007)

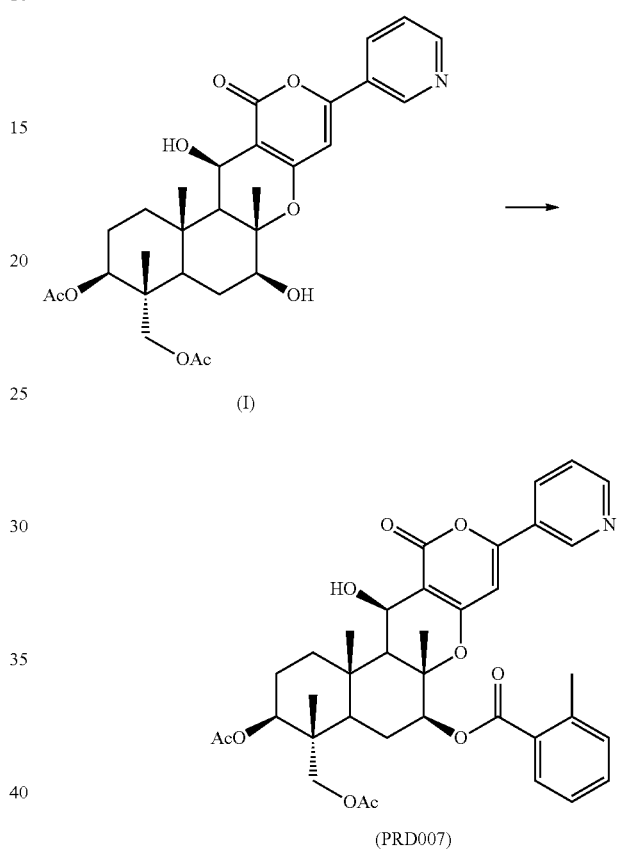

In the same manner as in Example 2, PRD 007 (12.7 mg, 70%) was obtained as a white solid from compound I (15 mg, 27.7 μmol).

$^1$H NMR (CDCl$_3$, 300 MHz) δ 8.98 (d, 1H, H-2", J=2.1 Hz), 8.67 (dd, 1H, H-6", J=1.5, 4.8 Hz), 8.09-8.05 (m, 1H, H-4"), 8.00 (dd, 1H, H—Ar, J=1.8, 8.7 Hz), 7.45-7.27 (m, 2H, H-5", Ar), 7.32-7.27 (m, 2H, H—Ar), 6.42 (s, 1H, H-5'), 5.25 (dd, 1H, H-7, J=4.5, 10.2 Hz), 5.04 (d, 1H, H-13, J=4.2 Hz), 4.83 (dd, 1H, H-1, J=5.4, 11.4 Hz), 3.84 (d, 1H, H-11a, J=12.0 Hz), 3.72 (d, 1H, H-11b, J=12.0 Hz), 3.00 (br s, 1H, OH-13), 2.67 (s, 3H, Ar-Me), 2.22-1.44 (m, 8H, H-2, 3, 5, 8, 9), 2.14 (s, 3H, Ac), 2.05 (s, 3H, Ac), 1.83 (s, 3H, Me), 1.49 (s, 3H, Me), 0.91 (s, 3H, Me).

$^{13}$C NMR (CDCl$_3$, 150 MHz) δ 171.00, 170.53, 166.31, 163.91, 162.15, 140.54, 133.29, 132.27, 131.87, 130.57, 129.45, 125.80, 103.05, 99.54, 83.42, 78.18, 73.60, 64.97, 60.28, 54.85, 45.61, 40.38, 37.96, 36.20, 25.35, 22.74, 21.95, 21.14, 20.86, 17.53, 16.71, 13.27.

FAB-LRMS m/z 660 (MH$^+$); FAB-HRMS (CHCl$_3$) calcd. for C$_{37}$H$_{42}$NO$_{10}$ 660.2809 (MH$^+$). found 660.2820 (MH$^+$).

Example 8

Preparation of 7-m-methylbenzoyl-7-deacetylpyripyropene A (PRD 008)

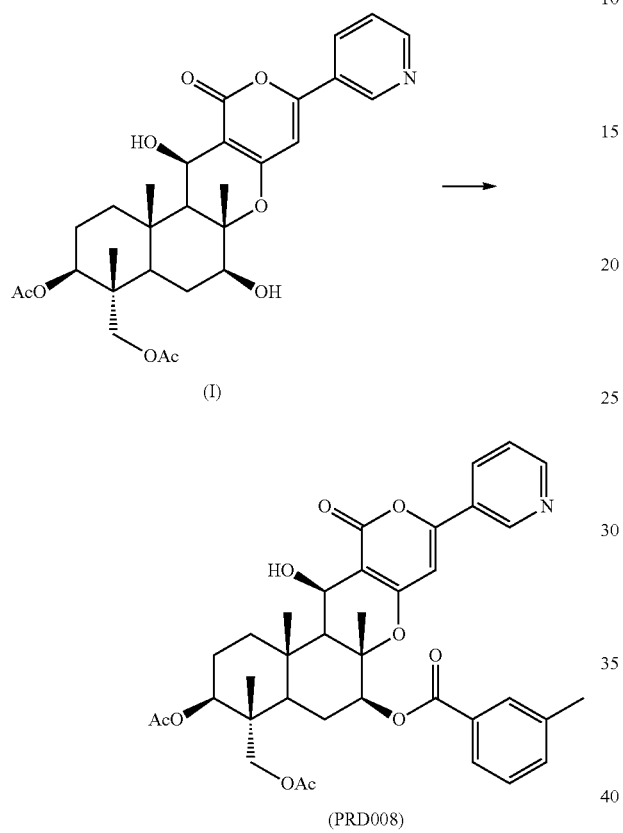

In the same manner as in Example 2, PRD 008 (15.3 mg, 84%) was obtained as a white solid from compound I (15 mg, 27.7 μmol).

$^1$H NMR (CDCl$_3$, 300 MHz) δ 8.97 (d, 1H, H-2", J=1.5 Hz), 8.66 (dd, 1H, H-6", J=1.8, 4.8 Hz), 8.08-8.04 (m, 1H, H-4"), 7.92-7.90 (m, 2H, Ar), 7.41-7.35 (m, 3H, H-5", Ar), 6.42 (s, 1H, H-5'), 5.28 (dd, 1H, H-7, J=5.4, 11.4 Hz), 5.03 (d, 1H, H-13, J=4.2 Hz), 4.82 (dd, 1H, H-1, J=5.1, 11.4 Hz), 3.84 (d, 1H, H-11a, J=12.0 Hz), 3.69 (d, 1H, H-11b, J=12.0 Hz), 3.00 (br s, 1H, OH-13), 2.44 (s, 3H, Ar-Me), 2.22-1.44 (m, 8H, H-2, 3, 5, 8, 9), 2.13 (s, 3H, Ac), 2.05 (s, 3H, Ac), 1.86 (s, 3H, Me), 1.50 (s, 3H, Me), 0.91 (s, 3H, Me).

$^{13}$C NMR (CDCl$_3$, 150 MHz) δ 170.92, 170.51, 165.60, 163.97, 162.21, 157.35, 151.55, 146.82, 138.33, 134.01, 132.89, 130.26, 130.05, 128.38, 127.09, 126.83, 123.57, 102.92, 99.40, 83.45, 78.12, 73.54, 64.87, 60.27, 54.77, 45.46, 40.39, 37.91, 36.17, 25.33, 22.72, 21.31, 21.12, 20.85, 17.51, 16.55, 13.21.

FAB-LRMS m/z 660 (MH$^+$); FAB-HRMS (CHCl$_3$) calcd. for C$_{37}$H$_{42}$NO$_{10}$ 660.2809 (MH$^+$). found 660.2816 (MH$^+$).

Example 9

Preparation of 7-m-methylbenzoyl-7-deacetylpyripyropene A (PRD 009)

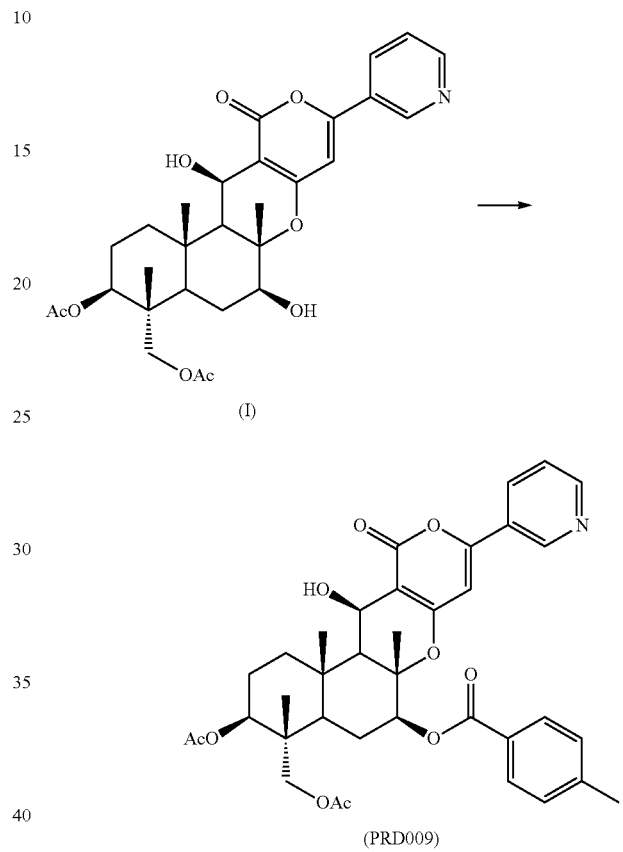

In the same manner as in Example 2, PRD 009 (15.1 mg, 83%) was obtained as a white solid from compound I (15 mg, 27.7 μmol).

$^1$H NMR (CDCl$_3$, 300 MHz) δ 8.96 (d, 1H, H-2", J=1.5 Hz), 8.66 (dd, 1H, H-6", J=1.5, 4.8 Hz), 8.08-8.04 (m, 1H, H-4"), 8.00 (d, 2H, H—Ar, J=8.1 Hz), 7.37 (dd, 1H, H-5", J=4.8, 7.8 Hz), 7.29 (d, 2H, H—Ar, J=8.1 Hz), 6.42 (s, 1H, H-5'), 5.27 (dd, 1H, H-7, J=4.8, 10.5 Hz), 5.03 (d, 1H, H-13, J=3.6 Hz), 4.81 (dd, 1H, H-1, J=5.1, 11.1 Hz), 3.85 (d, 1H, H-11a, J=12.0 Hz), 3.67 (d, 1H, H-11b, J=12.0 Hz), 3.00 (br s, 1H, OH-13), 2.44 (s, 3H, Ar-Me), 2.22-1.44 (m, 8H, H-2, 3, 5, 8, 9), 2.13 (s, 3H, Ac), 2.05 (s, 3H, Ac), 1.85 (s, 3H, Me), 1.50 (s, 3H, Me), 0.91 (s, 3H, Me).

$^{13}$C NMR (CDCl$_3$, 150 MHz) δ 170.93, 170.51, 165.48, 163.97, 162.23, 157.33, 151.54, 146.82, 144.02, 132.88, 129.75, 129.19, 127.38, 127.09, 123.56, 102.91, 99.40, 83.46, 78.01, 73.54, 64.87, 60.27, 54.77, 45.46, 40.39, 37.90, 36.17, 25.35, 22.71, 21.68, 21.12, 20.85, 17.51, 16.54, 13.20.

FAB-LRMS m/z 660 (MH$^+$); FAB-HRMS (CHCl$_3$) calcd. for C$_{37}$H$_{42}$NO$_{10}$ 660.2809 (MH$^+$). found 660.2816 (MH$^+$).

Example 10

Preparation of 7-o-chlorobenzoyl-7-deacetylpyripyropene A (PRD 010)

Example 11

Preparation of 7-m-chlorobenzoyl-7-deacetylpyripyropene A (PRD 011)

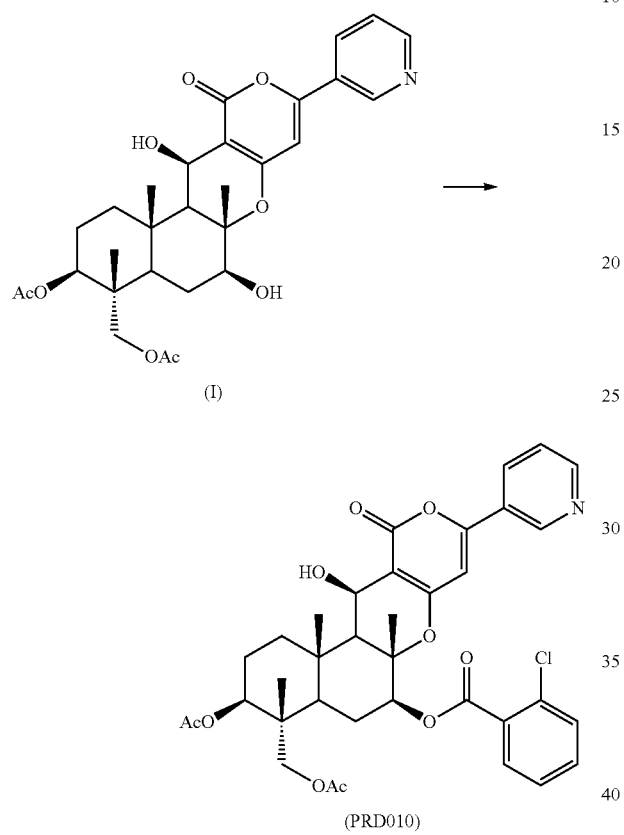

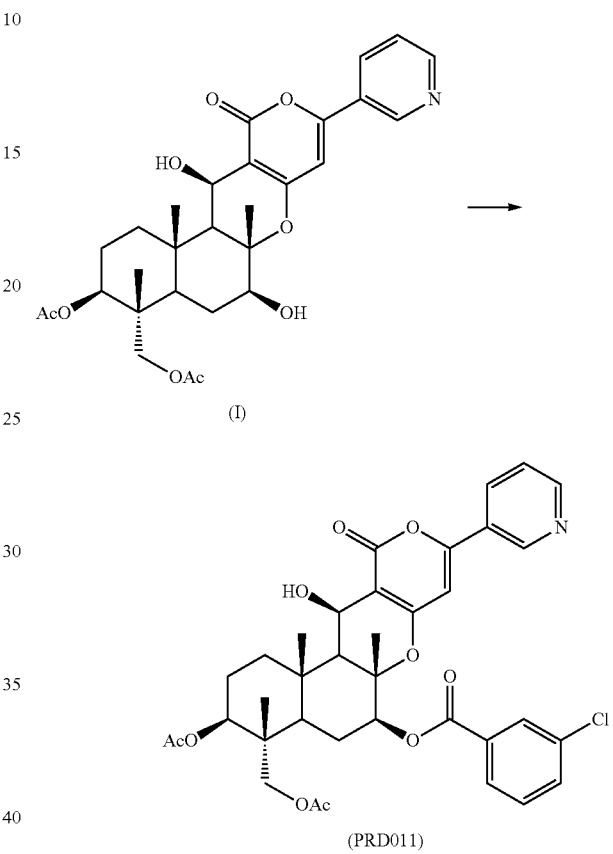

In the same manner as in Example 2, PRD 010 (15.3 mg, 81%) was obtained as a white solid from compound I (15 mg, 27.7 µmol).

$[\alpha]^{24}_D$ +66.59 (c 1.0, CHCl$_3$).

$^1$H NMR (CDCl$_3$, 300 MHz) δ 9.02 (dd, 1H, H-2", J=0.6, 2.4 Hz), 8.68 (dd, 1H, H-6", J=1.8, 5.1 Hz), 8.11-8.07 (m, 1H, H-4"), 7.94-7.91 (m, 1H, Ar), 7.52-7.35 (m, 4H, H-5", Ar), 6.45 (s, 1H, H-5'), 5.28 (dd, 1H, H-7, J=5.4, 11.4 Hz), 5.03 (d, 1H, H-13, J=4.5 Hz), 4.82 (dd, 1H, H-1, J=5.1, 11.4 Hz), 3.87 (d, 1H, H-11a, J=12.0 Hz), 3.71 (d, 1H, H-11b, J=12.0 Hz), 2.56 (br s, 1H, OH-13), 2.22-1.49 (m, 8H, H-2, 3, 5, 8, 9), 2.13 (s, 3H, Ac), 2.05 (s, 3H, Ac), 1.82 (s, 3H, Me), 1.49 (s, 3H, Me), 0.92 (s, 3H, Me).

$^{13}$C NMR (CDCl$_3$, 150 MHz) δ 170.94, 170.51, 164.76, 163.95, 162.16, 157.38, 154.29, 151.52, 146.79, 133.78, 133.01, 132.83, 131.64, 131.25, 130.00, 127.14, 126.68, 123.64, 102.95, 99.37, 83.20, 79.29, 73.53, 64.92, 60.22, 54.76, 45.61, 40.40, 37.92, 36.15, 25.16, 22.70, 21.12, 20.85, 17.52, 16.67, 13.25.

FAB-LRMS m/z 680 (MH$^+$); FAB-HRMS (CHCl$_3$) calcd. for C$_{36}$H$_{39}$NO$_{10}$Cl 680.2262 (MH$^+$). found 680.2278 (MH$^+$).

In the same manner as in Example 2, PRD 011 (15.1 mg, 80%) was obtained as a white solid from compound I (15 mg, 27.7 µmol).

$[\alpha]^{24}_D$ +70.30 (c 1.0, CHCl$_3$);

$^1$H NMR (CDCl$_3$, 300 MHz) δ 8.97 (d, 1H, H-2", J=1.5 Hz), 8.67 (dd, 1H, H-6", J=1.5, 4.8 Hz), 8.09-8.05 (m, 2H, H-4", Ar), 8.02-7.98 (m, 1H, Ar), 7.61-7.57 (m, 1H, Ar), 7.45 (d, 1H, H—Ar, J=7.8 Hz), 7.42-7.36 (m, 1H, H-5"), 6.43 (s, 1H, H-5"), 5.27 (dd, 1H, H-7, J=5.1, 11.1 Hz), 5.04 (d, 1H, H-13, J=4.2 Hz), 4.82 (dd, 1H, H-1, J=5.1, 11.1 Hz), 3.84 (d, 1H, H-11a, J=12.0 Hz), 3.71 (d, 1H, H-11b, J=12.0 Hz), 3.00 (br s, 1H, OH-13), 2.22-1.49 (m, 8H, H-2, 3, 5, 8, 9), 2.13 (s, 3H, Ac), 2.05 (s, 3H, Ac), 1.85 (s, 3H, Me), 1.50 (s, 3H, Me), 0.91 (s, 3H, Me).

$^{13}$C NMR (CDCl$_3$, 150 MHz) δ 170.91, 170.51, 164.28, 163.93, 162.11, 157.41, 151.57, 146.81, 134.67, 133.29, 132.95, 131.86, 129.84, 129.77, 127.88, 127.08, 123.60, 102.96, 99.33, 83.29, 78.77, 73.52, 64.85, 60.22, 54.77, 45.47, 40.39, 37.91, 36.16, 25.29, 22.71, 21.12, 20.84, 17.50, 16.55, 13.22.

FAB-LRMS m/z 680 (MH$^+$); FAB-HRMS (CHCl$_3$) calcd. for C$_{36}$H$_{39}$NO$_{10}$Cl 680.2262 (MH$^+$). found 680.2269 (MH$^+$).

Example 12

Preparation of 7-p-chlorobenzoyl-7-deacetylpyripyropene A (PRD 012)

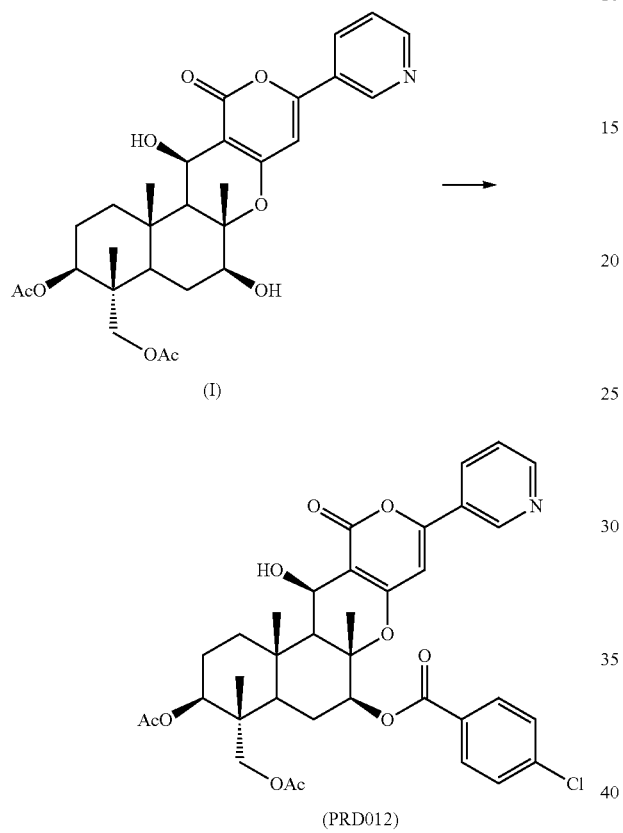

In the same manner as in Example 2, PRD 012 (15.0 mg, 80%) was obtained as a white solid from compound I (15 mg, 27.7 μmol).

$[\alpha]^{24}_D$ +83.21 (c 1.0, CHCl$_3$);

$^1$H NMR (CDCl$_3$, 300 MHz) δ 8.97 (d, 1H, H-2", J=2.1 Hz), 8.67 (dd, 1H, H-6", J=1.5, 4.8 Hz), 8.09-8.02 (m, 3H, H-4", Ar), 7.49-7.45 (m, 2H, Ar), 7.40-7.36 (m, 1H, H-5'), 6.42 (s, 1H, H-5'), 5.26 (dd, 1H, H-7, J=4.8, 11.1 Hz), 5.03 (d, 1H, H-13, J=4.2 Hz), 4.82 (dd, 1H, H-1, J=4.8, 11.1 Hz), 3.83 (d, 1H, H-11a, J=12.0 Hz), 3.70 (d, 1H, H-11b, J=12.0 Hz), 3.00 (br s, 1H, OH-13), 2.22-1.43 (m, 8H, H-2, 3, 5, 8, 9), 2.12 (s, 3H, Ac), 2.05 (s, 3H, Ac), 1.84 (s, 3H, Me), 1.50 (s, 3H, Me), 0.91 (s, 3H, Me).

$^{13}$C NMR (CDCl$_3$, 150 MHz) δ 170.93, 170.51, 164.61, 163.94, 162.13, 157.39, 151.55, 146.78, 139.77, 132.96, 131.10, 128.86, 128.55, 127.09, 123.61, 120.81, 116.43, 102.96, 99.33, 83.31, 78.58, 73.52, 64.86, 60.22, 54.77, 45.44, 40.39, 37.90, 36.16, 25.30, 22.70, 21.12, 20.89, 20.84, 17.50, 16.54, 13.22.

FAB-LRMS m/z 680 (MH$^+$); FAB-HRMS (CHCl$_3$) calcd. for C$_{36}$H$_{39}$NO$_{10}$Cl 680.2262 (MH$^+$). found 680.2269 (MH$^+$).

Example 13

Preparation of 7-m-vinylbenzoyl-7-deacetylpyripyropene A (PRD 013)

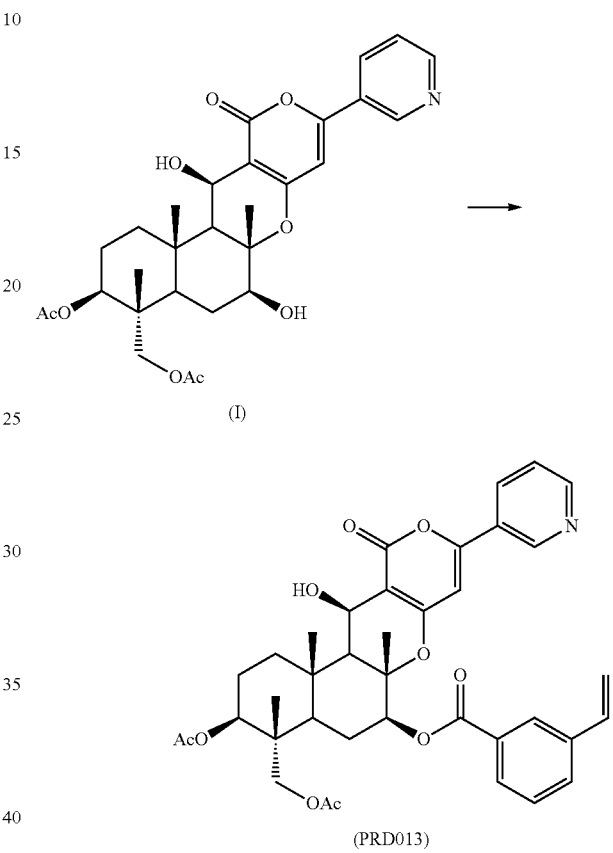

In the same manner as in Example 1, PRD 013 (16.3 mg, 88%) was obtained as a white solid from compound I (15 mg, 27.7 μmol).

$[\alpha]^{24}_D$ +92.56 (c 1.0, CHCl$_3$);

$^1$H NMR (CDCl$_3$, 300 MHz) δ 8.97 (d, 1H, H-2", J=2.1 Hz), 8.66 (dd, 1H, H-6", J=1.2, 4.5 Hz), 8.14 (dd, 1H, H—Ar, J=1.2, 1.8 Hz), 8.08-8.04 (m, 1H, H-4"), 7.99 (dd, 1H, H—Ar, J=1.2, 7.5 Hz), 7.65 (d, 1H, H—Ar, J=8.1 Hz), 7.46 (t, 1H, H—Ar, J=8.1 Hz), 7.37 (dd, 1H, H-5", J=4.5, 8.1 Hz), 6.78 (dd, 1H, H-vinyl, J=10.8, 17.7 Hz), 6.43 (s, 1H, H-5'), 5.85 (d, 1H, H-vinyl, J=17.7 Hz), 5.36 (d 1H, H-vinyl, J=10.8 Hz), 5.28 (dd, 1H, H-7, J=4.8, 11.4 Hz), 5.04 (d, 1H, H-13, J=4.2 Hz), 4.82 (dd, 1H, H-1, J=5.1, 11.4 Hz), 3.85 (d, 1H, H-11a, J=11.7 Hz), 3.70 (d, 1H, H-11b, J=11.7 Hz), 3.00 (br s, 1H, OH-13), 2.23-1.44 (m, 8H, H-2', 3', 5', 8', 9'), 2.14 (s, 3H, Ac), 2.05 (s, 3H, Ac), 1.87 (s, 3H, Me), 1.50 (s, 3H, Me), 0.90 (s, 3H, Me).

FAB-LRMS m/z 672 (MH$^+$); FAB-HRMS (CHCl$_3$) calcd. for C$_{38}$H$_{42}$NO$_{10}$ 672.2809 (MH$^+$). found 672.2823 (MH$^+$).

Example 14

Preparation of
7-p-vinylbenzoyl-7-deacetylpyripyropene A (PRD 014)

Example 15

Preparation of
7-o-cyanobenzoyl-7-deacetylpyripyropene A (PRD 015)

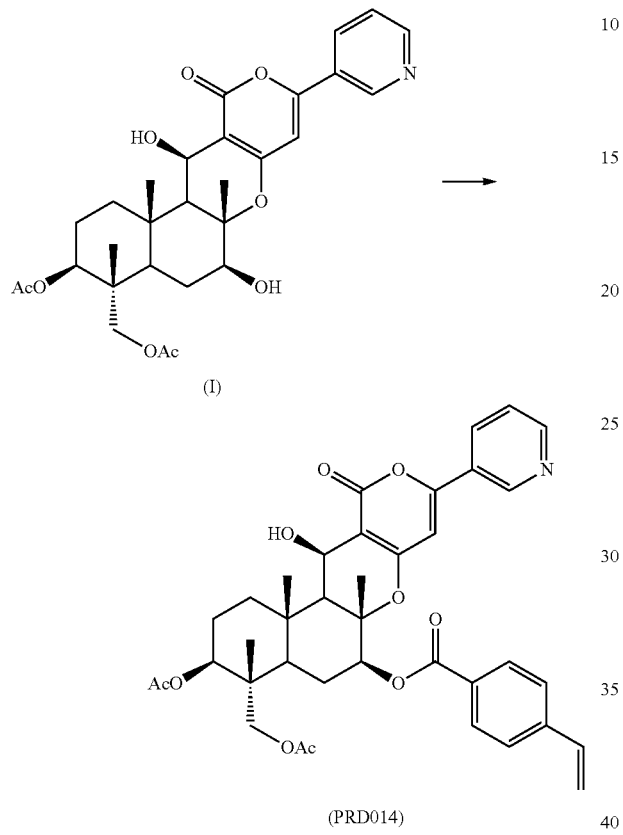

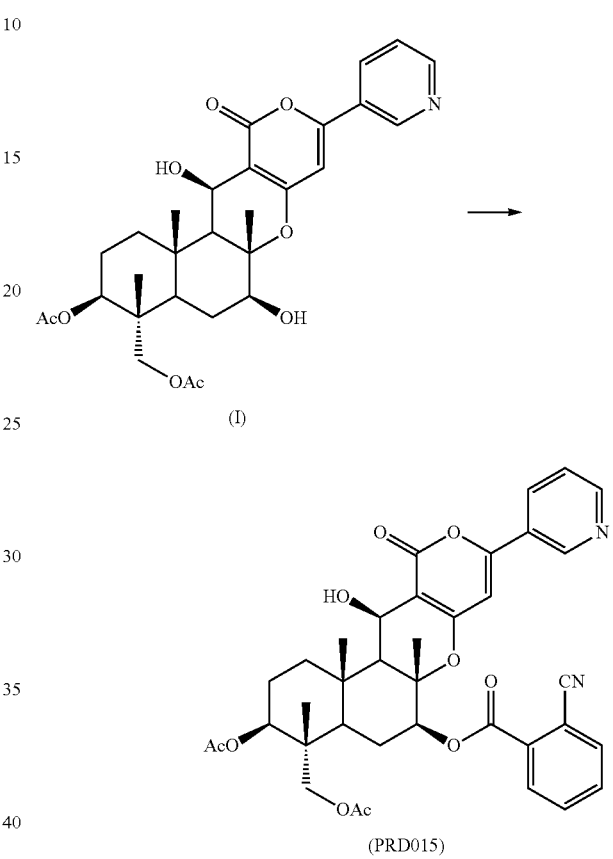

In the same manner as in Example 1, PRD 014 (16.1 mg, 87%) was obtained as a white solid from compound I (15 mg, 27.7 μmol).

$[\alpha]^{24}_D$ +81.54 (c 1.0, CHCl$_3$);

$^1$H NMR (CDCl$_3$, 300 MHz) δ 8.97 (d, 1H, H-2", J=1.8 Hz), 8.66 (dd, 1H, H-6", J=1.5, 4.8 Hz), 8.08-8.04 (m, 3H, H-4", Ar×2), 7.51 (d, 2H, H—Ar×2, J=8.4 Hz), 7.39-7.35 (m, 1H, H-5"), 6.78 (dd, 1H, H-vinyl, J=11.1, 17.7 Hz), 6.42 (s, 1H, H-5'), 5.89 (d, 1H, H-vinyl, J=17.7 Hz), 5.41 (d, 1H, H-vinyl, J=11.1 Hz), 5.27 (dd, 1H, H-7, J=5.4, 11.1 Hz), 5.04 (d, 1H, H-13, J=4.2 Hz), 4.82 (dd, 1H, H-1, J=5.4, 11.4 Hz), 3.85 (d, 1H, H-11a, J=12.0 Hz), 3.68 (d, 1H, H-11b, J=12.0 Hz), 3.00 (br s, 1H, OH-13), 2.22-1.43 (m, 8H, H-2', 3', 5', 8', 9'), 2.13 (s, 3H, Ac), 2.05 (s, 3H, Ac), 1.84 (s, 3H, Me), 1.50 (s, 3H, Me), 0.91 (s, 3H, Me).

$^{13}$C NMR (CDCl$_3$, 150 MHz) δ 170.92, 170.50, 165.19, 163.95, 162.20, 157.35, 151.54, 146.81, 142.31, 135.89, 132.89, 130.04, 129.19, 127.08, 126.20, 123.56, 116.79, 102.92, 99.38, 83.41, 78.21, 73.53, 64.87, 60.25, 54.77, 45.46, 40.39, 37.90, 36.16, 33.91, 25.58, 25.33, 24.90, 22.71, 21.11, 20.85, 17.50, 16.54, 13.20.

FAB-LRMS m/z 672 (MH$^+$); FAB-HRMS (CHCl$_3$) calcd. for C$_{38}$H$_{42}$NO$_{10}$ 672.2809 (MH$^+$). found 672.2796 (MH$^+$).

In the same manner as in Example 2, PRD 015 (14.5 mg, 78%) was obtained as a white solid from compound I (15 mg, 27.7 μmol).

$[\alpha]^{24}_D$ +40.65 (c 1.0, CHCl$_3$);

$^1$H NMR (CDCl$_3$, 300 MHz) δ 8.99 (d, 1H, H-2", J=2.4 Hz), 8.68 (dd, 1H, H-6", J=1.5, 6.3 Hz), 8.23-8.20 (m, 1H, H—Ar), 8.11-8.07 (m, 1H, H-4"), 7.88-7.85 (m, 1H, H—Ar), 7.77-7.71 (m, 2H, H—Ar), 7.42-7.27 (m, 1H, H-5"), 6.47 (s, 1H, H-5'), 5.37 (dd, 1H, H-7, J=5.4, 11.1 Hz), 5.04 (d, 1H, H-13, J=3.9 Hz), 4.82 (dd, 1H, H-1, J=5.1, 11.4 Hz), 3.86 (d, 1H, H-11a, J=12.0 Hz), 3.71 (d, 1H, H-11b, J=12.0 Hz), 2.75 (br s, 1H, OH-13), 2.23-1.50 (m, 8H, H-2, 3, 5, 8, 9), 2.13 (s, 3H, Ac), 2.05 (s, 3H, Ac), 1.88 (s, 3H, Me), 1.50 (s, 3H, Me), 0.92 (s, 3H, Me).

$^{13}$C NMR (CDCl$_3$, 150 MHz) δ 170.92, 170.50, 163.91, 163.28, 162.08, 157.33, 151.44, 146.73, 134.93, 133.06, 132.87, 132.57, 131.39, 127.16, 126.56, 123.65, 117.58, 112.89, 102.98, 99.40, 83.23, 80.10, 73.50, 64.84, 60.21, 54.77, 45.65, 40.42, 37.92, 36.12, 25.22, 22.70, 21.12, 20.85, 17.52, 16.84, 13.26.

FAB-LRMS m/z 671 (MH$^+$); FAB-HRMS (CHCl$_3$) calcd. for C$_{37}$H$_{39}$N$_2$O$_{10}$ 671.2605 (MH$^+$). found 671.2617 (MH$^+$).

Example 16

Preparation of
7-m-cyanobenzoyl-7-deacetylpyripyropene A (PRD 016)

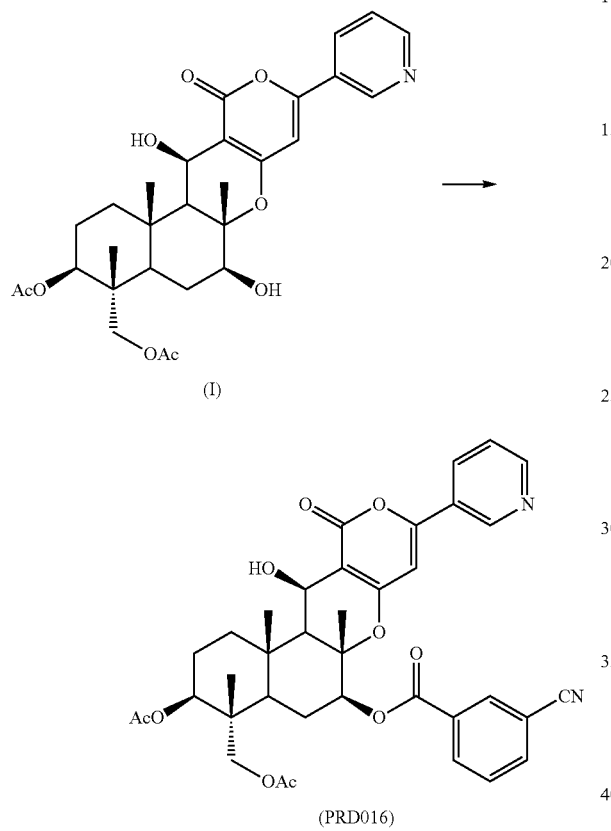

In the same manner as in Example 2, PRD 016 (14.4 mg, 78%) was obtained as a white solid from compound I (15 mg, 27.7 μmol).

$[\alpha]^{24}_D$ +56.56 (c 1.0, CHCl$_3$);

$^1$H NMR (CDCl$_3$, 300 MHz) δ 8.90 (dd, 1H, H-2", J=0.6, 2.4 Hz), 8.60 (dd, 1H, H-6", J=1.5, 4.8 Hz), 8.31-8.25 (m, 2H, H—Ar), 8.03-7.99 (m, 1H, H-4"), 7.84-7.81 (m, 1H, H—Ar), 7.61-7.55 (m, 1H, H—Ar), 7.34-7.30 (m, 1H, H-5"), 6.34 (s, 1H, H-5'), 5.20 (dd, 1H, H-7, J=5.4, 11.7 Hz), 4.97 (d, 1H, H-13, J=4.2 Hz), 4.75 (dd, 1H, H-1, J=5.1, 11.4 Hz), 3.74 (d, 1H, H-11a, J=12.0 Hz), 3.65 (d, 1H, H-11b, J=12.0 Hz), 3.00 (br s, 1H, OH-13), 2.16-1.36 (m, 8H, H-2, 3, 5, 8, 9), 2.06 (s, 3H, Ac), 1.98 (s, 3H, Ac), 1.79 (s, 3H, Me), 1.44 (s, 3H, Me), 0.84 (s, 3H, Me).

$^{13}$C NMR (CDCl$_3$, 150 MHz) δ 170.90, 170.51, 163.87, 163.53, 162.00, 157.40, 151.49, 146.69, 136.25, 133.83, 133.30, 133.05, 131.42, 129.60, 127.10, 123.66, 117.80, 113.11, 103.02, 99.26, 83.16, 79.28, 73.49, 64.84, 60.14, 54.76, 45.45, 40.38, 37.91, 36.14, 25.26, 22.69, 21.11, 20.82, 17.49, 16.58, 13.23.

FAB-LRMS m/z 671 (MH$^+$); FAB-HRMS (CHCl$_3$) calcd. for C$_{37}$H$_{39}$N$_2$O$_{10}$ 671.2605 (MH$^+$). found 671.2621 (MH$^+$).

Example 17

Preparation of
7-p-cyanobenzoyl-7-deacetylpyripyropene A (PRD 017)

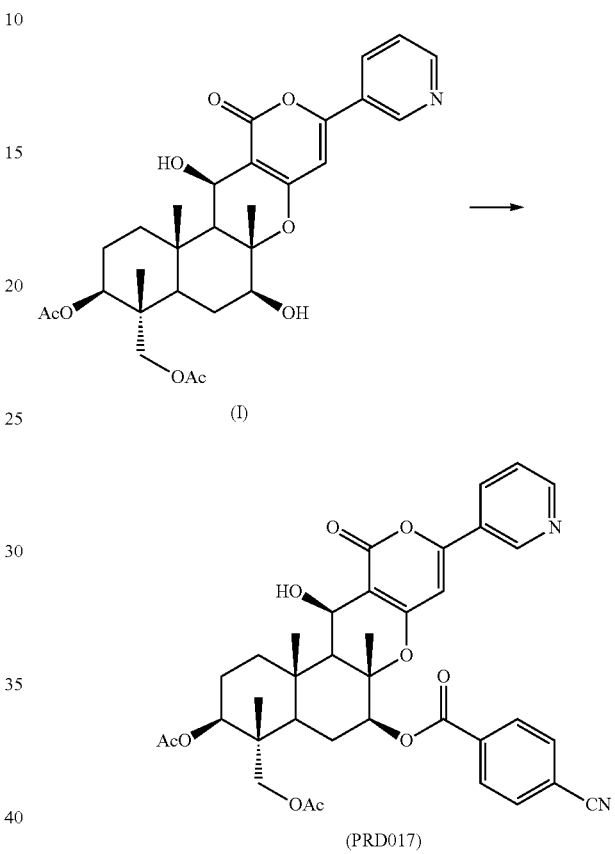

In the same manner as in Example 2, PRD 017 (14.6 mg, 78%) was obtained as a white solid from compound I (15 mg, 27.7 μmol).

$[\alpha]^{24}_D$ +72.27 (c 1.0, CHCl$_3$);

$^1$H NMR (CDCl$_3$, 300 MHz) δ 8.96 (dd, 1H, H-2", J=0.6, 2.4 Hz), 8.67 (dd, 1H, H-6", J=1.5, 4.8 Hz), 8.21 (d, 2H, H—Ar, J=7.8 Hz), 8.09-8.05 (m, 1H, H-4"), 7.80 (d, 2H, H—Ar, J=7.8 Hz), 7.41-7.36 (m, 1H, H-5"), 6.40 (s, 1H, H-5'), 5.29 (dd, 1H, H-7, J=6.0, 11.1 Hz), 5.04 (d, 1H, H-13, J=4.2 Hz), 4.82 (dd, 1H, H-1, J=6.0, 11.0 Hz), 3.82 (d, 1H, H-11a, J=12.0 Hz), 3.73 (d, 1H, H-11b, J=12.0 Hz), 3.00 (br s, 1H, OH-13), 2.18-1.50 (m, 8H, H-2, 3, 5, 8, 9), 2.13 (s, 3H, Ac), 2.05 (s, 3H, Ac), 1.85 (s, 3H, Me), 1.50 (s, 3H, Me), 0.91 (s, 3H, Me).

$^{13}$C NMR (CDCl$_3$, 150 MHz) δ 170.90, 170.50, 163.87, 162.00, 159.68, 157.47, 153.70, 151.60, 146.76, 133.90, 132.95, 132.33, 130.23, 127.04, 123.62, 117.84, 116.71, 102.99, 99.20, 83.15, 79.29, 73.48, 64.84, 60.16, 54.75, 45.43, 40.38, 37.91, 36.14, 25.24, 22.68, 21.11, 20.82, 17.49, 16.55, 13.23.

FAB-LRMS m/z 671 (MH$^+$); FAB-HRMS (CHCl$_3$) calcd. for C$_{37}$H$_{39}$N$_2$O$_{10}$ 671.2605 (MH$^+$). found 671.2600 (MH$^+$).

Example 18

Preparation of
7-m-methylthiobenzoyl-7-deacetylpyripyropene A
(PRD 023)

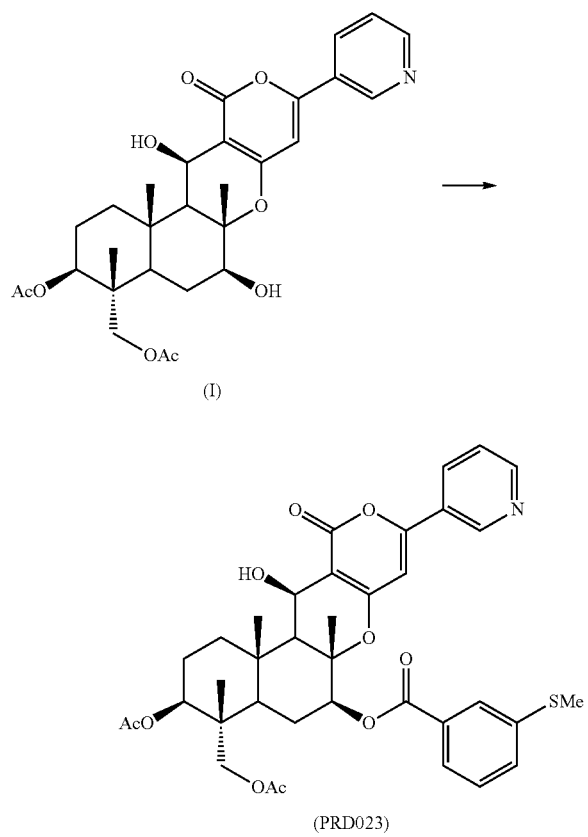

(PRD023)

In the same manner as in Example 2, PRD 023 (12.0 mg, 94%) was obtained as a white solid from compound I (10 mg, 18.5 μmol).

$^1$H NMR (CDCl$_3$, 300 MHz) δ 8.91 (d, 1H, H-2", J=2.1 Hz), 8.60 (dd, 1H, H-6", J=1.5, 5.1 Hz), 8.02-7.98 (m, 1H, H-4"), 7.91-7.90 (m, 1H, H—Ar), 7.81-7.77 (m, 1H, H—Ar), 7.43-7.29 (m, 3H, H-5", Ar), 6.36 (s, 1H, H-5'), 5.20 (dd, 1H, H-7, J=5.4, 11.4 Hz), 4.97 (d, 1H, H-13, J=4.2 Hz), 4.75 (dd, 1H, H-1, J=5.1, 11.1 Hz), 3.78 (d, 1H, H-11a, J=12.0 Hz), 3.63 (d, 1H, H-11b, J=12.0 Hz), 2.92 (br s, 1H, OH-13), 2.48 (s, 3H, SMe), 2.15-1.41 (m, 8H, H-2, 3, 5, 8, 9), 2.06 (s, 3H, Ac), 1.98 (s, 3H, Ac), 1.78 (s, 3H, Me), 1.43 (s, 3H, Me), 0.84 (s, 3H, Me).

$^{13}$C NMR (CDCl$_3$, 150 MHz) δ 170.92, 170.51, 165.05, 163.95, 162.16, 157.40, 151.57, 146.82, 139.56, 132.91, 130.99, 130.76, 128.86, 127.27, 127.08, 126.16, 123.58, 102.93, 99.37, 83.36, 78.45, 73.52, 64.87, 60.26, 54.77, 45.46, 40.40, 37.91, 36.16, 25.31, 22.71, 21.12, 20.86, 17.51, 16.55, 15.65, 13.21.

FAB-LRMS m/z 692 (MH$^+$); FAB-HRMS (CHCl$_3$) calcd. for C$_{37}$H$_{42}$NO$_{10}$S 692.2529 (MH$^+$). found 692.2545 (MH$^+$).

Example 19

Preparation of
7-p-methylthiobenzoyl-7-deacetylpyripyropene A
(PRD 018)

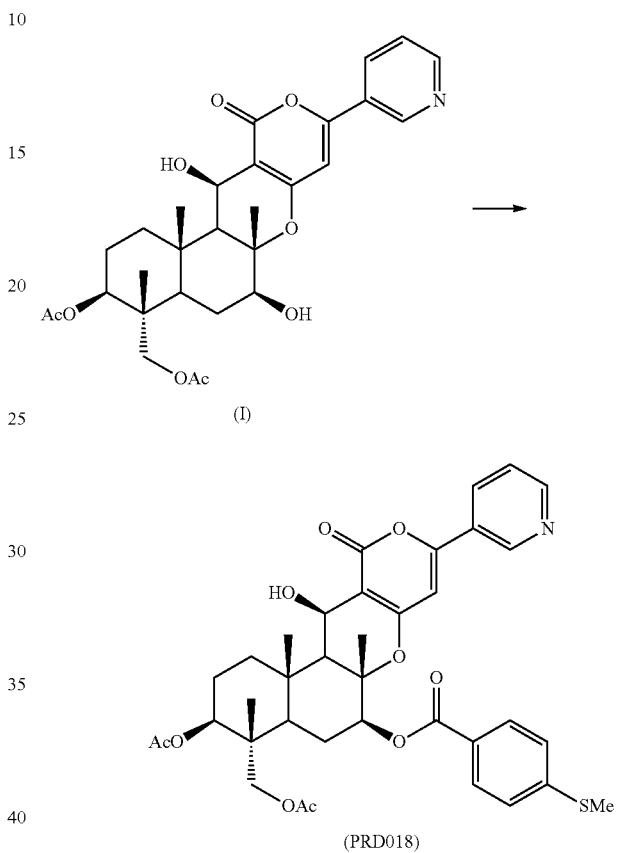

(PRD018)

In the same manner as in Example 2, PRD 018 (12.7 mg, 100%) was obtained as a white solid from compound I (10 mg, 18.5 μmol).

[α]$^{24}_D$ +87.00 (c 1.0, CHCl$_3$);

$^1$H NMR (CDCl$_3$, 300 MHz) δ 8.90 (d, 1H, H-2", J=1.5 Hz), 8.59 (dd, 1H, H-6", J=1.8, 4.8 Hz), 8.01-7.97 (m, 1H, H-4"), 7.93 (dd, 2H, H—Ar, J=2.1, 6.9 Hz), 7.93 (dd, 2H, H—Ar, J=2.1, 6.9 Hz), 7.33-7.28 (m, 1H, H-5"), 6.34 (s, 1H, H-5'), 5.18 (dd, 1H, H-7, J=4.8, 10.8 Hz), 4.96 (dd, 1H, H-13, J=2.1, 3.6 Hz), 4.74 (dd, 1H, H-1, J=5.1, 11.1 Hz), 3.78 (d, 1H, H-11a, J=12.0 Hz), 3.62 (d, 1H, H-11b, J=12.0 Hz), 2.90 (br d, 1H, OH-13, J=2.1 Hz), 2.47 (s, 3H, SMe), 2.15-1.42 (m, 8H, H-2, 3, 5, 8, 9), 2.06 (s, 3H, Ac), 2.05 (s, 3H, Ac), 1.77 (s, 3H, Me), 1.42 (s, 3H, Me), 0.84 (s, 3H, Me).

$^{13}$C NMR (CDCl$_3$, 150 MHz) δ 170.95, 170.52, 165.19, 163.98, 162.21, 157.34, 151.54, 146.81, 146.04, 132.93, 129.99, 127.10, 126.14, 124.99, 123.59, 102.93, 99.40, 83.43, 78.13, 73.54, 64.88, 60.26, 54.77, 45.45, 40.39, 37.90, 36.16, 25.35, 22.71, 21.12, 20.85, 17.51, 16.54, 14.82, 13.21.

FAB-LRMS m/z 692 (MH$^+$); FAB-HRMS (CHCl$_3$) calcd. for C$_{37}$H$_{42}$NO$_{10}$S 692.2529 (MH$^+$). found 692.2539 (MH$^+$).

Example 20

Preparation of
7-m-bromobenzoyl-7-deacetylpyripyropene A (PRD 026)

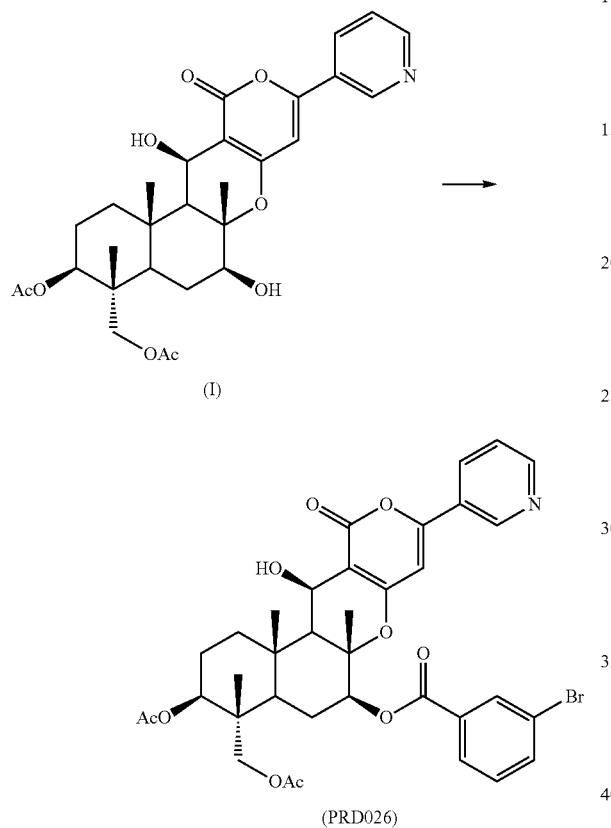

In the same manner as in Example 2, PRD 026 (9.5 mg, 71%) was obtained as a white solid from compound I (10 mg, 18.5 μmol).

$^1$H NMR (CDCl$_3$, 300 MHz) δ 8.97 (d, 1H, H-2", J=2.1 Hz), 8.66 (dd, 1H, H-6", J=1.5, 4.8 Hz), 8.23-8.21 (m, 1H, H—Ar), 8.09-8.02 (m, 2H, H-4", Ar), 7.75-7.72 (m, 1H, H—Ar), 7.40-7.35 (m, 2H, H-5", Ar), 6.42 (s, 1H, H-5'), 5.26 (dd, 1H, H-7, J=5.1, 11.4 Hz), 5.03 (d, 1H, H-13, J=2.7 Hz), 4.81 (dd, 1H, H-1, J=5.1, 11.4 Hz), 3.83 (d, 1H, H-11a, J=12.0 Hz), 3.70 (d, 1H, H-11b, J=12.0 Hz), 2.97 (br s, 1H, OH-13), 2.22-1.43 (m, 8H, H-2, 3, 5, 8, 9), 2.13 (s, 3H, Ac), 2.05 (s, 3H, Ac), 1.84 (s, 3H, Me), 1.49 (s, 3H, Me), 0.90 (s, 3H, Me).

$^{13}$C NMR (CDCl$_3$, 150 MHz) δ 170.90, 170.51, 164.15, 163.93, 162.11, 157.40, 151.57, 146.81, 136.21, 132.98, 132.70, 132.06, 130.09, 128.33, 123.62, 122.59, 102.97, 99.36, 83.30, 78.77, 73.53, 64.85, 60.25, 54.78, 45.47, 40.40, 37.92, 36.17, 29.67, 25.30, 22.71, 21.13, 20.85, 17.51, 16.56, 13.23.

FAB-LRMS m/z 724 (MH$^+$); FAB-HRMS (CHCl$_3$) calcd. for C$_{36}$H$_{39}$BrNO$_{10}$ 724.1757 (MH$^+$). found 724.1744 (MH$^+$).

Example 21

Preparation of
7-p-bromobenzoyl-7-deacetylpyripyropene A (PRD 019)

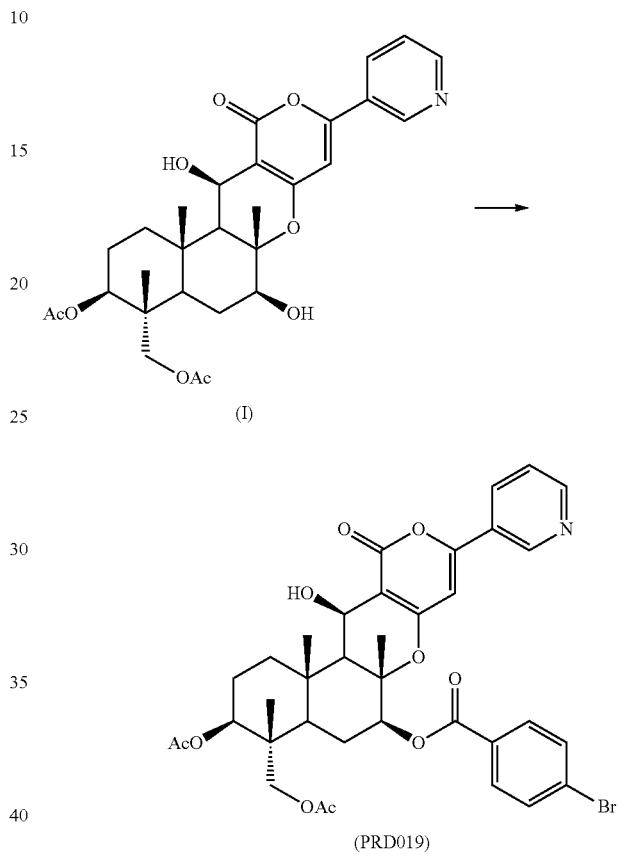

In the same manner as in Example 2, PRD 019 (12.5 mg, 93%) was obtained as a white solid from compound I (10 mg, 18.5 μmol).

$[\alpha]^{24}{}_D$ L+50.95 (c 1.0, CHCl$_3$);

$^1$H NMR (CDCl$_3$, 300 MHz) δ 8.90 (d, 1H, H-2", J=2.1 Hz), 8.59 (dd, 1H, J=1.5, 4.8 Hz), 8.01-7.98 (m, 1H, H-4"), 7.90 (d, 2H, H—Ar, J=8.2 Hz), 7.56 (d, 2H, H—Ar, J=8.2 Hz), 7.33-7.20 (m, 1H, H-5"), 6.34 (s, 1H, H-5'), 5.18 (dd, 1H, H-7, J=4.5, 10.8 Hz), 4.96 (d, 1H, H-13, J=2.1 Hz), 4.75 (dd, 1H, H-1, J=5.1, 11.1 Hz), 3.76 (d, 1H, H-11a, J=12.0 Hz), 3.64 (d, 1H, H-11b, J=12.0 Hz), 2.91 (br s, 1H, OH-13), 2.15-1.35 (m, 8H, H-2, 3, 5, 8, 9), 2.06 (s, 3H, Ac), 1.98 (s, 3H, Ac), 1.77 (s, 3H, Me), 1.42 (s, 3H, Me), 0.84 (s, 3H, Me).

$^{13}$C NMR (CDCl$_3$, 150 MHz) δ 170.93, 170.51, 164.76, 163.94, 162.12, 157.43, 151.60, 146.82, 132.93, 131.87, 131.23, 129.00, 128.44, 127.07, 123.60, 102.95, 99.32, 83.30, 78.62, 73.52, 64.87, 60.25, 54.78, 45.45, 40.39, 37.91, 36.17, 32.35, 30.91, 25.30, 22.71, 21.13, 20.85, 17.51, 16.54, 13.23.

FAB-LRMS m/z 724 (MH$^+$); FAB-HRMS (CHCl$_3$) calcd. for C$_{36}$H$_{39}$BrNO$_{10}$ 724.1757 (MH$^+$). found 724.1740 (MH$^+$).

Example 22

Preparation of 7-o-fluorobenzoyl-7-deacetylpyripyropene A (PRD 028)

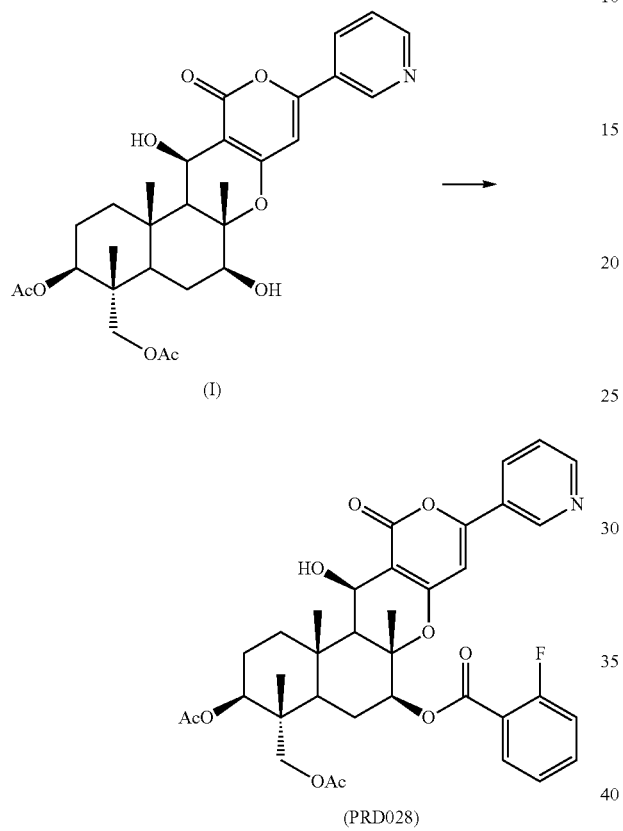

Example 23

Preparation of 7-m-fluorobenzoyl-7-deacetylpyripyropene A (PRD 024)

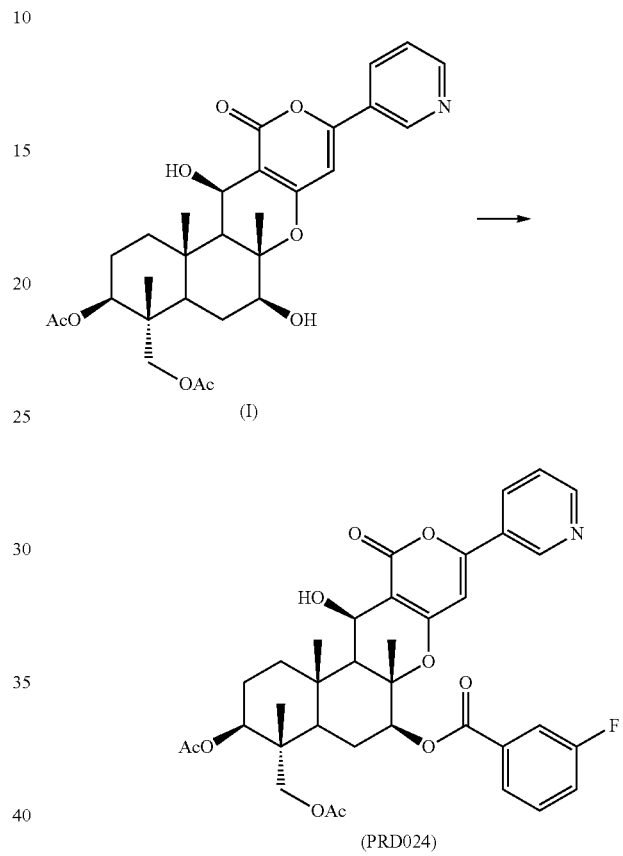

In the same manner as in Example 2, PRD 028 (12.2 mg, 99%) was obtained as a white solid from compound I (10 mg, 18.5 μmol).

$^1$H NMR (CDCl$_3$, 300 MHz) δ 8.98 (d, 1H, H-2", J=1.8 Hz), 8.67-8.66 (m, 1H, H-6"), 8.10-8.00 (m, 2H, H-4", Ar), 7.58-7.55 (m, 1H, H—Ar), 7.38 (dd, 1H, H-5", J=4.8, 8.1 Hz), 7.28-7.14 (m, 2H, H—Ar), 6.45 (s, 1H, H-5'), 5.27 (dd, 1H, H-7, J=5.4, 11.7 Hz), 5.02 (d, 1H, H-13, J=4.2 Hz), 4.81 (dd, 1H, H-1, J=5.1, 11.4 Hz), 3.85 (d, 1H, H-11a, J=12.0 Hz), 3.68 (d, 1H, H-11b, J=12.0 Hz), 2.98 (br s, 1H, OH-13), 2.21-1.41 (m, 8H, H-2, 3, 5, 8, 9), 2.12 (s, 3H, Ac), 2.04 (s, 3H, Ac), 1.82 (s, 3H, Me), 1.48 (s, 3H, Me), 0.90 (s, 3H, Me).

$^{13}$C NMR (CDCl$_3$, 150 MHz) δ 170.93, 170.52, 163.72, 162.08, 161.20, 156.48, 149.93, 145.47, 134.85 (J=8.1 Hz), 134.25, 132.40, 124.22, 124.11, 118.56, 117.22, 117.07, 103.31, 99.99, 83.46, 78.82, 73.52, 64.89, 60.24, 54.72, 45.51, 40.40, 37.93, 36.16, 29.67, 25.25, 22.71, 21.12, 20.86, 17.52, 16.48, 13.22.

FAB-LRMS m/z 664 (MH$^+$); FAB-HRMS (CHCl$_3$) calcd. for C$_{36}$H$_{39}$FNO$_{10}$ 664.2558 (MH$^+$). found 664.2581 (MH$^+$).

In the same manner as in Example 2, PRD 024 (11.7 mg, 95%) was obtained as a white solid from compound I (10 mg, 18.5 μmol).

$^1$H NMR (CDCl$_3$, 300 MHz) δ 8.97 (d, 1H, H-2", J=2.1 Hz), 8.66 (dd, 1H, H-6", J=1.5, 4.8 Hz), 8.08-8.04 (m, 1H, H-4"), 7.92-7.88 (m, 1H, H—Ar), 7.79-7.75 (m, 1H, H—Ar), 7.51-7.44 (m, 1H, H—Ar), 7.40-7.28 (m, 2H, H-5", Ar), 6.42 (s, 1H, H-5'), 5.26 (dd, 1H, H-7, J=4.8, 11.1 Hz), 5.03 (d, 1H, H-13, J=4.2 Hz), 4.81 (dd, 1H, H-1, J=5.1, 11.4 Hz), 3.85 (d, 1H, H-11a, J=12.0 Hz), 3.68 (d, 1H, H-11b, J=12.0 Hz), 2.98 (br s, 1H, OH-13), 2.21-1.41 (m, 8H, H-2, 3, 5, 8, 9), 2.12 (s, 3H, Ac), 2.04 (s, 3H, Ac), 1.82 (s, 3H, Me), 1.48 (s, 3H, Me), 0.90 (s, 3H, Me).

$^{13}$C NMR (CDCl$_3$, 150 MHz) δ 170.92, 170.51, 163.93, 162.12, 161.76, 157.42, 151.57, 146.81, 132.94, 130.67 (d, J=15.6 Hz), 127.08, 125.48, 123.60, 120.42, 120.28, 116.70, 116.54, 102.96, 99.33, 83.30, 78.74, 73.52, 64.87, 60.24, 54.78, 45.46, 40.40, 37.92, 36.17, 25.29, 22.71, 21.13, 20.85, 17.51, 16.54, 13.23.

FAB-LRMS m/z 664 (MH$^+$); FAB-HRMS (CHCl$_3$) calcd. for C$_{36}$H$_{39}$FNO$_{10}$ 664.2558 (MH$^+$). found 664.2581 (MH$^+$).

Example 24

Preparation of
7-p-fluorobenzoyl-7-deacetylpyripyropene A (PRD 020)

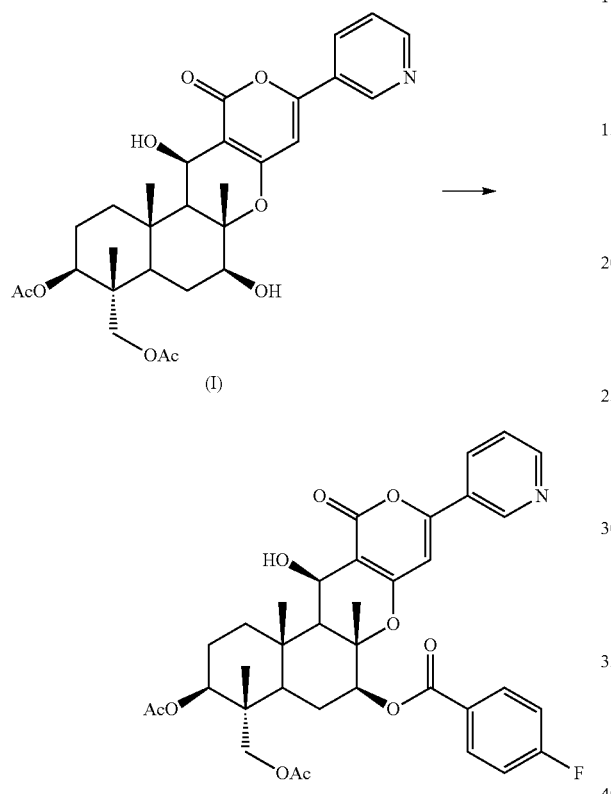

In the same manner as in Example 2, PRD 020 (9.2 mg, 75%) was obtained as a white solid from compound I (10 mg, 18.5 μmol).

$^1$H NMR (CDCl$_3$, 300 MHz) δ 8.90 (d, 1H, H-2", J=2.1 Hz), 8.59 (dd, 1H, H-6", J=1.5, 4.8 Hz), 8.08-8.04 (m, 2H, H—Ar), 8.01-7.97 (m, 1H, H-4"), 7.30 (dd, 1H, H-5", J=4.8, 8.1 Hz), 7.12-7.07 (m, 2H, H—Ar), 6.35 (s, 1H, H-5'), 5.18 (dd, 1H, H-7, J=5.1, 10.8 Hz), 4.97-4.95 (m, 1H, H-13), 4.75 (dd, 1H, H-1, J=5.1, 11.4 Hz), 3.76 (d, 1H, H-11a, J=12.0 Hz), 3.63 (d, 1H, H-11b, J=12.0 Hz), 2.91 (br d, 1H, OH-13, J=1.5 Hz), 2.15-1.42 (m, 8H, H-2, 3, 5, 8, 9), 2.06 (s, 3H, Ac), 1.98 (s, 3H, Ac), 1.77 (s, 3H, Me), 1.42 (s, 3H, Me), 0.84 (s, 3H, Me).

$^{13}$C NMR (CDCl$_3$, 150 MHz) δ 170.94, 170.52, 166.78, 165.09, 164.49, 163.96, 162.15, 157.40, 151.58, 146.82, 134.07, 132.94, 132.32, 132.25, 127.09, 126.37, 123.60, 116.68 (J=22.1 Hz), 102.95, 99.35, 83.34, 78.45, 73.53, 64.87, 60.25, 54.78, 45.44, 40.39, 37.91, 36.17, 25.33, 22.71, 21.13, 20.85, 17.51, 16.54, 13.22.

FAB-LRMS m/z 664 (MH$^+$); FAB-HRMS (CHCl$_3$) calcd. for C$_{36}$H$_{39}$FNO$_{10}$ 664.2558 (MH$^+$). found 664.2589 (MH$^+$).

Example 25

Preparation of
7-p-ethylbenzoyl-7-deacetylpyripyropene A (PRD 025)

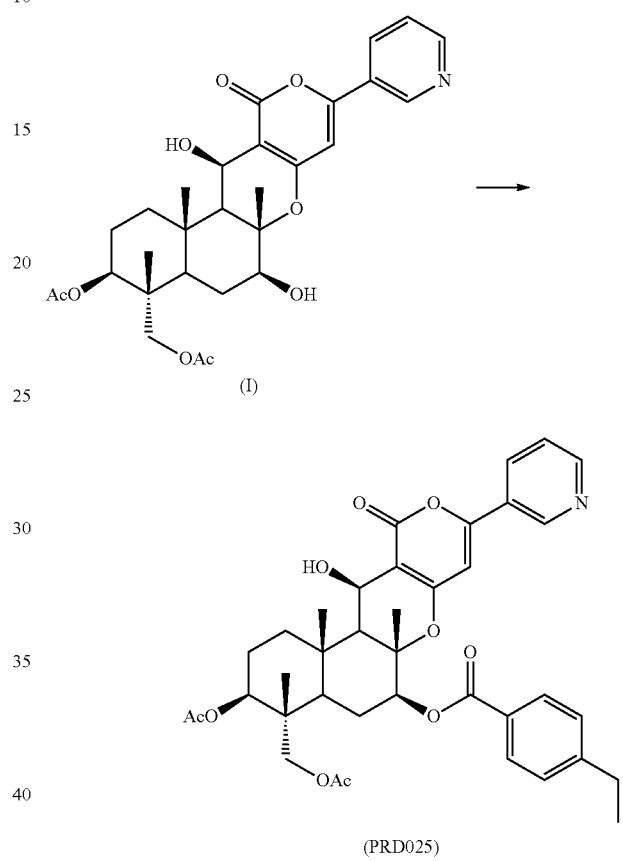

In the same manner as in Example 2, PRD 025 (11.7 mg, 94%) was obtained as a white solid from compound I (10 mg, 18.5 μmol).

$^1$H NMR (CDCl$_3$, 300 MHz) δ 8.90 (dd, 1H, H-2", J=0.9, 2.4 Hz), 8.59 (dd, 1H, H-6", J=1.5, 4.8 Hz), 8.01-7.95 (m, 3H, H-4", Ar), 7.33-7.19 (m, 3H, H-5", Ar), 6.35 (s, 1H, H-5'), 5.20 (dd, 1H, H-7, J=5.4, 11.1 Hz), 4.97-4.96 (m, 1H, H-13), 4.74 (dd, 1H, H-1, J=5.1, 11.1 Hz), 3.79 (d, 1H, H-11a, J=12.0 Hz), 3.61 (d, 1H, H-11b, J=12.0 Hz), 2.89 (br d, 1H, OH-13, J=1.5 Hz), 2.15-1.39 (m, 10H, H-2, 3, 5, 8, 9, CH$_2$CH$_3$), 2.06 (s, 3H, Ac), 1.98 (s, 3H, Ac), 1.78 (s, 3H, Me), 1.42 (s, 3H, Me), 1.20 (s, 3H, H—CH$_2$CH$_3$), 0.84 (s, 3H, Me).

$^{13}$C NMR (CDCl$_3$, 150 MHz) δ 170.94, 170.52, 165.48, 163.98, 162.23, 157.33, 151.55, 150.25, 146.82, 132.94, 129.88, 128.04, 127.61, 127.13, 125.19, 123.59, 102.92, 99.43, 83.47, 78.00, 73.54, 64.88, 60.31, 54.79, 45.47, 40.40, 37.91, 36.18, 29.00, 26.74, 25.37, 22.73, 21.13, 20.86, 17.52, 16.54, 15.29, 13.21.

FAB-LRMS m/z 674 (MH$^+$); FAB-HRMS (CHCl$_3$) calcd. for C$_{38}$H$_{44}$NO$_{10}$ 674.2965 (MH$^+$). found 674.2955 (MH$^+$).

Example 26

Preparation of 7-p-nitrobenzoyl-7-deacetylpyripyropene A (PRD 029)

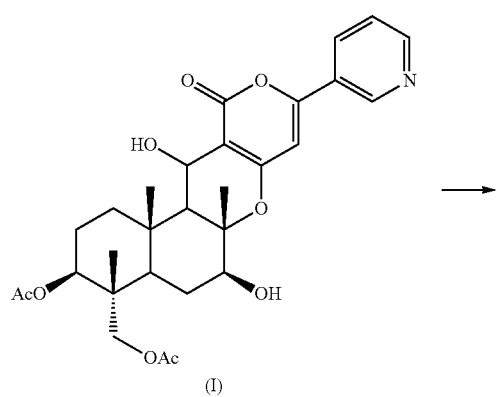

(I)

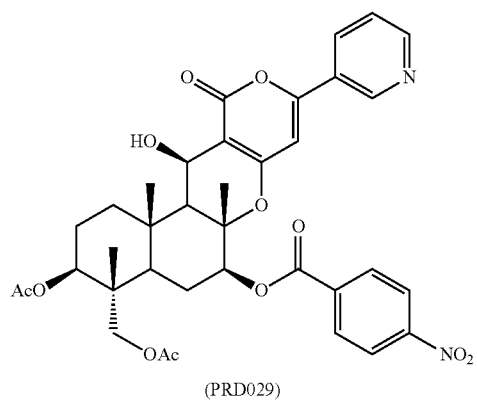

(PRD029)

In the same manner as in Example 2, PRD 029 (11.1 mg, 87%) was obtained as a white solid from compound I (10 mg, 18.5 μmol).

$^1$H NMR (CDCl$_3$, 300 MHz) δ 8.95 (d, 1H, H-2", J=1.5 Hz), 8.59 (dd, 1H, H-6", J=1.5, 5.1 Hz), 8.29-8.19 (m, 4H, H—Ar), 8.02-7.98 (m, 1H, H-4"), 7.34-7.30 (m, 1H, H-5"), 6.34 (s, 1H, H-5'), 5.22 (dd, 1H, H-7, J=5.4, 11.7 Hz), 4.97 (d, 1H, H-13, J=3.9 Hz), 4.76 (dd, 1H, H-1, J=5.1, 11.4 Hz), 3.75 (d, 1H, H-11a, J=12.0 Hz), 3.66 (d, 1H, H-11b, J=12.0 Hz), 2.94 (br s, 1H, OH-13), 2.16-1.42 (m, 8H, H-2, 3, 5, 8, 9), 2.07 (s, 3H, Ac), 1.99 (s, 3H, Ac), 1.80 (s, 3H, Me), 1.44 (s, 3H, Me), 0.85 (s, 3H, Me).

$^{13}$C NMR (CDCl$_3$, 150 MHz) δ 170.89, 170.50, 163.62, 161.85, 160.30, 150.73, 148.74, 135.42, 130.86, 123.67, 99.74, 83.28, 79.41, 73.48, 64.85, 60.16, 54.76, 49.72, 45.47, 40.40, 37.94, 36.15, 33.11, 29.67, 25.25, 22.70, 21.12, 20.84, 18.43, 17.51, 16.58, 13.25.

FAB-LRMS m/z 691 (MH$^+$); FAB-HRMS (CHCl$_3$) calcd. for C$_{36}$H$_{39}$N$_2$O$_{12}$ 691.2503 (MH$^+$). found 691.2510 (MH$^+$).

Example 27

Preparation of 7-o-4-carbamoylbenzyl-7-deacetylpyripyropene A (PRD 111)

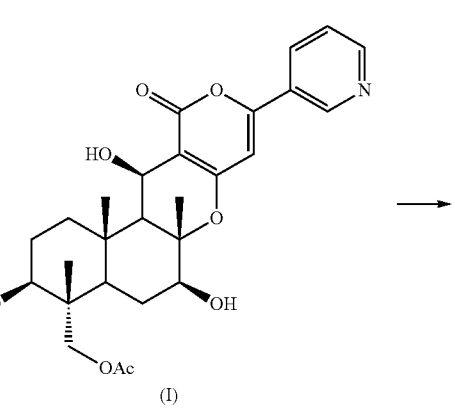

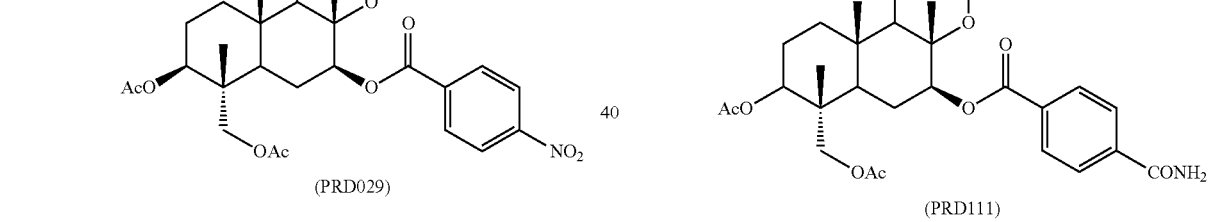

(PRD111)

In the same manner as in Example 2, PRD 111 (7.8 mg, 42%) was obtained as a white solid from compound I (15 mg, 27.5 μmol).

$^1$H NMR (CDCl$_3$, 400 MHz) δ 8.97 (d, 1H, H-2", J=2.0 Hz), 8.67 (dd, 1H, H-6", J=1.2, 3.2 Hz), 8.18 (d, 1H, H—Ar, J=8.4 Hz), 8.08-8.06 (m, 1H, H-4"), 7.93 (d, 1H, H—Ar, J=8.4 Hz), 7.40-7.36 (m, 1H, H-5"), 6.42 (s, 1H, H-5'), 6.19 (br s, 1H, ½NH$_2$), 5.82 (br s, 1H, ½NH$_2$), 5.28 (dd, 1H, H-7, J=4.8, 11.2 Hz), 5.04 (s, 1H, H-13), 4.82 (dd, 1H, H-1, J=4.8, 11.2 Hz), 3.84 (d, 1H, H-11a, J=12.0 Hz), 3.72 (d, 1H, H-11b, J=12.0 Hz), 3.02 (br s, 1H, OH-13), 2.23-1.21 (m, 8H, H-2, 3, 5, 8, 9), 2.14 (s, 3H, Ac), 2.05 (s, 3H, Ac), 1.86 (s, 3H, Me), 1.50 (s, 3H, Me), 0.91 (s, 3H, Me).

ESI-LRMS m/z 711 (M+Na$^+$); ESI-HRMS (MeOH) calcd. for C$_{37}$H$_{40}$N$_2$NaO$_{11}$ 711.2530 (M+Na$^+$). found 711.2545 (M+Na$^+$).

Example 28

Preparation of 7-benzoyl-7-deacetylpyripyropene A (PRD 027)

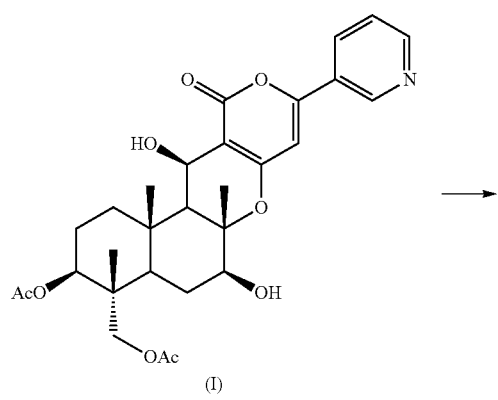

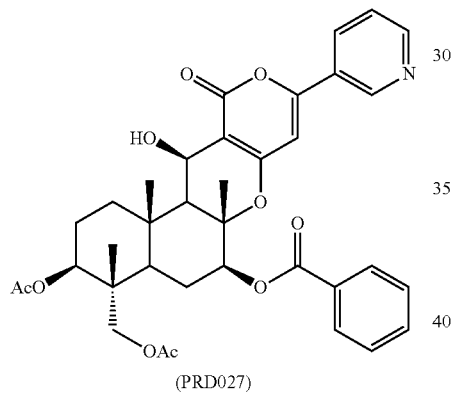

(PRD027)

In the same manner as in Example 2, PRD 027 (11.8 mg, 99%) was obtained as a white solid from compound I (10 mg, 18.5 μmol).

$^1$H NMR (CDCl$_3$, 300 MHz) δ 8.96 (d, 1H, H-2", J=2.1 Hz), 8.65 (dd, 1H, H-6", J=1.2, 4.8 Hz), 8.13-8.04 (m, 3H, H-4", Ar), 7.64-7.58 (m, 1H, H—Ar), 7.52-7.47 (m, 2H, H—Ar), 7.39-7.35 (m, 1H, H-5"), 6.42 (s, 1H, H-5'), 5.27 (dd, 1H, H-7, J=5.4, 11.4 Hz), 5.03 (d, 1H, H-13, J=3.3 Hz), 4.81 (dd, 1H, H-1, J=5.1, 11.4 Hz), 3.85 (d, 1H, H-11a, J=12.0 Hz), 3.69 (d, 1H, H-11b, J=12.0 Hz), 2.99 (br s, 1H, OH-13), 2.22-1.41 (m, 8H, H-2, 3, 5, 8, 9), 2.13 (s, 3H, Ac), 2.05 (s, 3H, Ac), 1.85 (s, 3H, Me), 1.49 (s, 3H, Me), 0.90 (s, 3H, Me).

$^{13}$C NMR (CDCl$_3$, 150 MHz) δ 170.15, 170.73, 165.65, 164.19, 162.42, 157.57, 151.76, 147.03, 133.49, 133.18, 130.36, 129.96, 128.72, 127.35, 123.83, 103.16, 99.63, 83.64, 78.47, 73.76, 65.10, 60.50, 55.00, 45.68, 40.62, 38.13, 36.39, 29.89, 25.56, 22.94, 21.35, 21.14, 21.08, 17.74, 16.76, 13.44.

FAB-LRMS m/z 646 (MH$^+$), FAB-HRMS (CHCl$_3$) calcd. for C$_{36}$H$_{40}$NO$_{10}$ 646.2652 (MH$^+$). found 646.2660 (MH$^+$).

Example 29

Preparation of 7-O-p-azidebenzoyl-7-deacetylpyripyropene A (PRD 030)

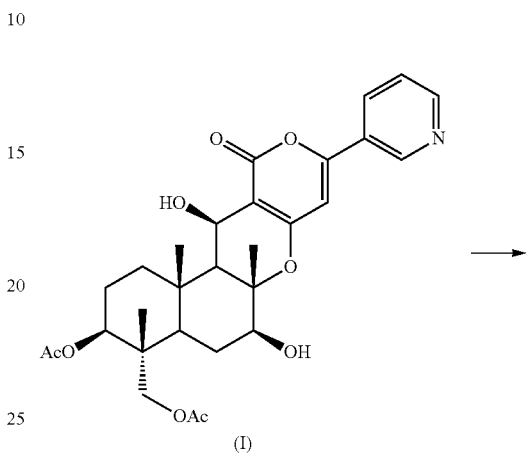

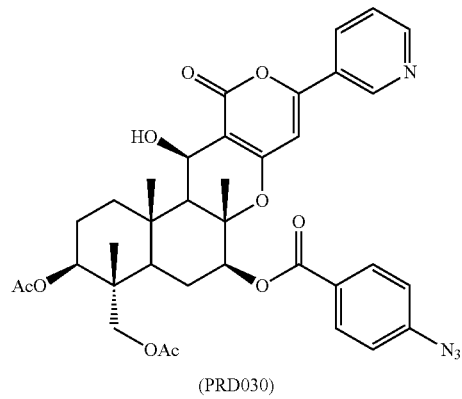

(PRD030)

In the same manner as in Example 2, PRD 030 (32.3 mg, 85%) was obtained as a white solid from compound I (30 mg, 55.4 μmol).

$^1$H NMR (CDCl$_3$, 300 MHz) δ 8.96 (d, 1H, H-2", J=1.5 Hz), 8.66 (dd, 1H, H-6", J=1.5, 4.8 Hz), 8.10 (d, 2H, H—Ar, J=8.7 Hz), 8.06-8.05 (m, 1H, H-4"), 7.38 (dd, 1H, H-5", J=4.5, 7.8 Hz), 7.12 (d, 2H, H—Ar, J=8.7 Hz), 6.42 (s, 1H, H-5'), 5.25 (dd, 1H, H-7, J=4.8, 10.8 Hz), 5.04 (s, 1H, H-13), 4.82 (dd, 1H, H-1, J=4.8, 11.1 Hz), 3.84 (d, 1H, H-11a, J=12.0 Hz), 3.70 (d, 1H, H-11b, J=12.0 Hz), 3.06 (br s, 1H, OH-13), 2.22-1.26 (m, 8H, H-2, 3, 5, 8, 9), 2.13 (s, 3H, Ac), 2.05 (s, 3H, Ac), 1.85 (s, 3H, Me), 1.50 (s, 3H, Me), 0.91 (s, 3H, Me).

$^{13}$C NMR (CDCl$_3$, 150 MHz) δ 170.89, 170.47, 164.58, 163.87, 162.12, 157.30, 151.50, 146.75, 145.08, 132.88, 131.52, 127.04, 126.55, 123.55, 118.89, 102.93, 99.31, 83.31, 78.34, 73.49, 64.82, 50.15, 54.71, 45.39, 40.35, 37.86, 36.12, 25.30, 22.67, 21.09, 20.82, 17.46, 16.52, 13.28.

FAB-LRMS m/z 687 (MH$^+$); FAB-HRMS (CHCl$_3$) calcd. for C$_{36}$H$_{39}$N$_4$O$_{10}$ 687.2666 (MH$^+$). found 687.2659 (MH$^+$).

Example 30

Preparation of 7-p-aminobenzoyl-7-deacetylpyripyropene A (PRD 032)

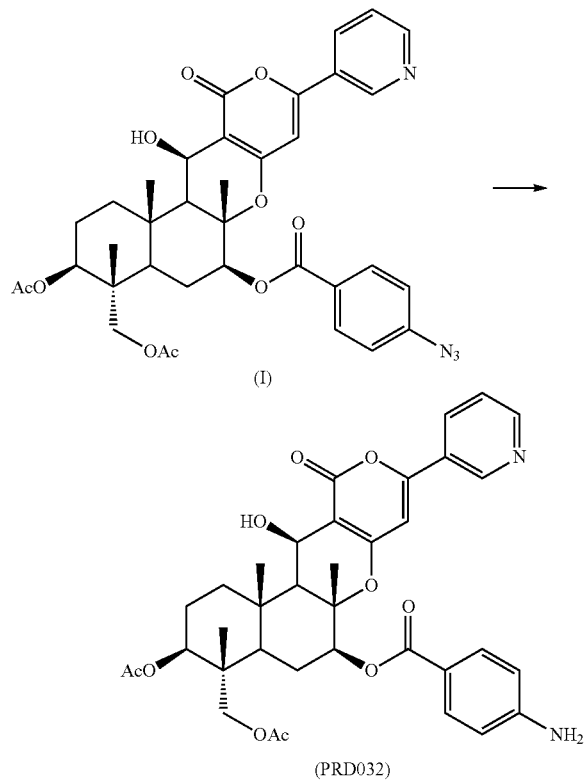

To a solution of compound I (13 mg, 24.0 μmol) in THF/H₂O 1:1 (0.5 mL), Me₃P (1.0 M sol. in toluene, 29 mL, 28.8 μmol) was added and stirred for 5 minutes at room temperature. The reaction mixture was concentrated at a reduced pressure, and the resulting residue was purified by neutral flash silica gel column chromatography (1×5, MeOH in CH₂Cl₂ 2%) to give PRD 032 (7.8 mg, 49%) as a white solid.

$^1$H NMR (CDCl₃, 300 MHz) δ 8.97 (dd, 1H, H-2", J=0.6, 2.1 Hz), 8.66 (dd, 1H, H-6", J=1.5, 4.8 Hz), 8.08-8.04 (m, 1H, H-4"), 7.92 (d, 2H, H—Ar, J=8.8 Hz), 7.40-7.35 (m, 1H, H-5"), 6.69 (d, 2H, H—Ar, J=8.8 Hz), 6.43 (s, 1H, H-5'), 5.24 (dd, 1H, H-7, J=4.2, 10.2 Hz), 5.02 (dd, 1H, H-13, J=1.5, 3.9 Hz), 4.80 (dd, 1H, H-1, J=5.4, 11.4 Hz), 4.12 (br s, 2H, NH₂), 3.86 (d, 1H, H-11a, J=12.0 Hz), 3.67 (d, 1H, H-11b, J=12.0 Hz), 2.92 (br s, 1H, OH-13), 2.21-1.41 (m, 8H, H-2, 3, 5, 8, 9), 2.12 (s, 3H, Ac), 2.05 (s, 3H, Ac), 1.85 (s, 3H, Me), 1.48 (s, 3H, Me), 0.90 (s, 3H, Me).

$^{13}$C NMR (CDCl₃, 150 MHz) δ 170.99, 170.54, 165.42, 164.05, 162.34, 157.28, 151.51, 151.12, 146.82, 132.92, 131.81, 127.14, 123.59, 119.53, 113.81, 102.90, 99.53, 83.58, 77.45, 73.57, 64.89, 60.32, 59.02, 54.77, 45.57, 45.45, 40.40, 40.17, 37.90, 36.18, 25.45, 22.74, 21.13, 20.87, 17.52, 16.55, 13.19.

FAB-LRMS m/z 661 (MH⁺); FAB-HRMS (CHCl₃) calcd. for C₃₆H₄₁N₂O₁₀ 661.2761 (MH⁺). found 661.2781 (MH⁺).

Example 31

Preparation of 7-p-hydroxybenzoyl-7-deacetylpyripyropene A (PRD 031)

a) Preparation of 4-(triisopropylsilyloxy)benzoic acid

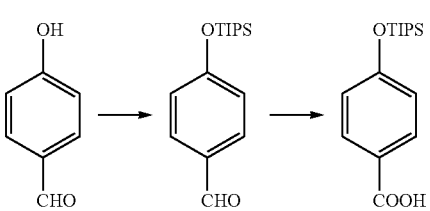

In an argon atmosphere, TIPSCl (318 μL, 1.50 mmol) and imidazole (204 mg, 3.00 mmol) were added to a solution of 4-hydroxybenzaldehyde (122 mg, 1.00 mmol) in THF (10 mL) and stirred for 5.5 hours at room temperature. To the reaction mixture, MeOH was added to stop the reaction and then EtOAc was added for dilution. The solution was washed with water and dried over anhydrous sodium sulfate. The solution was filtered, and the filtrate was concentrated at a reduced pressure. The resulting residue was semi-purified by neutral flash silica gel chromatography (3×5, hexane:EtOAc=15:1), and fractions containing the desired product were concentrated at a reduced pressure to give a white foam.

The thus-obtained foam was dissolved in a solution of tBuOH/H₂O 1:1 (10 mL). To the resulting solution, NaClO₂ (271 mg, 3.00 mmol), NaHPO₄.2H₂O (468 mg, 3.00 mmol), and 2-methyl-2-butene (424 μL, 4.00 mmol) were added and stirred for 48 hours at room temperature. The reaction mixture was diluted with EtOAc, and the organic layer was washed three times with water and dried over anhydrous sodium sulfate. The solution was filtered, and the filtrate was concentrated at a reduced pressure. The resulting residue was purified by neutral flash silica gel chromatography (2.5×10, hexane:EtOAc=13:1-7:1) to give 4-(triisopropylsilyloxy)benzoic acid (269 mg, 2 steps 92%) as a white solid.

b) Preparation of 7-p-(triisopropylsilyloxy)benzoyl-7-deacetylpyripyropene A

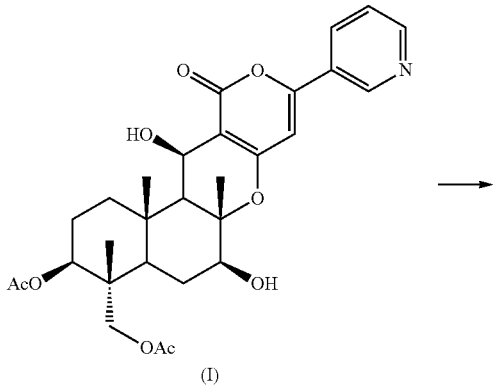

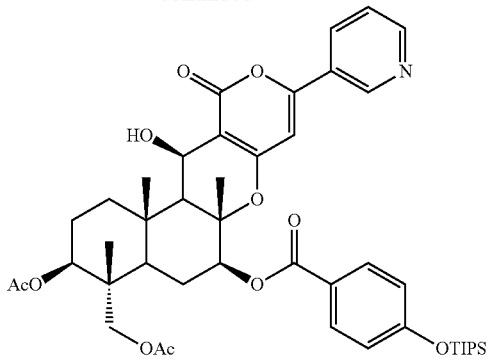

In an argon atmosphere, EDCI (28.4 mg, 148 μmol), 4-(triisopropylsilyloxy)benzoic acid (21.8 mg, 74.0 μmol), and DMAP (2.3 mg, 18.5 μmol) were added to a solution of compound I (10 mg, 18.5 μmol) in $CH_2Cl_2$ (0.5 mL) and stirred for 13 hours at room temperature. The reaction mixture was diluted with EtOAc, and the organic layer was washed with 1N HCl and water and dried over anhydrous sodium sulfate. The solution was filtered, and the filtrate was concentrated at a reduced pressure. The resulting residue was purified by neutral flash silica gel chromatography (1×5, MeOH in $CH_2Cl_2$ 0.5-2%) to give 7-p-(triisopropylsilyloxy)benzoyl-7-deacetylpyripyropene A (9.8 mg, 65%) as a white solid.

$^1$H NMR (CDCl$_3$, 300 MHz) δ 8.96 (d, 1H, H-2", J=1.5 Hz), 8.66 (dd, 1H, H-6", J=1.5, 4.8 Hz), 8.10 (d, 2H, H—Ar, J=8.7 Hz), 8.06-8.05 (m, 1H, H-4"), 7.38 (dd, 1H, H-5", J=4.5, 7.8 Hz), 7.12 (d, 2H, H—Ar, J=8.7 Hz), 6.42 (s, 1H, H-5), 5.25 (dd, 1H, H-7, J=4.8, 10.8 Hz), 5.04 (s, 1H, H-13), 4.82 (dd, 1H, H-1, J=4.8, 11.1 Hz), 3.84 (d, 1H, H-11a, J=12.0 Hz), 3.70 (d, 1H, H-11b, J=12.0 Hz), 3.06 (br s, 1H, OH-13), 2.22-1.26 (m, 29H, H-2, 3, 5, 8, 9, TIPS), 2.13 (s, 3H, Ac), 2.05 (s, 3H, Ac), 1.85 (s, 3H, Me), 1.50 (s, 3H, Me), 0.91 (s, 3H, Me).

$^{13}$C NMR (CDCl$_3$, 150 MHz) δ 170.96, 170.53, 165.20, 164.02, 162.29, 160.79, 157.30, 151.51, 146.80, 132.95, 131.72, 127.13, 123.60, 122.74, 119.74, 102.92, 99.49, 83.49, 77.84, 77.28, 75.55, 64.87, 60.30, 54.78, 45.42, 40.39, 37.90, 36.18, 29.68, 25.40, 22.73, 21.14, 20.87, 17.85, 17.51, 16.54, 13.20.

FAB-LRMS m/z 818 (MH$^+$); FAB-HRMS (CHCl$_3$) calcd. for $C_{45}H_{60}NO_{11}Si$ 818.3936 (MH$^+$). found 818.3937 (MB).

c) Preparation of 7-p-hydroxybenzoyl-7-deacetylpyripyropene A (PRD 031)

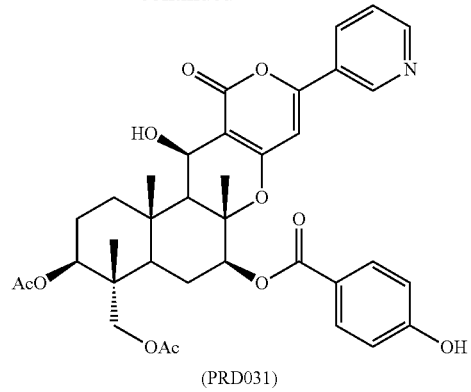

(PRD031)

TBAF (1.0 M sol. in THF, 23 mL, 22.8 μmol) and AcOH (1.3 μL, 22.8 μmol) were added to a solution of 7-p-(triisopropylsilyloxy)benzoyl-7-deacetylpyripyropene A (9.8 mg, 12.0 μmol) in THF (0.5 mL) and stirred for 5 minutes at 0° C. The reaction mixture was concentrated at a reduced pressure and the resulting residue was purified by neutral flash silica gel chromatography (1×5, MeOH in $CH_2Cl_2$ 0-3%) to give PRD 031 (5.7 mg, 72%) as a white solid.

$^1$H NMR (CDCl$_3$, 300 MHz) δ 9.15 (brs, 1H, H—Ar—OH), 8.96 (d, 1H, H-2", J=2.1 Hz), 8.66 (dd, 1H, H-6", J=1.8, 5.1 Hz), 8.24-8.19 (m, 1H, H-4"), 7.94 (d, 2H, H—Ar, J=6.9 Hz), 7.48 (dd, 1H, H-5", J=5.1, 8.4 Hz), 6.88 (d, 2H, H—Ar, J=6.9 Hz), 6.50 (s, 1H, H-5'), 5.23 (dd, 1H, H-7, J=4.8, 10.2 Hz), 5.01 (d, 1H, H-13, J=6.9 Hz), 4.82 (dd, 1H, H-1, J=5.1, 11.2 Hz), 3.85 (d, 1H, H-11a, J=12.0 Hz), 3.68 (d, 1H, H-11b, J=12.0 Hz), 2.98 (br s, 1H, OH-13), 2.21-1.41 (m, 8H, H-2, 3, 5, 8, 9), 2.13 (s, 3H, Ac), 2.05 (s, 3H, Ac), 1.83 (s, 3H, Me), 1.48 (s, 3H, Me), 0.90 (s, 3H, Me).

$^{13}$C NMR (CDCl$_3$, 300 MHz) δ 171.18, 170.66, 165.22, 163.90, 162.24, 161.60, 156.52, 150.47, 145.82, 133.90, 132.71, 131.99, 127.76, 124.28, 121.50, 115.37, 103.11, 99.72, 83.56, 77.71, 73.57, 64.89, 60.18, 54.60, 45.40, 40.37, 37.89, 36.12, 25.34, 22.69, 21.15, 20.86, 17.51, 16.57, 13.20.

FAB-LRMS m/z 662 (MH$^+$); FAB-HRMS (CHCl$_3$) calcd. for $C_{36}H_{40}NO_{10}$ 662.2601 (MH$^+$). found 662.2610 (MH$^+$).

Example 32

Preparation of 7-O-p-bromo-m-fluorobenzoyl-7-deacetylpyripyropene A (PRD 105)

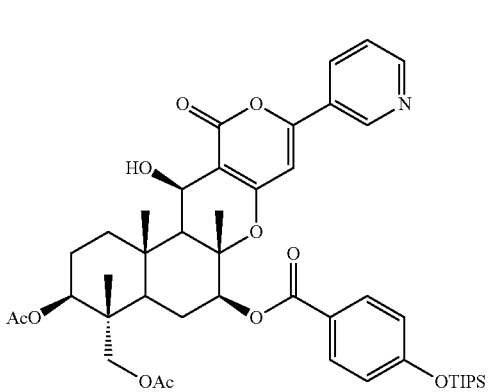

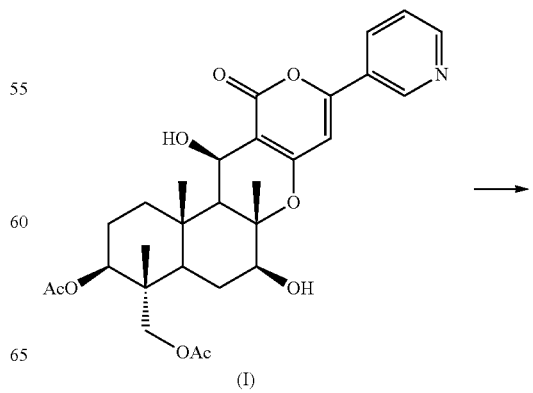

(I)

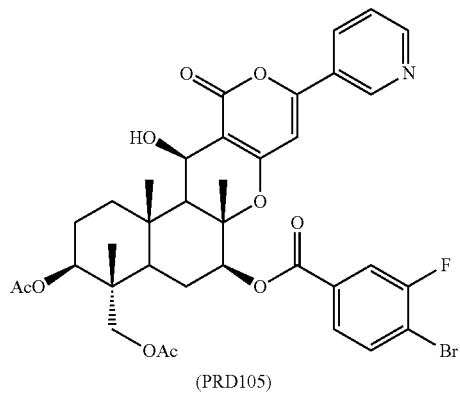

(PRD105)

In the same manner as in Example 2, PRD 105 (18.3 mg, 90%) was obtained as a white solid from compound I (15 mg, 27.5 μmol).

$^1$H NMR (CDCl$_3$, 400 MHz) δ 8.97 (d, 1H, H-2", J=2.4 Hz), 8.67 (dd, 1H, H-6", J=1.6, 4.8 Hz), 8.08-8.05 (m, 1H, H-4"), 7.83-7.76 (m, 2H, H—Ar), 7.71-7.68 (m, 1H, H—Ar), 7.40-7.36 (m, 1H, H-5"), 6.41 (s, 1H, H-5'), 5.25 (dd, 1H, H-7, J=5.2, 11.6 Hz), 5.04-5.03 (m, 1H, H-13), 4.82 (dd, 1H, H-1, J=5.2, 11.6 Hz), 3.83 (d, 1H, H-11a, J=12.0 Hz), 3.72 (d, 1H, H-11b, J=12.0 Hz), 3.00 (br d, 1H, OH-13, J=2.0 Hz), 2.19-1.26 (m, 8H, H-2, 3, 5, 8, 9), 2.13 (s, 3H, Ac), 2.05 (s, 3H, Ac), 1.84 (s, 3H, Me), 1.62 (s, 3H, Me), 0.91 (s, 3H, Me).

ESI-LRMS m/z 742.2 (MH$^+$). ESI-HRMS (MeOH) calcd. for C$_{36}$H$_{38}$BrFNO$_{10}$ 742.1663 (MH$^+$). found 742.1663 (MH$^+$).

Example 33

Preparation of 7-O-p-bromo-o-fluorobenzoyl-7-deacetylpyripyropene A (PRD 109)

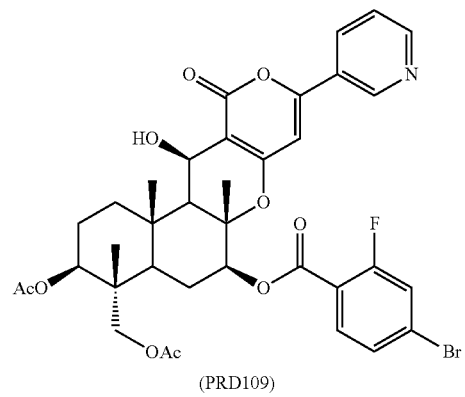

(PRD109)

In the same manner as in Example 2, PRD 109 (19.0 mg, 93%) was obtained as a white solid from compound I (15 mg, 27.5 μmol).

$^1$H NMR (CDCl$_3$, 300 MHz) δ 8.98 (dd, 1H, H-2", J=0.6, 1.8 Hz), 8.67 (dd, 1H, H-6", J=1.5, 4.8 Hz), 8.10-8.06 (m, 1H, H-4"), 7.91 (dd, 1H, H—Ar, J=1.8, 2.1 Hz), 7.44-7.37 (m, 3H, H-5", Ar), 6.44 (s, 1H, H-5'), 5.26 (dd, 1H, H-7, J=5.1, 11.1 Hz), 5.03 (d, 1H, H-13, J=4.2 Hz), 4.82 (dd, 1H, H-1, J=5.1, 11.1 Hz), 3.85 (d, 1H, H-11a, J=12.0 Hz), 3.71 (d, 1H, H-11b, J=12.0 Hz), 2.98 (br s 1H, OH-13), 2.22-1.25 (m, 8H, H-2, 3, 5, 8, 9), 2.13 (s, 3H, Ac), 2.05 (s, 3H, Ac), 1.81 (s, 3H, Me), 1.49 (s, 3H, Me), 0.91 (s, 3H, Me).

$^{13}$C NMR (CDCl$_3$, 75 MHz) δ 170.95, 170.53, 163.95, 163.45, 162.92, 162.15, 159.93, 157.35, 151.50, 146.75, 133.41, 133.03, 128.433, 127.69, 127.14, 123.65, 121.01, 117.64, 102.99, 99.38, 83.22, 79.23, 73.53, 64.88, 60.21, 54.72, 45.48, 40.40, 37.92, 36.16, 25.22, 22.72, 20.87, 17.52, 16.50, 13.25.

ESI-LRMS m/z 764 (M+Na$^+$). ESI-HRMS (MeOH) calcd. for C$_{36}$H$_{37}$BrFNNaO$_{10}$ 764.1483 (M+Na$^+$). found 764.1445 (M+Na$^+$).

Example 34

Preparation of 7-O-o,m,p-trifluorobenzoyl-7-deacetylpyripyropene A (PRD 110)

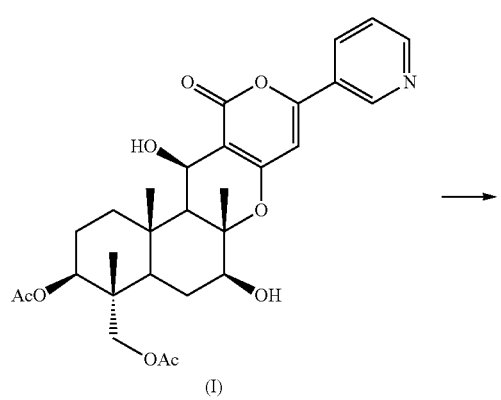

(I)

→

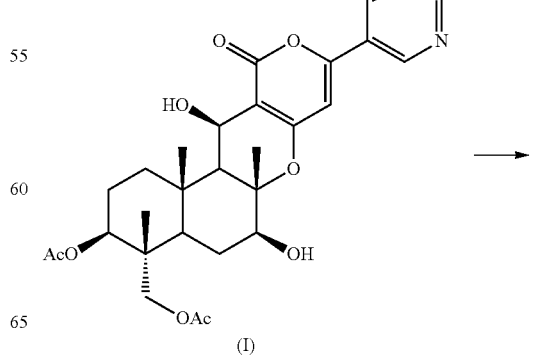

(I)

→

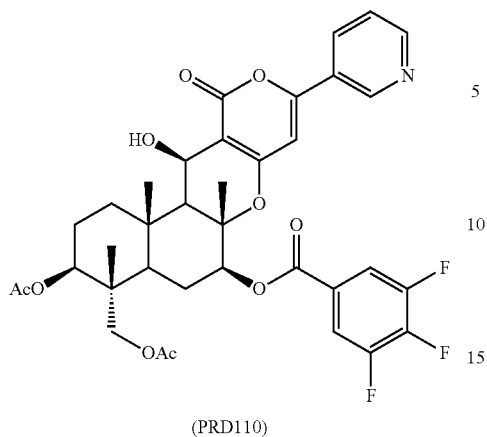

(PRD110)

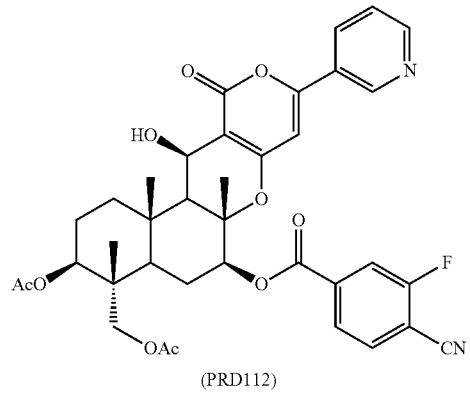

(PRD112)

In the same manner as in Example 2, PRD 110 (17.0 mg, quant.) was obtained as a white solid from compound I (15 mg, 27.5 μmol).

$^1$H NMR (CDCl$_3$, 300 MHz) δ 8.97 (dd, 1H, H-2", J=0.6, 2.4 Hz), 8.67 (dd, 1H, H-6", J=1.5, 4.8 Hz), 8.10-8.06 (m, 1H, H-4"), 7.77-7.72 (m, 2H, H—Ar), 7.42-7.37 (m, 1H, H-5"), 6.41 (s, 1H, H-5'), 5.23 (dd, 1H, H-7, J=5.1, 11.4 Hz), 5.03 (d, 1H, H-13, J=4.2 Hz), 4.82 (dd, 1H, H-1, J=5.4, 11.1 Hz), 3.81 (d, 1H, H-11a, J=12.0 Hz), 3.72 (d, 1H, H-11b, J=12.0 Hz), 3.01 (br s, 1H, OH-13), 2.23-1.25 (m, 8H, H-2, 3, 5, 8, 9), 2.13 (s, 3H, Ac), 2.05 (s, 3H, Ac), 1.84 (s, 3H, Me), 1.50 (s, 3H, Me), 0.91 (s, 3H, Me).

$^{13}$C NMR (CDCl$_3$, 75 MHz) δ 170.91, 170.52, 163.88, 161.99, 157.44, 151.54, 146.73, 133.04, 127.09, 123.68, 114.50, 114.40, 114.20, 103.02, 99.24, 83.14, 83.13, 79.45, 73.49, 64.85, 60.16, 54.74, 45.44, 40.40, 37.92, 37.92, 37.91, 36.15, 25.25, 22.71, 21.15, 20.85, 17.51, 26.55, 13.26.

ESI-LRMS m/z 700 (MH$^+$). ESI-HRMS (MeOH) calcd. for C$_{36}$H$_{37}$F$_3$NO$_{10}$ 700.2370 (MH$^+$). found 674.2331 (MH$^+$).

Example 35

Preparation of
7-O-p-cyano-m-fluorobenzoyl-7-deacetylpyripyropene A (PRD 112)

In the same manner as in Example 2, PRD 112 (18.9 mg, quant.) was obtained as a white solid from compound I (15 mg, 27.5 μmol).

$^1$H NMR (CDCl$_3$, 400 MHz) δ 8.92 (dd, 1H, H-2", J=0.8, 2.0 Hz), 8.67 (dd, 1H, H-6", J=1.5, 4.8 Hz), 8.08-8.05 (m, 1H, H-4"), 7.83-7.76 (m, 1H, H—Ar), 7.71-7.68 (m, 2H, H—Ar), 7.40-7.36 (m, 1H, H-5"), 6.41 (s, 1H, H-5'), 5.24 (dd, 1H, H-7, J=5.2, 11.6 Hz), 5.03 (d, 1H, H-13, J=4.0 Hz), 4.82 (dd, 1H, H-1, J=4.8, 11.6 Hz), 3.83 (d, 1H, H-11a, J=12.0 Hz), 3.72 (d, 1H, H-11b, J=12.0 Hz), 3.04 (br s, 1H, OH-13), 2.22-1.24 (m, 8H, H-2, 3, 5, 8, 9), 2.10 (s, 3H, Ac), 2.05 (s, 3H, Ac), 1.71 (s, 3H, Me), 1.44 (s, 3H, Me), 0.89 (s, 3H, Me).

ESI-LRMS m/z 711 (M+Na$^+$). ESI-HRMS (MeOH) calcd. for C$_{37}$H$_{37}$FN$_2$NaO$_{10}$ 711.2330 (M+Na$^+$). found 711.2338 (M+Na$^+$).

Example 36

Preparation of
7-cyclohexanecarboxyl-7-deacetylpyripyropene A (PRD 021)

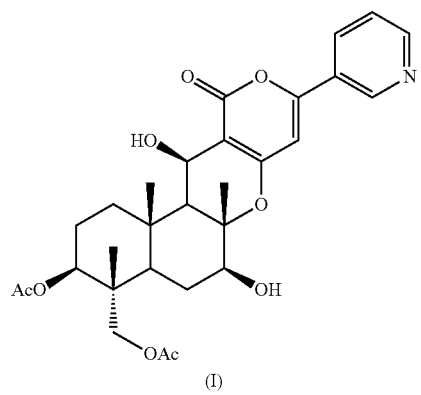

(I)

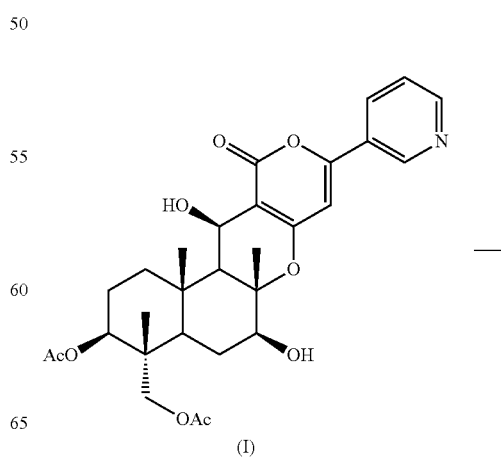

(I)

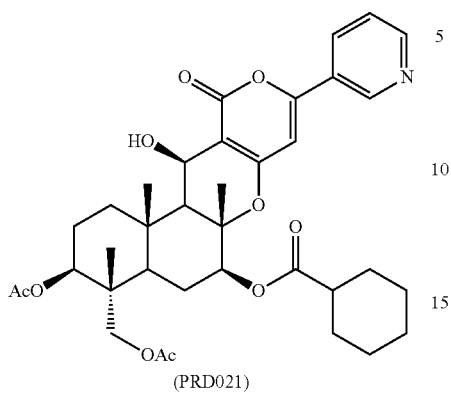
(PRD021)

In the same manner as in Example 2, PRD 021 (15.6 mg, 87%) was obtained as a white solid from compound I (15 mg, 27.7 μmol).

$^1$H NMR (CDCl$_3$, 300 MHz) δ 9.00 (dd, 1H, H-2", J=0.6, 2.1 Hz), 8.69 (dd, 1H, H-6", J=1.5, 4.8 Hz), 8.11-8.07 (m, 1H, H-4"), 7.43-7.38 (m, 1H, H-5"), 6.38 (s, 1H, H-5'), 5.02-4.99 (m, 2H, H-7, 13), 4.79 (dd, 1H, H-1, J=5.1, 11.1 Hz), 3.83 (d, 1H, H-11a, J=12.0 Hz), 3.66 (d, 1H, H-11b, J=12.0 Hz), 2.97 (br s, 1H, OH-13), 2.44-2.37 (m, 1H, cyclohexyl), 2.17-1.26 (m, 18H, H-2, 3, 5, 8, 9, cyclohexyl), 2.09 (s, 3H, Ac), 2.04 (s, 3H, Ac), 1.71 (s, 3H, Me), 1.54 (s, 3H, Me), 0.89 (s, 3H, Me).

$^{13}$C NMR (CDCl$_3$, 150 MHz) δ 170.94, 170.95, 170.49, 163.95, 162.16, 157.37, 151.57, 146.85, 132.98, 127.79, 127.15, 123.62, 102.89, 99.37, 83.44, 73.53, 64.87, 60.22, 54.69, 45.42, 43.37, 40.33, 37.86, 36.14, 29.15, 28.90, 25.74, 25.44, 25.34, 25.19, 22.69, 21.11, 20.81, 17.47, 16.35, 13.19.

FAB-LRMS m/z 652 (MH$^+$); FAB-HRMS (CHCl$_3$) calcd. for C$_{36}$H$_{46}$NO$_{10}$ 652.3122 (MH$^+$). found 652.3138 (MH$^+$).

Example 37

Preparation of 7-O-4-trans-methylcyclohexanecarboxyl-7-deacetylpyripyropene A (PRD 085)

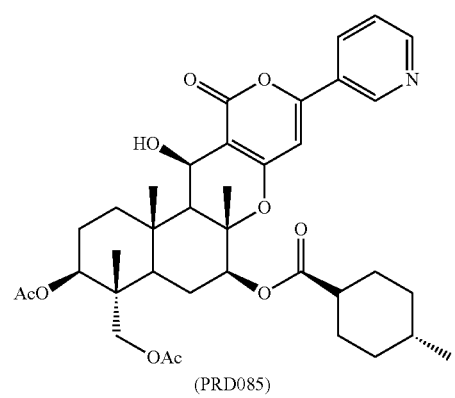
(PRD085)

In the same manner as in Example 2, PRD 085 (11.4 mg, 93%) was obtained as a white solid from compound I (10 mg, 18.5 μmol).

$^1$H NMR (CDCl$_3$, 300 MHz) δ 9.00 (dd, 1H, H-2", J=0.9, 2.1 Hz), 8.69 (dd, 1H, H-6", J=1.8, 5.1 Hz), 8.12-8.08 (m, 1H, H-4"), 7.44-7.39 (m, 1H, H-5"), 6.38 (s, 1H, H-5'), 5.02-4.99 (m, 2H, H-7, 13), 4.79 (dd, 1H, H-1, J=5.1, 11.1 Hz), 3.83 (d, 1H, H-11a, J=12.0 Hz), 3.66 (d, 1H, H-11b, J=12.0 Hz), 2.88 (br s, 1H, OH-13), 2.35-2.26 (m, 1H, COCH), 2.19-1.25 (m, 17H, H-2, 3, 5, 8, 9, cyclohexyl), 2.09 (s, 3H, Ac), 2.04 (s, 3H, Ac), 1.70 (s, 3H, Me), 1.44 (s, 3H, Me), 0.93-0.89 (m, 3H, Me).

ESI-LRMS m/z 688 (M+Na$^+$). ESI-HRMS (MeOH) calcd. for C$_{37}$H$_{47}$NNaO$_{10}$ 688.3098 (M+Na$^+$). found 688.3103 (M+Na$^+$).

Example 38

Preparation of 7-O-cyclopentanecarboxyl-7-deacetylpyripyropene A (PRD 075)

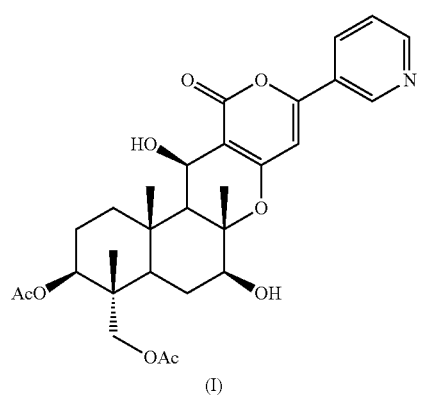
(I)

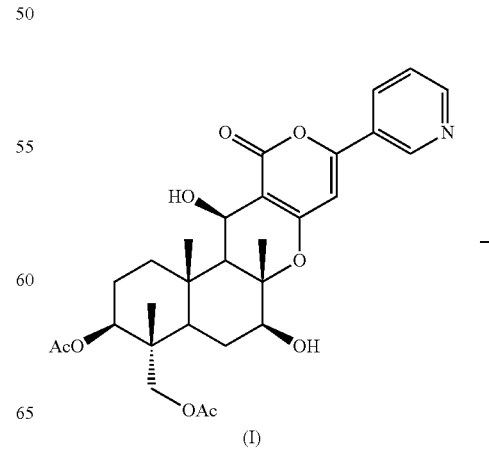
(I)

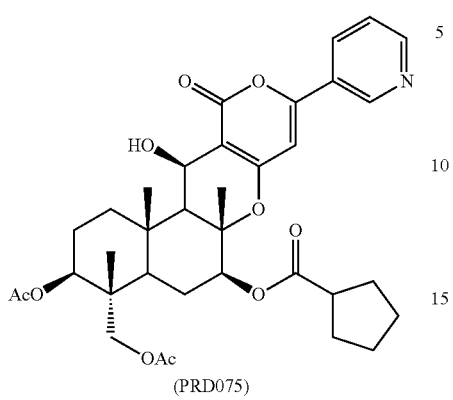

(PRD075)

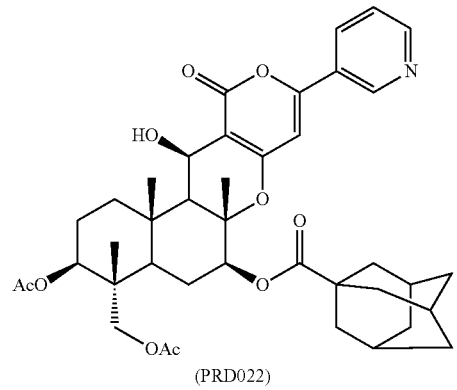

(PRD022)

In the same manner as in Example 2, PRD 075 (11.6 mg, 99%) was obtained as a white solid from compound I (10 mg, 18.5 mol).

$^1$H NMR (CDCl$_3$, 300 MHz) δ 9.00 (d, 1H, H-2", J=2.4 Hz), 8.69 (dd, 1H, H-6", J=1.5, 4.8 Hz), 8.11-8.07 (m, 1H, H-4"), 7.43-7.38 (m, 1H, H-5"), 6.38 (s, 1H, H-5'), 5.03-4.99 (m, 2H, H-7, 13), 4.79 (dd, 1H, H-1, J=4.8, 11.1 Hz), 3.83 (d, 1H, H-11a, J=12.0 Hz), 3.68 (d, 1H, H-11b, J=12.0 Hz), 2.92 (br s 1H, OH-13), 2.87-2.81 (m, 1H, COCH), 2.19-1.25 (m, 16H, H-2, 3, 5, 8, 9, cyclopentyl), 2.09 (s, 3H, Ac), 2.04 (s, 3H, Ac), 1.70 (s, 3H, Me), 1.44 (s, 3H, Me), 0.89 (s, 3H, Me).

ESI-LRMS m/z 660 (M+Na$^+$). ESI-HRMS (MeOH) calcd. for C$_{35}$H$_{43}$NNaO$_{10}$ 660.2785 (M+Na$^+$). found 660.2794 (M+Na$^+$).

In the same manner as in Example 2, PRD 022 (4.8 mg, 25%) was obtained as a white solid from compound I (15 mg, 27.7 μmol).

$^1$H NMR (CDCl$_3$, 300 MHz) δ 8.94 (dd, 1H, H-2", J=0.9, 2.7 Hz), 8.62 (dd, 1H, H-6", J=1.5, 4.8 Hz), 8.05-8.01 (m, 1H, H-4"), 7.36-7.32 (m, 1H, H-5"), 6.29 (s, 1H, H-5'), 4.93-4.92 (m, 2H, H-7, 13), 4.71 (dd, 1H, H-1, J=5.4, 11.4 Hz), 3.78 (d, 1H, H-11a, J=12.0 Hz), 3.57 (d, 1H, H-11b, J=12.0 Hz), 2.84 (br s, 1H, OH-13), 2.13-1.16 (m, 23H, H-2, 3, 5, 8, 9, adamantyl), 2.02 (s, 3H, Ac), 1.97 (s, 3H, Ac), 1.65 (s, 3H, Me), 1.38 (s, 3H, Me), 0.82 (s, 3H, Me).

$^{13}$C NMR (CDCl$_3$, 150 MHz) δ 176.53, 170.98, 170.51, 164.00, 162.20, 157.40, 151.59, 146.89, 133.06, 127.19, 123.65, 112.54, 102.86, 99.46, 83.59, 73.51, 64.89, 60.29, 54.69, 45.41, 41.08, 40.36, 38.92, 37.88, 36.49, 36.14, 30.91, 29.68, 27.92, 25.16, 22.70, 21.13, 20.85, 17.49, 16.42, 13.20.

FAB-LRMS m/z 704 (MH$^+$); FAB-HRMS (CHCl$_3$) calcd. for C$_{40}$H$_{50}$NO$_{10}$ 704.3435 (MH$^+$). found 704.3466 (MH$^+$).

Example 39

Preparation of
7-1-adamantanecarboxyl-7-deacetylpyripyropene A
(PRD 022)

Example 40

Preparation of
7-p-biphenyl-4-carboxyl-7-deacetylpyripyropene A
(PRD 034)

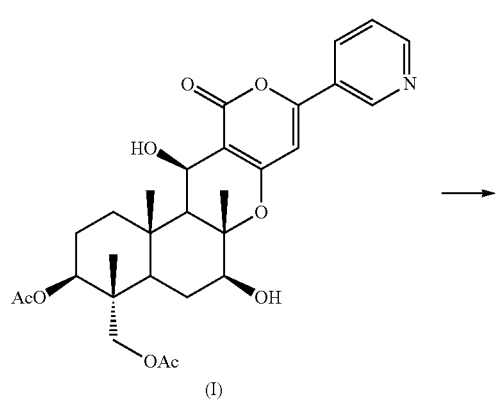

(I)

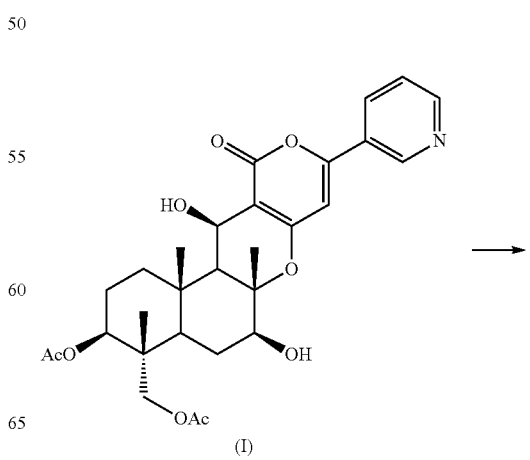

(I)

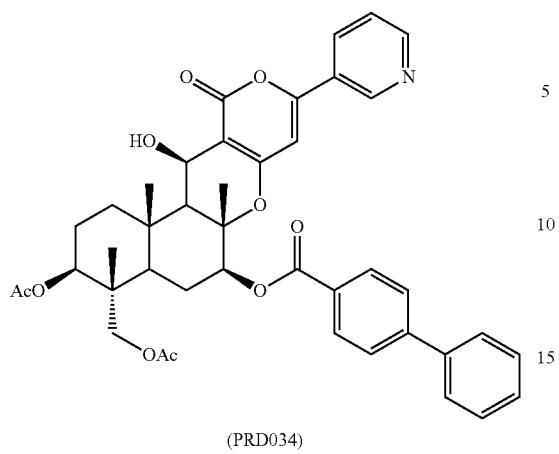

(PRD034)

In the same manner as in Example 2, PRD 034 (11.1 mg, 83%) was obtained as a white solid from compound I (10 mg, 18.5 μmol).

$^1$H NMR (CDCl$_3$, 300 MHz) δ 8.98 (d, 1H, J=2.4 Hz), 8.66 (dd, 1H, H-6", J=1.5, 4.8 Hz), 8.15 (s, 2H, H—Ar), 8.09-8.05 (m, 2H, H-4", Ar), 7.93-7.88 (m, 3H, H—Ar), 7.52-7.27 (m, 4H, H-5", Ar), 6.45 (s, 1H, H-5'), 5.26 (dd, 1H, H-7, J=5.7, 12.0 Hz), 5.04 (d, 1H, H-13, J=3.9 Hz), 4.82 (dd, 1H, H-1, J=5.1, 11.1 Hz), 3.86 (d, 1H, H-11a, J=12.0 Hz), 3.71 (d, 1H, H-11b, J=12.0 Hz), 3.00 (br s, 1H, OH-13), 2.23-1.44 (m, 8H, H-2, 3, 5, 8, 9), 2.14 (s, 3H, Ac), 2.06 (s, 3H, Ac), 1.87 (s, 3H, Me), 1.51 (s, 3H, Me), 0.92 (s, 3H, Me).

$^{13}$C NMR (CDCl$_3$, 150 MHz) δ 170.02, 170.53, 166.35, 163.98, 162.22, 157.44, 151.57, 146.82, 133.90, 133.72, 132.95, 131.47, 130.20, 128.65, 127.94, 127.10, 126.98, 126.81, 126.38, 125.77, 124.49, 123.61, 103.01, 99.36, 83.47, 78.53, 73.61, 64.99, 60.29, 54.86, 45.63, 40.42, 37.99, 36.21, 29.68, 25.34, 22.75, 21.15, 20.91, 17.56, 16.74, 13.28.

FAB-LRMS m/z 722 (MH$^+$); FAB-HRMS (CHCl$_3$) calcd. for C$_{42}$H$_{44}$NO$_{10}$ 722.2965 (MH$^+$). found 722.2950 (MH$^+$).

Example 41

Preparation of 7-benzo[b]thiophene-2-carboxyl-7-deacetylpyripyropene A (PRD 035)

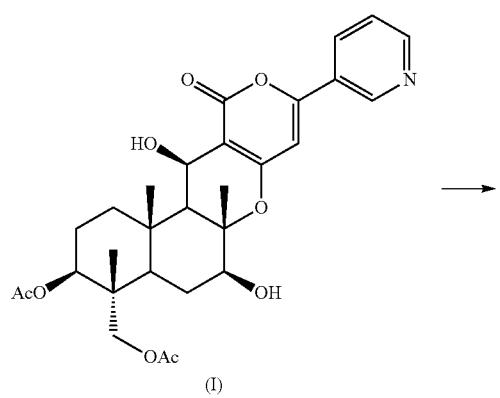

(I)

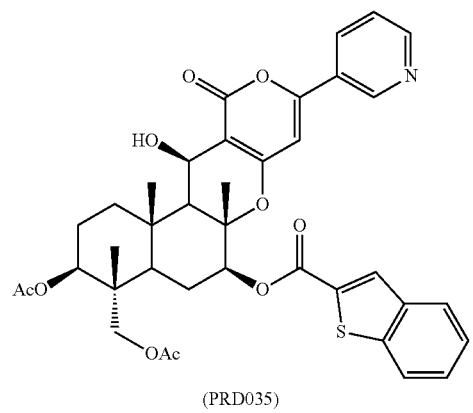

(PRD035)

In the same manner as in Example 2, PRD 035 (12.2 mg, 94%) was obtained as a white solid from compound I (10 mg, 18.5 μmol).

$^1$H NMR (CDCl$_3$, 300 MHz) δ 8.97 (d, 1H, H-2", J=2.4 Hz), 8.68-8.65 (m, 1H, H-6"), 8.18 (d, 2H, H—Ar, J=8.1 Hz), 8.08-8.05 (m, 1H, H-4"), 7.72 (d, 2H, H—Ar, J=8.1 Hz), 7.51-7.35 (m, 2H, H-5 ", Ar), 6.44 (s, 1H, H-5'), 5.31 (dd, 1H, H-7, J=4.8, 10.5 Hz), 5.05 (d, 1H, H-13, J=3.9 Hz), 4.83 (dd, 1H, H-1, J=5.1, 11.1 Hz), 3.87 (d, 1H, H-11a, J=12.0 Hz), 3.71 (d, 1H, H-11b, J=12.0 Hz), 3.01 (br s, 1H, OH-13), 2.23-1.26 (m, 8H, H-2, 3, 5, 8, 9), 2.15 (s, 3H, Ac), 2.06 (s, 3H, Ac), 1.88 (s, 3H, Me), 1.51 (s, 3H, Me), 0.92 (s, 3H, Me).

$^{13}$C NMR (CDCl$_3$, 150 MHz) δ 170.95, 170.53, 165.33, 163.98, 162.22, 157.35, 151.53, 146.80, 146.05, 139.86, 132.94, 130.26, 128.98, 128.82, 128.28, 127.27, 127.17, 127.11, 123.59, 102.95, 99.41, 83.45, 78.26, 73.55, 64.89, 60.27, 54.79, 45.48, 40.41, 37.92, 36.17, 25.36, 22.72, 21.13, 20.87, 17.52, 16.58, 13.22.

FAB-LRMS m/z 702 (MH$^+$); FAB-HRMS (CHCl$_3$) calcd. for C$_{38}$H$_{39}$NO$_{10}$S 701.2295 (MH$^+$). found 702.2340 (MH$^+$).

Example 42

Preparation of 7-2,2-difluorobenzo[d][1,3]dioxol-5-carboxyl-7-deacetylpyripyropene A (PRD 036)

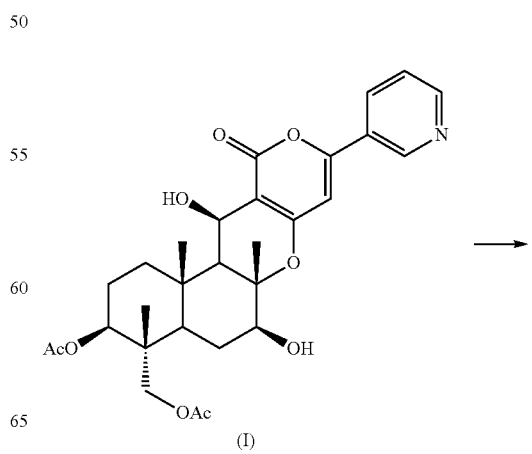

(I)

-continued

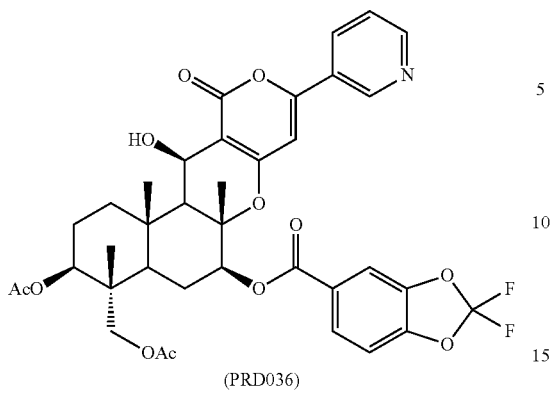

(PRD036)

In the same manner as in Example 2, PRD 036 (12.8 mg, 85%) was obtained as a white solid from compound I (10 mg, 18.5 μmol).

$^1$H NMR (CDCl$_3$, 300 MHz) δ 8.97 (d, 1H, H-2", J=2.4 Hz), 8.67 (dd, 1H, H-6", J=1.2, 4.8 Hz), 8.09-8.05 (m, 1H, H-4"), 7.95 (dd, 1H, H—Ar, J=1.5, 8.1 Hz), 7.79 (d, 1H, H—Ar, J=1.5 Hz), 7.41-7.36 (m, 1H, H-5"), 7.17 (d, 1H, H—Ar, J=8.1 Hz), 6.41 (s, 1H, H-5'), 5.25 (dd, 1H, H-7, J=4.8, 11.1 Hz), 5.03 (d, 1H, H-13, J=4.2 Hz), 4.82 (dd, 1H, H-1, J=5.4, 11.4 Hz), 3.83 (d, 1H, H-11a, J=12.0 Hz), 3.71 (d, 1H, H-11b, J=12.0 Hz), 3.01 (br s, 1H, OH-13), 2.23-1.42 (m, 8H, H-2, 3, 5, 8, 9), 2.13 (s, 3H, Ac), 2.07 (s, 3H, Ac), 1.84 (s, 3H, Me), 1.50 (s, 3H, Me), 0.91 (s, 3H, Me).

$^{13}$C NMR (CDCl$_3$, 150 MHz) δ 170.93, 170.51, 163.96, 163.91, 162.07, 157.43, 151.57, 147.25, 146.78, 143.79, 132.97, 127.08, 126.72, 126.31, 123.62, 110.88, 109.30, 102.98, 99.28, 83.25, 78.88, 73.51, 64.87, 60.21, 54.76, 45.46, 40.39, 37.91, 36.16, 29.67, 25.30, 22.70, 21.12, 20.84, 17.50, 16.50, 13.23.

FAB-LRMS m/z 726 (MH$^+$); FAB-HRMS (CHCl$_3$) calcd. for C$_{37}$H$_{38}$F$_2$NO$_{12}$ 726.2362 (MH$^+$). found 726.2388 (MH$^+$).

Example 43

Preparation of
7-2-naphthoyl-7-deacetylpyripyropene A (PRD 037)

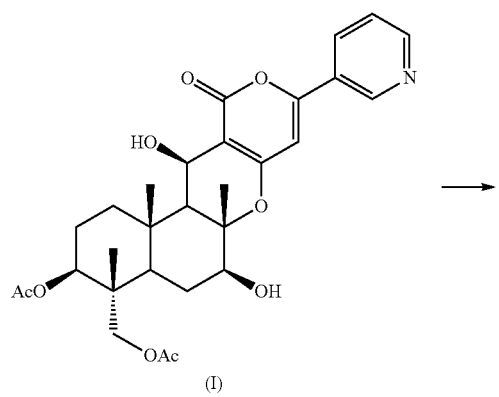

(I)

-continued

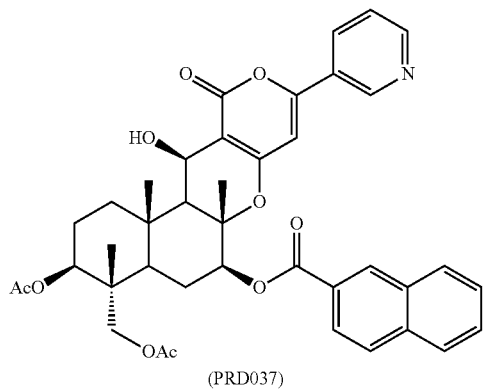

(PRD037)

In the same manner as in Example 2, PRD 037 (9.5 mg, 74%) was obtained as a white solid from compound I (10 mg, 18.5 μmol).

$^1$H NMR (CDCl$_3$, 300 MHz) δ 8.96 (d, 1H, H-2", J=2.4 Hz), 8.67-8.64 (m, 2H, H-6", Ar), 8.12 (dd, 1H, H-4", J=1.5, 8.7 Hz), 8.07-7.90 (m, 4H, H—Ar), 7.65-7.57 (m, 2H, H—Ar), 7.38-7.33 (m, 1H, H-5"), 6.42 (s, 1H, H-5'), 5.35 (dd, 1H, H-7, J=4.8, 11.1 Hz), 5.05 (d, 1H, H-13, J=2.1 Hz), 4.83 (dd, 1H, H-1, J=5.1, 11.1 Hz), 3.86 (d, 1H, H-11a, J=12.0 Hz), 3.72 (d, 1H, H-11b, J=12.0 Hz), 2.99 (br s, 1H, OH-13), 2.24-1.26 (m, 8H, H-2, 3, 5, 8, 9), 2.16 (s, 3H, Ac), 2.06 (s, 3H, Ac), 1.92 (s, 3H, Me), 1.92 (s, 3H, Me), 0.93 (s, 3H, Me).

$^{13}$C NMR (CDCl$_3$, 150 MHz) δ 170.96, 170.54, 165.64, 163.99, 162.23, 157.37, 151.54, 146.81, 135.66, 132.91, 132.47, 131.31, 129.37, 128.48, 128.31, 127.81, 127.34, 127.08, 126.82, 125.20, 123.57, 102.96, 99.41, 83.48, 78.40, 73.56, 64.89, 60.30, 54.82, 45.51, 40.43, 37.95, 36.20, 29.67, 25.41, 22.74, 21.14, 20.88, 17.54, 16.64, 13.24.

FAB-LRMS m/z 696 (MH$^+$); FAB-HRMS (CHCl$_3$) calcd. for C$_{40}$H$_{42}$NO$_{10}$ 696.2809 (MH$^+$). found 696.2833 (MH$^+$).

Example 44

Preparation of
7-1-naphthoyl-7-deacetylpyripyropene A (PRD 038)

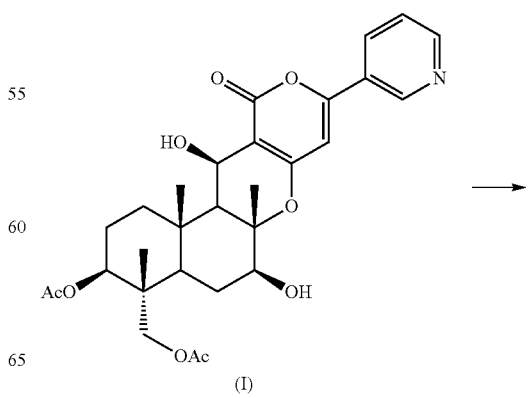

(I)

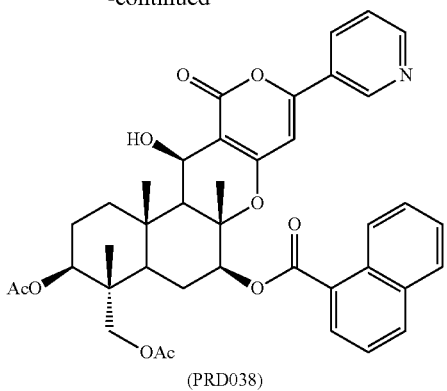

(PRD038)

In the same manner as in Example 2, PRD 038 (9.5 mg, 74%) was obtained as a white solid from compound I (10 mg, 18.5 μmol).

$^1$H NMR (CDCl$_3$, 300 MHz) δ 9.02-8.97 (m, 2H, H-2", Ar), 8.66 (dd, 2H, H-6", Ar), 8.26 (dd, 1H, H-4", J=0.9, 7.5 Hz), 7.92 (d, 1H, H—Ar, J=8.1 Hz), 7.70-7.64 (m, 1H, H—Ar), 7.60-7.53 (m, 2H H—Ar), 7.40-7.35 (m, 1H, H-5"), 6.45 (s, 1H, H-5'), 5.37 (dd, 1H, H-7, J=4.5, 10.5 Hz), 5.06 (d, 1H, H-13, J=1.5 Hz), 4.85 (dd, 1H, H-1, J=5.1, 11.1 Hz), 3.88 (d, 1H, H-11a, J=12.0 Hz), 3.75 (d, 1H, H-11b, J=12.0 Hz), 2.98 (br s, 1H, OH-13), 2.24-1.26 (m, 8H, H-2, 3, 5, 8, 9), 2.18 (s, 3H, Ac), 2.06 (s, 3H, Ac), 1.88 (s, 3H, Me), 1.51 (s, 3H, Me), 0.93 (s, 3H, Me).

$^{13}$C NMR (CDCl$_3$, 150 MHz) δ 170.92, 170.53, 163.95, 162.17, 161.73, 157.33, 151.42, 146.71, 142.28, 138.64, 133.25, 133.04, 130.98, 127.20, 127.14, 125.63, 125.07, 123.64, 122.76, 102.98, 99.43, 83.34, 78.90, 73.51, 64.87, 60.23, 54.73, 45.49, 40.42, 37.90, 36.15, 29.67, 25.35, 22.71, 21.12, 20.86, 17.52, 16.49, 13.22.

FAB-LRMS m/z 696 (MH$^+$); FAB-HRMS (CHCl$_3$) calcd. for C$_{40}$H$_{42}$NO$_{10}$ 696.2809 (MH$^+$). found 696.2833 (MH$^+$). FAB-LRMS m/z 696 (MH$^+$); FAB-HRMS (CHCl$_3$) calcd. for C$_{40}$H$_{42}$NO$_{10}$ 696.2809 (MH$^+$). found 696.2833 (MH$^+$).

Example 45

Preparation of 7-O-3-(4-methoxyphenyl)propionyl-7-deacetylpyripyropene A (PRD 084)

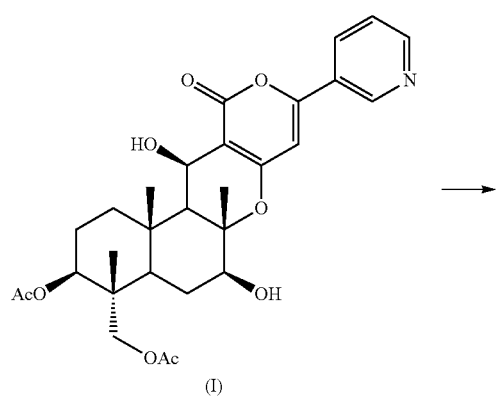

(I)

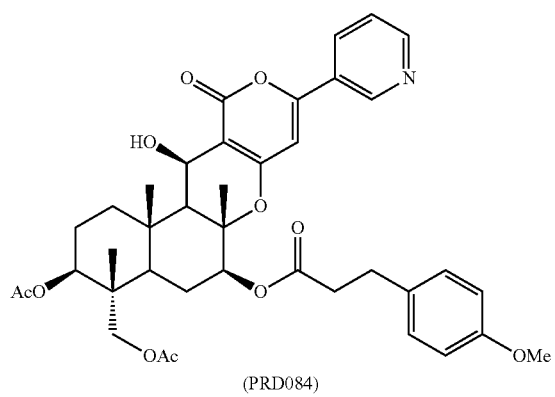

(PRD084)

In the same manner as in Example 2, PRD 084 (12.2 mg, 89%) was obtained as a white solid from compound I (10 mg, 18.3 μmol).

$^1$H NMR (CDCl$_3$, 300 MHz) δ 9.01 (dd, 1H, H-2", J=0.6, 2.1 Hz), 8.70 (dd, 1H, H-6", J=1.5, 4.8 Hz), 8.11-8.07 (m, 1H, H-4"), 7.43-7.39 (m, 1H, H-5"), 7.17 (d, 2H, H—Ar, J=8.4 Hz), 6.85 (d, 2H, H—Ar, J=8.4 Hz), 6.33 (s, 1H, H-5'), 5.03-4.97 (m, 2H, H-7, 13), 4.79 (dd, 1H, H-1, J=5.1, 11.7 Hz), 3.80 (d, 1H, H-11a, J=12.0 Hz), 3.75 (s, 3H, OMe), 3.66 (d, 1H, H-11b, J=12.0 Hz), 2.98 (t, 2H, COCH$_2$CH$_2$Ar, J=7.2 Hz), 2.92 (br d, 1H, OH-13, J=1.8 Hz), 2.72 (t, 2H, COCH$_2$CH$_2$Ar, J=7.2 Hz), 2.17-1.36 (m, 8H, H-2, 3, 5, 8, 9), 2.09 (s, 3H, Ac), 2.04 (s, 3H, Ac), 1.65 (s, 3H, Me), 1.42 (s, 3H, Me), 0.87 (s, 3H, Me).

ESI-LRMS m/z 703 (M+Na$^+$). ESI-HRMS (MeOH) calcd. for C$_{39}$H$_{45}$NNaO$_{11}$ 726.2890 (M+Na$^+$). found 712.2754 (M+Na$^+$).

Example 46

Preparation of 7-O-4-methoxyphenylacetyl-7-deacetylpyripyropene A (PRD 087)

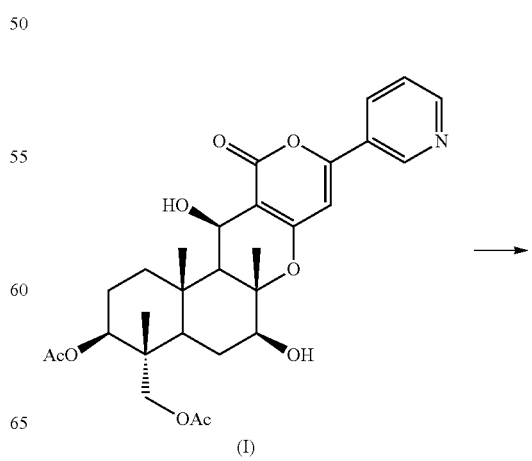

(I)

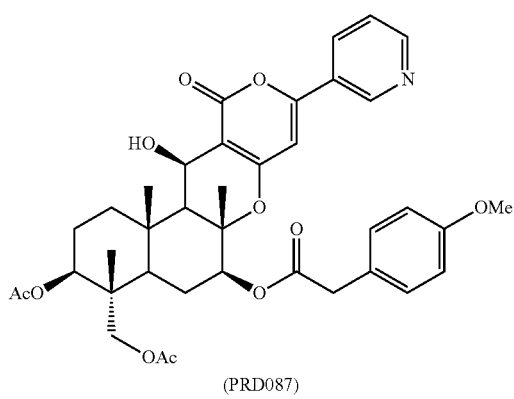

(PRD087)

In the same manner as in Example 2, PRD 087 (12.6 mg, quant.) was obtained as a white solid from compound I (10 mg, 18.3 μmol).

$^1$H NMR (CDCl$_3$, 300 MHz) δ 9.00 (d, 1H, H-2", J=1.8 Hz), 8.70 (dd, 1H, H-6", J=1.5, 4.8 Hz), 8.13-8.09 (m, 1H, H-4"), 7.42 (dd, 1H, H-5", J=4.8, 8.1 Hz), 7.30-7.25 (m, 1H, H—Ar), 6.95-6.92 (m, 2H, H—Ar), 6.86-6.82 (m, 1H, H—Ar), 6.28 (s, 1H, H-5'), 5.01-4.96 (m, 2H, H-7, 13), 4.78 (dd, 1H, H-1, J=4.8, 11.4 Hz), 3.80 (d, 1H, H-11a, J=12.0 Hz), 3.78 (s, 3H, OMe), 3.69 (d, 1H, H-11b, J=12.0 Hz), 3.69 (s, 2H, COCH$_2$Ar), 2.90 (br s, 1H, OH-13), 2.17-1.26 (m, 8H, H-2, 3, 5, 8, 9), 2.08 (s, 3H, Ac), 2.04 (s, 3H, Ac), 1.60 (s, 3H, Me), 1.42 (s, 3H, Me), 0.88 (s, 3H, Me).

ESI-LRMS m/z 712 (M+Na$^+$). ESI-HRMS (MeOH) calcd. for C$_{38}$H$_{43}$NNaO$_{11}$ 712.2734 (M+Na$^+$). found 712.2754 (M+Na$^+$).

Example 47

Preparation of 7-O-1-thymineacetyl-7-deacetylpyripyropene A (PRD 090)

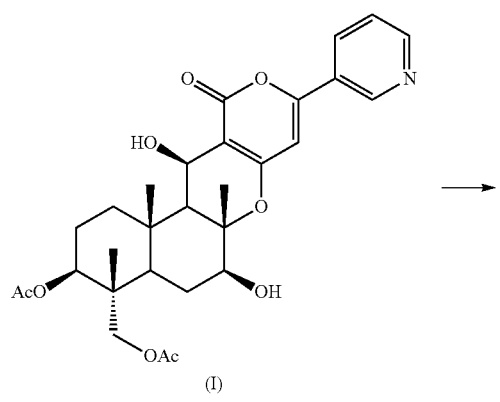

(I)

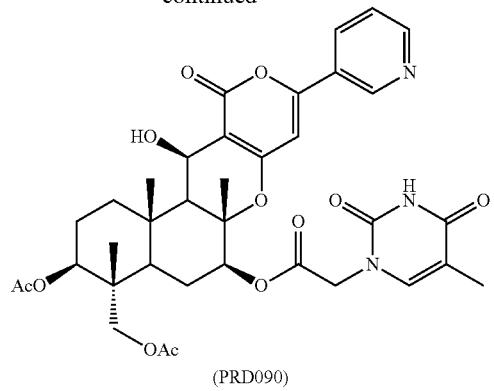

(PRD090)

In an argon atmosphere, BOP (23 mg, 73.2 μmol), DMAP (2.2 mg, 18.3 μmol), and thymine-1-acetic acid (14 mg, 73.2 μmol) were added to a solution of compound I (10 mg, 18.3 μmol) in DMF (0.5 mL) and stirred for 240 hours at room temperature. The reaction mixture was diluted with EtOAc, and the organic layer was washed with water and dried over anhydrous sodium sulfate. The solution was filtered, and the filtrate was concentrated at a reduced pressure. The resulting residue was purified by neutral flash silica gel column chromatography (1×3, MeOH in CH$_2$Cl$_2$ 2-5%) to give PRD 090 (11.2 mg, 87%) as a white solid.

$^1$H NMR (CDCl$_3$, 300 MHz) δ 9.36 (br s, 1H, NH), 9.04 (d, 1H, H-2", J=2.4 Hz), 8.69 (dd, 1H, H-6", J=1.5, 5.1 Hz), 8.15-8.11 (m, 1H, H-4"), 7.44-7.40 (m, 1H, H-5"), 7.02 (s, 1H, H—Ar), 6.56 (s, 1H, H-5'), 5.08 (dd, 1H, H-7, J=5.1, 11.1 Hz), 5.00 (d, 1H, H-13, J=4.2 Hz), 4.79 (dd, 1H, H-1, J=4.8, 11.1 Hz), 4.68 (d, 1H, ½COCH$_2$Ar, J=17.4 Hz), 4.38 (d, 1H, ½COCH$_2$Ar, J=17.4 Hz), 3.83 (d, 1H, H-11a, J=12.0 Hz), 3.70 (d, 1H, H-11b, J=12.0 Hz), 2.19-1.25 (m, 8H, H-2, 3, 5, 8, 9), 2.07 (s, 3H, Ac), 2.05 (s, 3H, Ac), 1.96 (s, 3H, Ar-Me), 1.68 (s, 3H, Me), 1.44 (s, 3H, Me), 0.90 (s, 3H, Me).

ESI-LRMS m/z 730 (M+Na$^+$). ESI-HRMS (MeOH) calcd. for C$_{36}$H$_{41}$N$_3$NaO$_{12}$ 730.2588 (M+Na$^+$). found 730.2588 (M+Na$^+$).

Example 48

Preparation of 7-O-2-(1H-tetrazol-1-yl)acetyl-7-deacetylpyripyropene A (PRD 092)

(I)

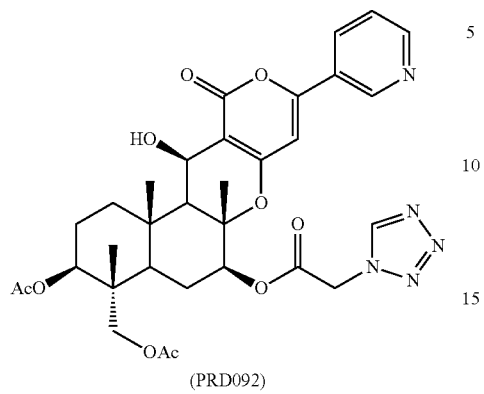

(PRD092)

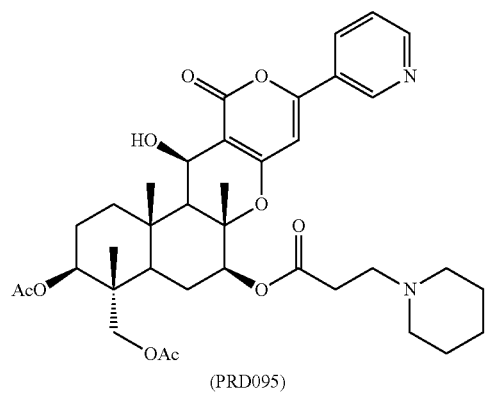

(PRD095)

In the same manner as in Example 2, PRD 092 (15.7 mg, 66%) was obtained as a white solid from compound I (20 mg, 36.6 μmol).

$^1$H NMR (CDCl$_3$, 300 MHz) δ 9.03 (d, 1H, H-2", J=2.4 Hz), 8.90 (s, 1H, H—Ar), 8.70 (dd, 1H, J=1.5, 4.8 Hz), 8.13-8.09 (m, 1H, H-4"), 7.42 (dd, 1H, H-5", J=4.8, 8.1 Hz), 6.46 (s, 1H, H-5'), 5.46 (d, 1H, ½COCH$_2$Ar, J=17.7 Hz), 5.32 (d, 1H, ½COCH$_2$Ar, J=17.7 Hz), 5.08 (dd, 1H, J=4.8, 11.1 Hz), 4.99 (dd, 1H, H-13, J=2.4, 3.9 Hz), 4.79 (dd, 1H, H-1, J=5.1, 11.1 Hz), 3.75 (s, 2H, H-11), 3.00 (br d, 1H, OH-13, J=2.4 Hz), 2.19-1.26 (m, 8H, H-2, 3, 5, 8, 9), 2.08 (s, 3H, Ac), 2.05 (s, 3H, Ac), 1.63 (s, 3H, Me), 1.44 (s, 3H, Me), 0.90 (s, 3H, Me).

ESI-LRMS m/z 674 (M+Na$^+$). ESI-HRMS (MeOH) calcd. for C$_{32}$H$_{37}$N$_5$NaO$_{13}$ 674.2438 (M+Na$^+$). found 674.2438 (M+Na$^+$).

In the same manner as in Example 2, PRD 095 (17.8 mg, 95%) was obtained as a white solid from compound I (15 mg, 27.5 mol).

$^1$H NMR (CDCl$_3$, 300 MHz) δ 9.06 (d, 1H, H-2", J=2.4 Hz), 8.69 (dd, 1H, H-6", J=1.2, 4.8 Hz), 8.12-8.08 (m, 1H, H-4"), 7.41 (dd, 1H, H-5", J=4.8, 7.8 Hz), 6.44 (s, 1H, H-5'), 5.30-4.99 (m, 2H, H-7, 13), 4.80 (dd, 1H, H-1, J=5.1, 11.1 Hz), 3.81 (d, 1H, H-11a, J=12.0 Hz), 3.69 (d, 1H, H-11b, J=12.0 Hz), 2.98 (br s, 1H, OH-13), 2.78-2.73 (m, 2H, COCH$_2$CH$_2$N), 2.66-2.60 (m, 2H, COCH$_2$CH$_2$N), 2.48-2.45 (m, 4H, CH$_2$N(CH$_2$CH$_2$)$_2$CH$_2$), 2.19-1.26 (m, 14H, H-2, 3, 5, 8, 9, CH$_2$N(CH$_2$CH$_2$)$_2$CH$_2$), 2.09 (s, 3H, Ac), 2.05 (s, 3H, Ac), 1.70 (s, 3H, Me), 1.45 (s, 3H, Me), 0.89 (s, 3H, Me).

ESI-LRMS m/z 681 (M+Na$^+$). ESI-HRMS (MeOH) calcd. for C$_{37}$H$_{48}$N$_2$NaO$_{10}$ 668.3309 (M+Na$^+$). found 680.3389 (M+Na$^+$).

Example 49

Preparation of 7-O-3-(pyperidin-1-yl)propionyl-7-deacetylpyripyropene A (PRD 095)

Example 50

Preparation of 7-O-pyrazinecarboxyl-7-deacetylpyripyropene A (PRD 096)

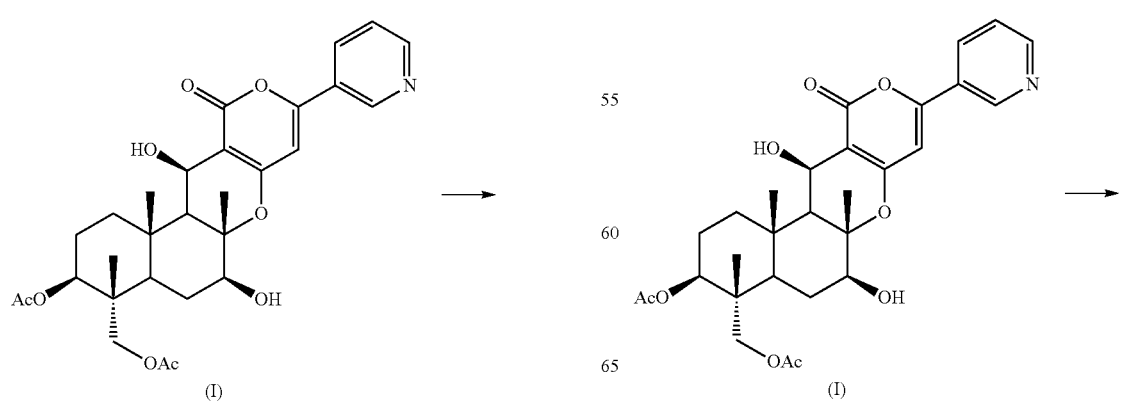

(I)

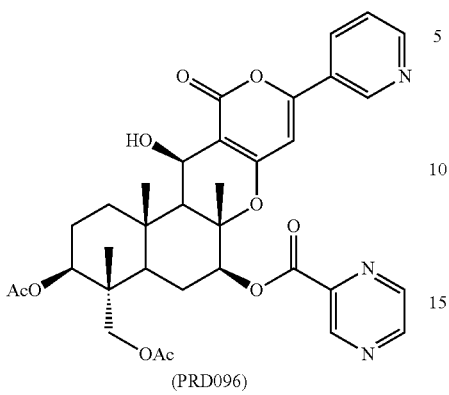

(PRD096)

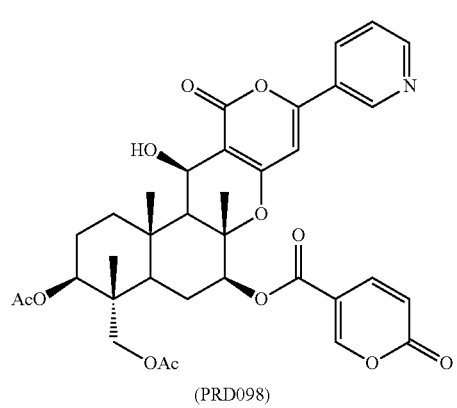

(PRD098)

In the same manner as in Example 2, PRD 096 (16.3 mg, 92%) was obtained as a white solid from compound I (15 mg, 27.5 μmol).

$^1$H NMR (CDCl$_3$, 300 MHz) δ 9.38 (d, 1H, H—Ar, J=1.6 Hz), 8.97 (d, 1H, H-2", J=0.6 Hz), 8.82-8.79 (m, 2H, H—Ar), 8.67 (dd, 1H, H-6", J=1.8, 4.8 Hz), 8.09-8.05 (m, 1H, H-4"), 7.41-7.36 (m, 1H, H-5"), 6.42 (s, 1H, H-5'), 5.40 (dd, 1H, H-7, J=5.4, 11.1 Hz), 5.05 (d, 1H, H-13, J=1.5 Hz), 4.82 (dd, 1H, H-1, J=4.8, 11.1 Hz), 3.84 (d, 1H, H-11a, J=12.0 Hz), 3.71 (d, 1H, H-11b, J=12.0 Hz), 3.04 (br s, 1H, OH-13), 2.23-1.26 (m, 8H, H-2, 3, 5, 8, 9), 2.13 (s, 3H, Ac), 2.06 (s, 3H, Ac), 1.87 (s, 3H, Me), 1.51 (s, 3H, Me), 0.92 (s, 3H, Me).

ESI-LRMS m/z 670 (M+Na$^+$). ESI-HRMS (MeOH) calcd. for C$_{34}$H$_{37}$N$_3$NaO$_{10}$ 670.2377 (M+Na$^+$). found 674.2391 (M+Na$^+$).

Example 51

Preparation of 7-O-2-pyrone-5-carboxyl-7-deacetylpyripyropene A (PRD 098)

In the same manner as in Example 2, PRD 098 (18.2 mg, quant.) was obtained as a red solid from compound I (15 mg, 27.5 μmol).

$^1$H NMR (CDCl$_3$, 300 MHz) δ 8.99 (dd, 1H, H-2", J=0.6, 1.5 Hz), 8.70-8.68 (m, 1H, H-6"), 8.38-8.37 (m, 1H, H—Ar), 8.11-8.07 (m, 1H, H-4"), 7.86-7.82 (m, 1H, H—Ar), 7.42-7.28 (m, 1H, H-5"), 6.43-6.38 (m, 2H, H-5', Ar), 5.20 (dd, 1H, H-7, J=4.8, 11.1 Hz), 5.02 (d, 1H, H-13, J=3.3 Hz), 4.82 (dd, 1H, H-1, J=4.5, 11.1 Hz), 3.80 (d, 1H, H-11a, J=12.0 Hz), 3.73 (d, 1H, H-11b, J=12.0 Hz), 3.04 (br s, 1H, OH-13), 2.22-1.26 (m, 8H, H-2, 3, 5, 8, 9), 2.12 (s, 3H, Ac), 2.06 (s, 3H, Ac), 1.78 (s, 3H, Me), 1.48 (s, 3H, Me), 0.91 (s, 3H, Me).

ESI-LRMS m/z 686 (M+Na$^+$). ESI-HRMS (MeOH) calcd. for C$_{35}$H$_{37}$NNaO$_{12}$ 686.2213 (M+Na$^+$). found 686.2234 (M+Na$^+$).

Example 52

Preparation of 7-O-3-phenylpropionyl-7-deacetylpyripyropene A (PRD 100)

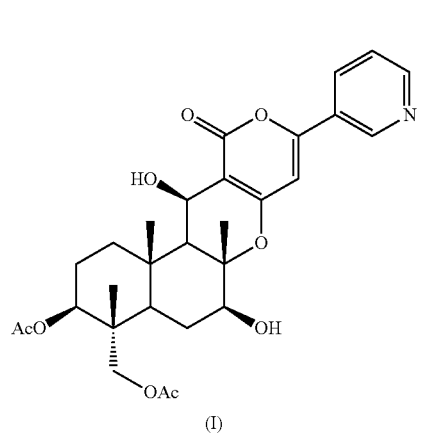

(I)

→

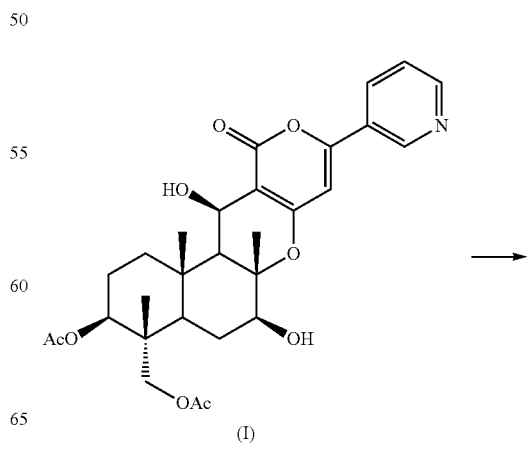

(I)

→

-continued

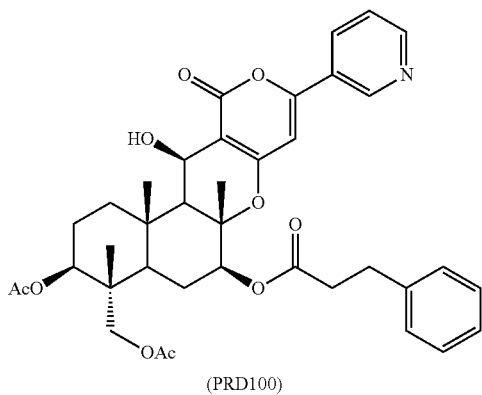

(PRD100)

In the same manner as in Example 1, PRD 100 (16.3 mg, 88%) was obtained as a white solid from compound I (15 mg, 27.5 µmol).

$^1$H NMR (CDCl$_3$, 300 MHz) δ 8.99 (dd, 1H, H-2", J=0.6, 2.4 Hz), 8.70 (dd, 1H, H-6", J=1.5, 4.8 Hz), 8.12-8.08 (m, 1H, H-4"), 7.45-7.40 (m, 1H, H-5"), 7.34-7.19 (m, 5H, H—Ar), 6.32 (s, 1H, H-5'), 5.03-4.97 (m, 2H, H-7, 13), 4.78 (dd, 1H, H-1, J=5.1, 11.4 Hz), 3.80 (d, 1H, H-11a, J=12.0 Hz), 3.73 (d, 1H, H-11b, J=12.0 Hz), 3.07-2.95 (m, 2H, COCH$_2$), 2.79-2.66 (m, 2H, CH$_2$Ar), 2.23-1.25 (m, 8H, H-2, 3, 5, 8, 9), 2.09 (s, 3H, Ac), 2.04 (s, 3H, Ac), 1.64 (s, 3H, Me), 1.42 (s, 3H, Me), 0.87 (s, 3H, Me).

ESI-LRMS m/z 696 (M+Na$^+$). ESI-HRMS (MeOH) calcd. for C$_{38}$H$_{43}$NNaO$_{10}$ 696.2785 (M+Na$^+$). found 696.2769 (M+Na$^+$).

Example 53

Preparation of 2-(1-trityl-1H-tetrazol-5-yl)acetic acid

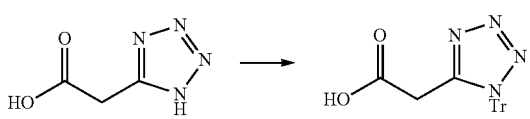

In an argon atmosphere, TrCl (936 mg, 3 mmol) and Et$_3$N (556 µL, 3 mmol) were added to a solution of 1H-tetrazole-5-acetic acid (128 mg, 1 mmol) in THF (10 mL) and stirred for 3 hours at room temperature. The reaction mixture was diluted with EtOAc, and the organic layer was washed with water and dried over anhydrous sodium sulfate. The solution was filtered, and the filtrate was concentrated at a reduced pressure. The resulting residue was purified by neutral flash silica gel column chromatography (1.5×6, MeOH in CH$_2$Cl$_2$ 0-0.5%) to give 2-(1-trityl-1H-tetrazol-5-yl)acetic acid (62 mg, 18%) as a white solid.

Example 54

Preparation of 7-O-(1H-tetrazol-5-yl)acetyl-7-deacetylpyripyropene A (PRD 102)

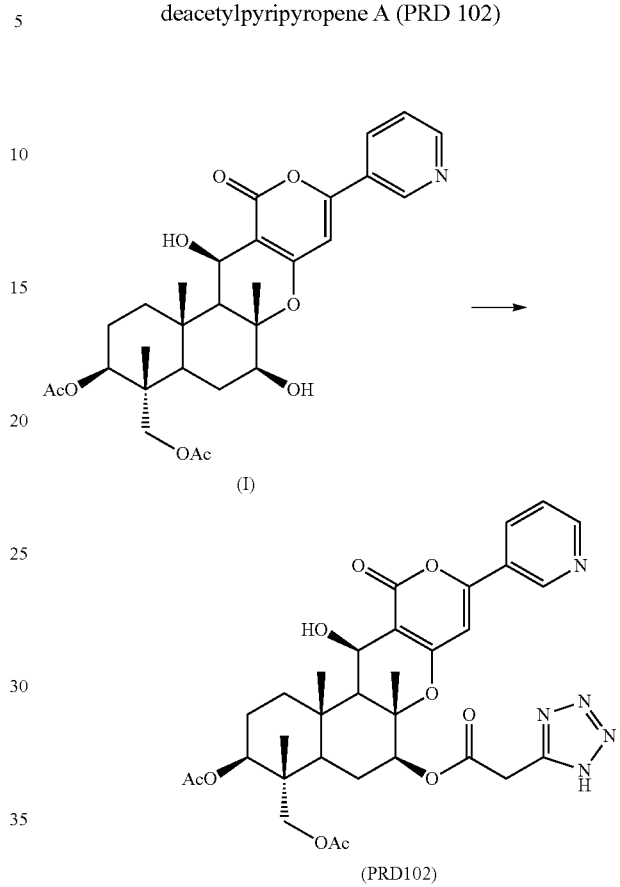

In an argon atmosphere, EDCI (19 mg, 100 µmol), DMAP (2.2 mg, 18.3 µmol, and 2-(1-trityl-1H-tetrazol-5-yl)acetic acid (36 mg, 100 µmol) were added to a solution of compound I (20 mg, 36.6 µmol) in CH$_2$Cl$_2$ (0.5 mL) and stirred for 4 hours at room temperature. The reaction mixture was diluted with EtOAc, and the organic layer was washed with water and dried over anhydrous sodium sulfate. The solution was filtered, and the filtrate was concentrated at a reduced pressure. The resulting residue was purified by PTLC (MeOH in CH$_2$Cl$_2$ 10%) to give 7-O-(1-trityl-1H-tetrazole-5-acetyl-7-deacetylpyripyropene A. The thus-obtained 7-O-(1-trityl-1H-tetrazole-5-acetyl-7-deacetylpyripyropene A was dissolved in MeOH (0.5 mL) and heated to reflux for 1 hour at 75° C. The reaction mixture was concentrated at a reduced pressure, and the resulting residue was purified by neutral flash silica gel column chromatography (1×3+1, MeOH in CH$_2$Cl$_2$ 0-20%) to give PRD 102 (8.4 mg, 2 steps 35%) as a white solid.

$^1$H NMR (MeOD-d4, 300 MHz) δ 9.02 (d, 1H, H-2", J=1.8 Hz), 8.63 (d, 1H, H-6", J=3.9 Hz), 8.30-8.26 (m, 1H, H-4"), 7.55 (dd, 1H, H-5", J=4.5, 10.5 Hz), 6.76 (s, 1H, H-5'), 5.04 (dd, 1H, H-7, J=4.5, 10.5 Hz), 4.95 (d, 1H, H-13, J=3.6 Hz), 4.79 (dd, 1H, H-1, J=5.4, 10.5 Hz), 4.26 (d, 1H, ½COCH$_2$Ar, J=17.7 Hz), 4.17 (d, 1H, ½COCH$_2$Ar, J=17.4 Hz), 3.82 (d, 1H, H-11a, J=11.7 Hz), 3.75 (d, 1H, H-11b, J=11.7 Hz), 2.16-1.28 (m, 8H, H-2, 3, 5, 8, 9), 2.04 (s, 3H, Ac), 2.02 (s, 3H, Ac), 1.63 (s, 3H, Me), 1.47 (s, 3H, Me), 0.92 (s, 3H, Me).

ESI-LRMS m/z 674 (M+Na$^+$). ESI-HRMS (MeOH) calcd. for C$_{32}$H$_{37}$N$_5$NaO$_{10}$ 674.2438 (M+Na$^+$). found 674.2488 (M+Na$^+$).

Example 55

Preparation of 7-O-4-(4-methoxyphenyl)butytyl-7-deacetylpyripyropene A (PRD 103)

Example 56

Preparation of 7-O-3-(4-methylpiperazin-1-yl)propionyl-7-deacetylpyripyropene A (PRD 104)

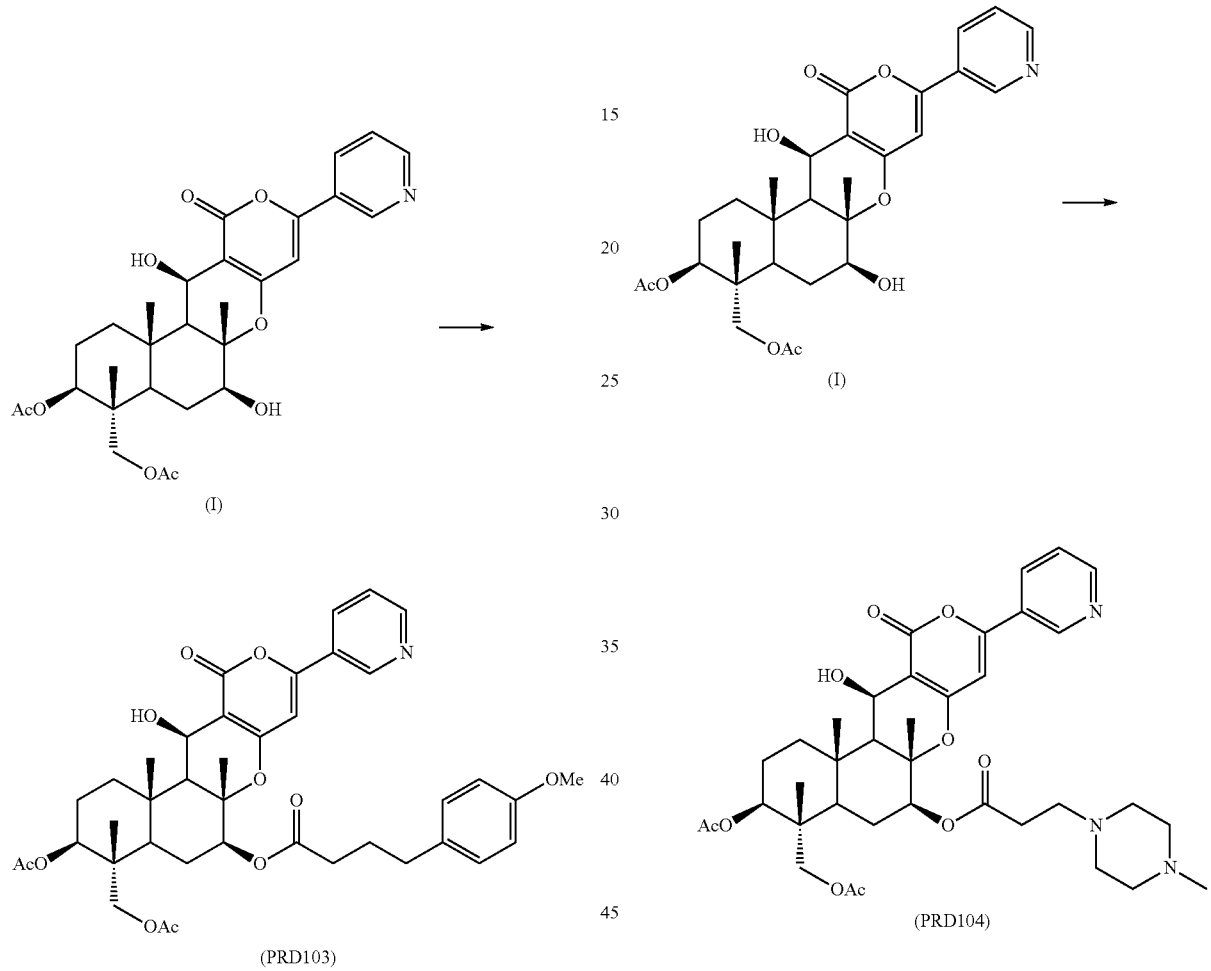

In the same manner as in Example 2, PRD 103 (19.7 mg, quant.) was obtained as a white solid from compound I (15 mg, 57.5 μmol).

$^1$H NMR (CDCl$_3$, 300 MHz) δ 8.92 (dd, 1H, H-2", J=0.9, 2.4 Hz), 8.67 (dd, 1H, H-6", J=1.5, 4.8 Hz), 7.96-7.92 (m, 1H, H-4"), 7.39-7.34 (m, 1H, H-5"), 7.13 (d, 2H, H—Ar, J=8.4 Hz), 6.84 (d, 2H, H—Ar, J=8.4 Hz), 6.34 (s, 1H, H-5'), 5.05-4.99 (m, 2H, H-7, 13), 4.79 (dd, 1H, H-1, J=5.4, 11.1 Hz), 3.83-3.77 (m, 4H, H-11a, OMe), 3.70 (d, 1H, H-11b, J=12.0 Hz), 3.01 (br s, 1H, OH-13), 2.67 (t, 2H, COCH$_2$(CH$_2$)$_2$Ar, J=7.2 Hz), 2.47-2.41 (m, 2H, CO(CH$_2$)$_2$CH$_2$Ar), 2.19-1.26 (m, 10H, H-2, 3, 5, 8, 9, COCH$_2$CH$_2$CH$_2$Ar), 2.10 (s, 3H, Ac), 2.05 (s, 3H, Ac), 1.71 (s, 3H, Me), 1.44 (s, 3H, Me), 0.89 (s, 3H, Me).

ESI-LRMS m/z 740 (M+Na$^+$). ESI-HRMS (MeOH) calcd. for C$_{40}$H$_{47}$NNaO$_{11}$ 740.3047 (M+Na$^+$). found 740.3049 (M+Na$^+$).

In the same manner as in Example 1, PRD 104 (13.2 mg, 52%) was obtained as a white solid from compound I (20 mg, 36.6 μmol).

$^1$H NMR (CDCl$_3$, 300 MHz) δ 9.00 (dd, 1H, H-2", J=0.6, 2.4 Hz), 8.69 (dd, 1H, H-6", J=1.5, 4.8 Hz), 8.12-8.08 (m, 1H, H-4"), 7.43-7.39 (m, 1H, H-5"), 6.44 (s, 1H, H-5'), 5.04-4.99 (m, 2H, H-7, 13), 4.79 (dd, 1H, H-1, J=5.1, 11.1 Hz), 3.81 (d, 1H, H-11a, J=12.0 Hz), 3.70 (d, 1H, H-11b, J=12.0 Hz), 2.81-2.76 (m, 2H, COCH$_2$CH$_2$), 2.64-2.41 (m, 10H, COCH$_2$CH$_2$N(CH$_2$CH$_2$)$_2$NMe), 2.29 (s, 3H, NMe), 2.19-1.43 (m, 8H, H-2, 3, 5, 8, 9), 2.09 (s, 3H, Ac), 2.05 (s, 3H, Ac), 1.70 (s, 3H, Me), 1.45 (s, 3H, Me), 0.89 (s, 3H, Me).

ESI-LRMS m/z 696 (MH$^+$). ESI-HRMS (MeOH) calcd. for C$_{37}$H$_{50}$N$_3$O$_{10}$ 696.3496 (MH$^+$). found 696.3471 (MH$^+$).

Example 57

Preparation of 7-O-methoxymethoxyacetyl-7-deacetylpyripyropene A (PRD 106)

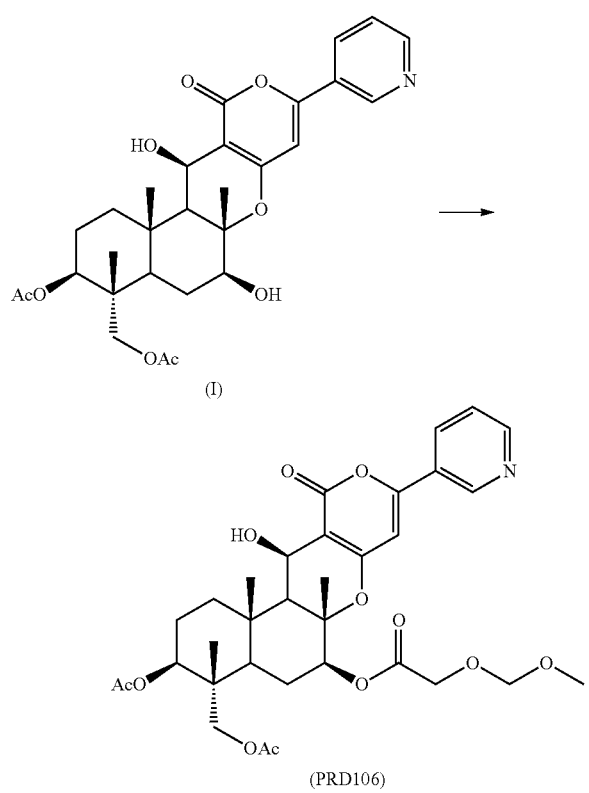

(PRD106)

In an argon atmosphere, EDCI (19 mg, 100 μmol), DMAP (2.2 mg, 18.3 μmol), and crude methoxymethoxyacetic acid (100 μmol) prepared by the method described in the literature (Tetrahedron 2002, 58, 7663) were added to a solution of compound I (20 mg, 36.6 μmol) in $CH_2Cl_2$ (0.5 mL) and stirred for 0.5 hours at room temperature. The reaction mixture was diluted with EtOAc, and the organic layer was washed with 1N HCl and water and dried over anhydrous sodium sulfate. The solution was filtered, and the filtrate was concentrated at a reduced pressure. The resulting residue was purified by neutral flash silica gel column chromatography (1×4, MeOH in $CH_2Cl_2$ 0.5-1.5%) to give PRD 106 (20.2 mg, 85%) as a white solid.

$^1$H NMR (CDCl$_3$, 400 MHz) δ 9.01 (dd, 1H, H-2", J=0.8, 2.4 Hz), 8.69 (dd, 1H, H-6", J=1.6, 4.8 Hz), 8.11-8.08 (m, 1H, H-4"), 7.43-7.39 (m, 1H, H-5"), 6.46 (s, 1H, H-5), 5.11 (dd, 1H, H-7, J=4.4, 11.4 Hz), 5.00 (d, 1H, H-13, J=2.4 Hz), 4.81-4.76 (m, 3H, H-1, COCH$_2$OCH$_2$OCH$_3$), 4.31 (d, 1H, ½COCH$_2$OCH$_2$OCH$_3$), 4.23 (d, 1H, ½COCH$_2$OCH$_2$OCH$_3$), 3.83 (d, 1H, H-11a, J=12.0 Hz), 3.69 (d, 1H, H-11b, J=12.0 Hz), 3.45 (s, 3H, OMe), 3.01 (br s, 1H, OH-13), 2.19-1.24 (m, 8H, H-2, 3, 5, 8, 9), 2.09 (s, 3H, Ac), 2.05 (s, 3H, Ac), 1.45 (s, 3H, Me), 1.45 (s, 3H, Me), 0.89 (s, 3H, Me).

ESI-LRMS m/z 644 (MH$^+$). ESI-HRMS (MeOH) calcd. for C$_{33}$H$_{42}$NO$_{12}$ 644.2707 (MH$^+$). found 644.2678 (MH$^+$).

Example 58

Preparation of 7-O-methoxyethoxymethoxyacetyl-7-deacetylpyripyropene A (PRD 108)

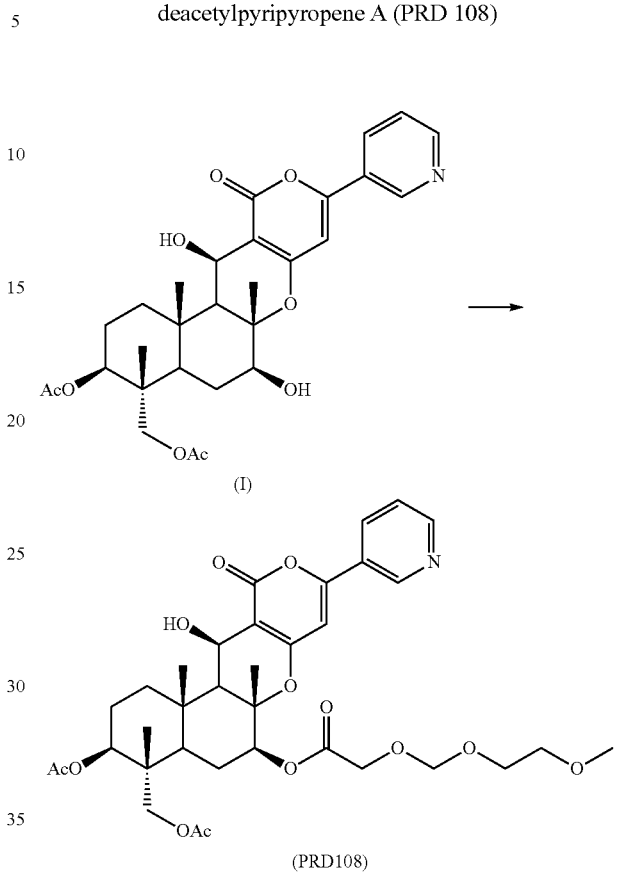

(PRD108)

In an argon atmosphere, EDCI (19 mg, 100 μmol), DMAP (2.2 mg, 18.3 μmol), and crude methoxyethoxymethoxyacetic acid (100 μmol) prepared by the method described in the literature (Tetrahedron 2002, 58, 7663) were added to a solution of compound I (20 mg, 36.6 μmol) in $CH_2Cl_2$ (0.5 mL) and stirred for 0.5 hours at room temperature. The reaction mixture was diluted with EtOAc, and the organic layer was washed with 1N HCl and water and dried over anhydrous sodium sulfate. The solution was filtered, and the filtrate was concentrated at a reduced pressure. The resulting residue was purified by neutral flash silica gel column chromatography (1×4, MeOH in $CH_2Cl_2$ 0.5-1.5%) to give PRD 108 (23.6 mg, 93%) as a white solid.

$^1$H NMR (CDCl$_3$, 300 MHz) δ 9.02 (dd, 1H, H-2", J=0.6, 2.4 Hz), 8.70 (dd, 1H, H-6", J=1.5, 4.8 Hz), 8.13-8.09 (m, 1H, H-4"), 7.43-7.39 (m, 1H, H-5"), 6.49 (s, 1H, H-5'), 5.11-5.08 (m, 1H, H-7), 5.00 (d, 1H, H-13, J=3.6 Hz), 4.87 (s, 2H, COCH$_2$O), 4.81-4.76 (m, 1H, H-1), 4.34 (d, 1H, ½COCH$_2$OCH$_2$OCH$_2$), 4.27 (d, 1H, ½COCH$_2$OCH$_2$OCH$_2$), 3.85-3.74 (m, 3H, H-11a, COCH$_2$OCH$_2$OCH$_2$CH$_2$), 3.66 (d, 1H, H-11b, J=12.0 Hz), 3.61-3.55 (m, 2H, COCH$_2$OCH$_2$OCH$_2$CH$_2$), 3.41 (s, 3H, OMe), 2.99 (br s, 1H, OH-13), 2.19-1.38 (m, 8H, H-2, 3, 5, 8, 9), 2.09 (s, 3H, Ac), 2.05 (s, 3H, Ac), 1.69 (s, 3H, Me), 1.44 (s, 3H, Me), 0.89 (s, 3H, Me).

ESI-LRMS m/z 710 (M+Na$^+$). ESI-HRMS (MeOH) calcd. for C$_{35}$H$_{45}$NNaO$_{13}$ 710.2789 (M+Na$^+$). found 710.2789 (M+Na$^+$).

Example 59

Preparation of 7-O-hydroxyacetyl-7-deacetylpyripyropene A (PRD 107)

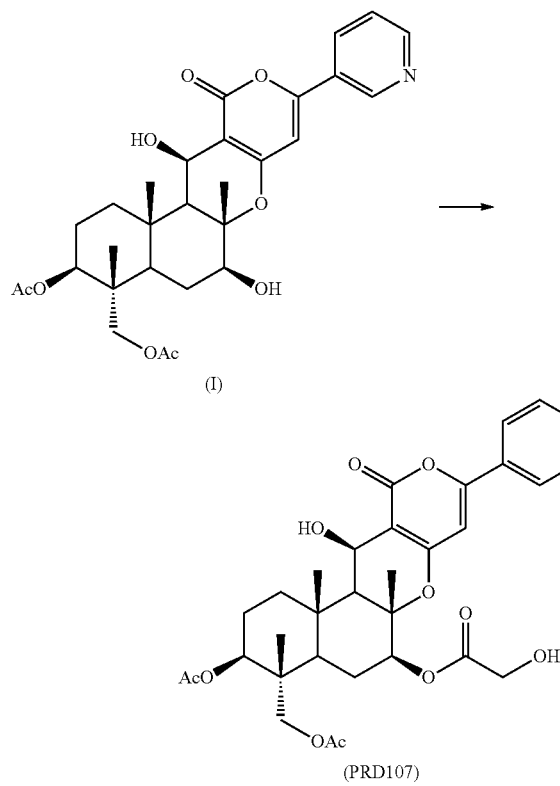

(PRD107)

In an argon atmosphere, EDCI (19 mg, 100 μmol), DMAP (2.2 mg, 18.3 μmol), and crude tert-butyldimethylsiloxyacetic acid (100 μmol) prepared by the method described in the literature (Tetrahedron 2002, 58, 7663) were added to a solution of compound I (20 mg, 36.6 μmol) in $CH_2Cl_2$ (0.5 mL) and stirred for 0.5 hours at room temperature. The reaction mixture was diluted with EtOAc, and the organic layer was washed with 1N HCl and water and dried over anhydrous sodium sulfate. The solution was filtered, and the filtrate was concentrated at a reduced pressure. The resulting residue was purified by neutral flash silica gel column chromatography (1×4, MeOH in $CH_2Cl_2$ 0.5-1.5%) to give 7-O-tert-butyldimethylsiloxyacetyl-7-deacetylpyripyropene A (15.2 mg). To a solution of this 7-O-tert-butyldimethylsiloxyacetyl-7-deacetylpyripyropene A (15.2 mg) in THF (0.5 mL), $Et_3N.3HF$ (7 mL, 42.6 μmol) was added and stirred for 8 hours at room temperature. The reaction mixture was concentrated, and the resulting residue was purified by PTLC (MeOH in $CH_2Cl_2$ 7%) to give PRD 107 (9.6 mg, 2 steps 76%) as a white solid.

$^1$H NMR ($CDCl_3$, 300 MHz) δ 9.01 (dd, 1H, H-2", J=0.6, 2.4 Hz), 8.71-8.68 (m, 1H, H-6"), 8.12-8.08 (m, 1H, H-4"), 7.43-7.39 (m, 1H, H-5"), 6.46 (s, 1H, H-5'), 5.12 (dd, 1H, H-7, J=5.1, 11.8 Hz), 5.00 (d, 1H, H-13, J=3.9 Hz), 4.84-4.78 (m, 1H, H-1), 4.32 (d, 1H, ½$COCH_2OH$, J=17.4 Hz), 4.24 (d, 1H, ½$COCH_2OH$, J=17.4 Hz), 3.79 (d, 1H, H-11a, J=12.0 Hz), 3.66 (d, 1H, H-11b, J=12.0 Hz), 2.20-1.25 (m, 8H, H-2, 3, 5, 8, 9), 2.10 (s, 3H, Ac), 2.05 (s, 3H, Ac), 1.69 (s, 3H, Me), 1.45 (s, 3H, Me), 0.90 (s, 3H, Me).

ESI-LRMS m/z 600 ($MH^+$). ESI-HRMS (MeOH) calcd. for $C_{31}H_{38}NO_{11}$ 600.2445 ($MH^+$). found 600.2420 ($MH^+$).

Example 60

Preparation of 7-O-5-hydroxypentanoyl-7-deacetylpyripyropene A (PRD 093)

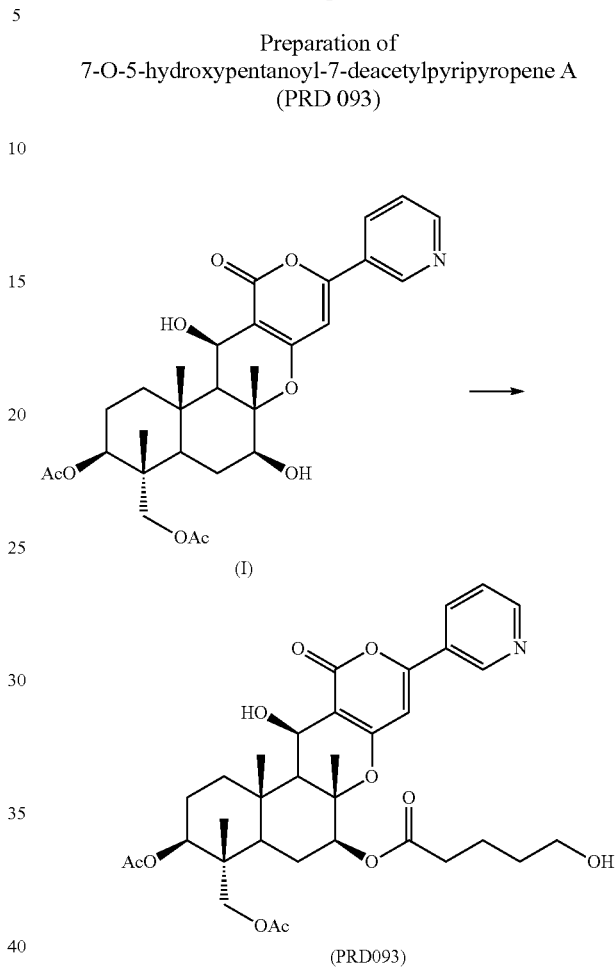

(PRD093)

In an argon atmosphere, EDCI (16 mg, 82.5 μmol), DMAP (2.2 mg, 18.3 μmol), and 6-tert-butyldiphenylsiloxypentanoic acid (22 mg, 61.8 μmol) were added to a solution of compound I (15 mg, 27.5 μmol) in $CH_2Cl_2$ (0.5 mL) and stirred for 4.5 hours at room temperature. The reaction mixture was diluted with EtOAc, and the organic layer was washed with 1N HCl and water and dried over anhydrous sodium sulfate. The solution was filtered, and the filtrate was concentrated at a reduced pressure. The resulting residue was purified by neutral flash silica gel column chromatography (1×4, MeOH in $CH_2Cl_2$ 0.5-1.5%) to give 7-O-5-tert-butyldiphenylsiloxypentanoyl-7-deacetylpyripyropene A (25 mg). To a solution of this 7-O-5-tert-butyldiphenylsiloxypentanoyl-7-deacetylpyripyropene A (25 mg) in THF (0.5 mL), TBAF (0.1M solution in THF, 42 mL, 42.0 μmol) and acetic acid (3.0 mL, 42.0 μmol) were added and stirred for 20 hours at room temperature. The reaction mixture was concentrated, and the resulting residue was purified by PTLC (MeOH in $CH_2Cl_2$ 7%) to give PRD 093 (11.3 mg, 2 steps 63%) as a white solid.

$^1$H NMR ($CDCl_3$, 300 MHz) δ 9.03 (d, 1H, H-2", J=2.4 Hz), 8.07 (dd, 1H, H-6", J=1.8, 4.8 Hz), 8.13-8.10 (m, 1H, H-4"), 7.42-7.38 (m, 1H, H-5"), 6.55 (s, 1H, H-5'), 5.05-4.99 (m, 2H, H-7, 13), 4.80 (dd, 1H, H-1, J=4.8, 11.1 Hz), 3.81-3.69 (m, 4H, H-11, $CH_2OH$), 2.48 (t, 2H, $COCH_2$, J=7.5 Hz), 2.19-1.24 (m, 12H, H-2, 3, 5, 8, 9, COCH$_2$(CH$_2$)$_2$CH$_2$OH), 2.09 (s, 3H, Ac), 2.05 (s, 3H, Ac), 1.70 (s, 3H, Me), 1.45 (s, 3H, Me), 0.89 (s, 3H, Me).

ESI-LRMS m/z 664 (MH$^+$). ESI-HRMS (MeOH) calcd. for C$_{34}$H$_{43}$NNaO$_{11}$ 664.2734 (M+Na$^+$). found 664.2706 (M+Na$^+$).

Example 61

Preparation of 1,11-O-benzylidene-7-O-o-cyanobenzoyl-1,7,11-trideacetylpyripyropene A (PRD 039)

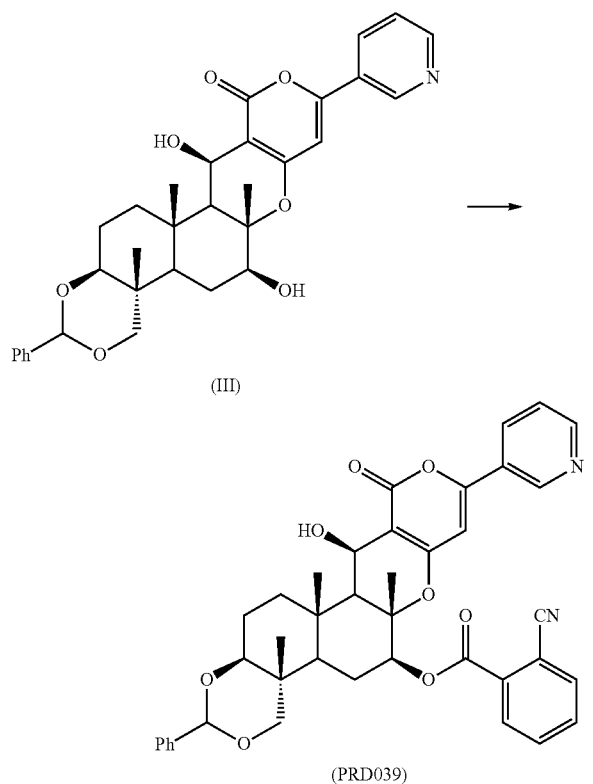

(III)

(PRD039)

In an argon atmosphere, EDCI (28.1 mg, 146 μmol), o-cyanobenzoic acid (10.8 mg, 73.4 μmol), and DMAP (2.2 mg, 18.3 μmol) were added to a solution of compound III (10 mg, 18.5 μmol) in CH$_2$Cl$_2$ (0.5 mL) and stirred for 0.5 hours at room temperature. The reaction mixture was diluted with EtOAc, and the organic layer was washed with water and dried over anhydrous sodium sulfate. The solution was filtered, and the filtrate was concentrated at a reduced pressure. The resulting residue was purified by neutral flash silica gel column chromatography (1×5, MeOH in CH$_2$Cl$_2$ 0.75-2%) to give PRD 039 (10.8 mg, 88%) as a white solid.

$^1$H NMR (CDCl$_3$, 300 MHz) δ 9.00 (d, 1H, H-2", J=1.8 Hz), 8.69 (dd, 1H, H-6", J=1.5, 4.8 Hz), 8.24-8.21 (m, 1H, H—Ar), 8.12-8.09 (m, 1H, H-4"), 7.90-7.87 (m, 1H, H—Ar), 7.79-7.70 (m, 2H, H—Ar), 7.53-7.50 (m, 2H, H—Ar), 7.43-7.34 (m, 4H, H-5", Ar), 6.48 (s, 1H, H-5'), 5.56 (s, 1H, H-benzyl), 5.39 (dd, 1H, H-7, J=5.4, 11.7 Hz), 5.05 (d, 1H, H-13, J=4.5 Hz), 3.91 (d, 1H, H-11a, J=10.5 Hz), 3.57-3.51 (m, 2H, H-11b, 1), 2.75 (br s, 1H, OH-13), 2.29 (d, 1H, H-3a, J=13.2 Hz), 2.04-1.20 (m, 7H, H-2, 3b, 5, 8, 9), 1.88 (s, 3H, Me), 1.53 (s, 3H, Me), 1.29 (s, 3H, Me).

$^{13}$C NMR (CDCl$_3$, 150 MHz) δ 163.92, 163.32, 162.06, 157.29, 151.35, 146.64, 138.21, 135.04, 133.15, 132.99, 132.61, 132.41, 131.24, 129.03, 128.36, 127.20, 126.28, 123.71, 117.58, 113.10, 103.00, 102.81, 99.44, 85.62, 83.38, 80.08, 78.25, 60.27, 60.12, 54.69, 48.97, 38.38, 37.99, 37.03, 36.53, 29.67, 24.99, 23.11, 18.22, 16.94, 13.28.

FAB-LRMS m/z 675 (MH$^+$); FAB-HRMS (CHCl$_3$) calcd. for C$_{40}$H$_{39}$N$_2$O$_8$ 675.2706 (MH$^+$). found 675.2683 (MH$^+$).

Example 62

Preparation of 1,11-O-benzylidene-7-O-m-cyanobenzoyl-1,7,11-trideacetylpyripyropene A (PRD 040)

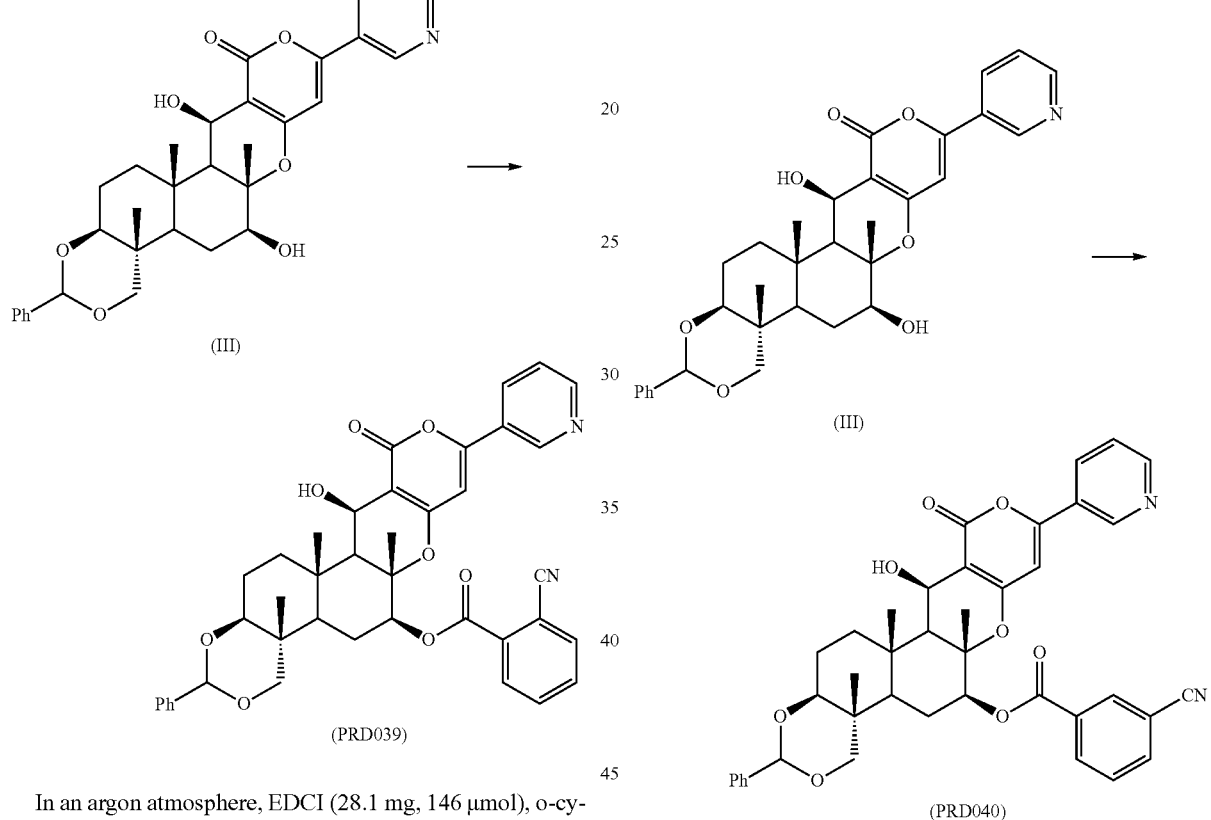

(III)

(PRD040)

In the same manner as in Example 38, PRD 040 (8.0 mg, 65%) was obtained as a white solid from compound III (10 mg, 18.3 μmol).

$^1$H NMR (CDCl$_3$, 300 MHz) δ 8.98 (dd, 1H, H-2", J=0.6, 2.4 Hz), 8.67 (dd, 1H, J=1.8, 4.8 Hz), 8.40-8.33 (m, 2H, H—Ar), 8.10-8.06 (m, 1H, H-4"), 7.92-7.89 (m, 1H, H—Ar), 7.69-7.63 (m, 1H, H—Ar), 7.53-7.49 (m, 2H, H—Ar), 7.41-7.34 (m, 4H, H-5", Ar), 6.42 (s, 1H, H-5'), 5.56 (s, 1H, H-benzyl), 5.35-5.29 (m, 1H, H-7), 5.05 (d, 1H, H-13, J=4.2 Hz), 3.90 (d, 1H, H-11a, J=10.5 Hz), 3.57-3.51 (m, 2H, H-11b, 1), 3.00 (br s, 1H, OH-13), 2.29 (d, 1H, H-3a, J=12.9 Hz), 2.01-1.25 (m, 7H, H-2, 3b, 5, 8, 9), 1.87 (s, 3H, Me), 1.53 (s, 3H, Me), 1.27 (s, 3H, Me).

$^{13}$C NMR (CDCl$_3$, 150 MHz) δ 163.88, 163.72, 161.97, 157.45, 151.54, 146.75, 138.16, 136.33, 133.81, 133.36, 133.02, 131.38, 129.65, 129.06, 127.08, 123.64, 117.78, 113.20, 103.00, 102.83, 99.25, 85.62, 83.36, 79.35, 78.16, 60.09, 54.69, 48.84, 38.37, 37.06, 36.50, 25.06, 23.10, 18.21, 16.73, 13.26.

FAB-LRMS m/z 675 (MH+); FAB-HRMS (CHCl3) calcd. for C40H39N2O8 675.2706 (MH+). found 265.2679 (MH+).

Example 63

Preparation of 1,11-O-benzylidene-7-O-p-cyanobenzoyl-1,7,11-trideacetylpyripyropene A (PRD 041)

Example 64

Preparation of 1,11-O-benzylidene-7-O-o-methoxybenzoyl-1,7,11-trideacetylpyripyropene A (PRD 042)

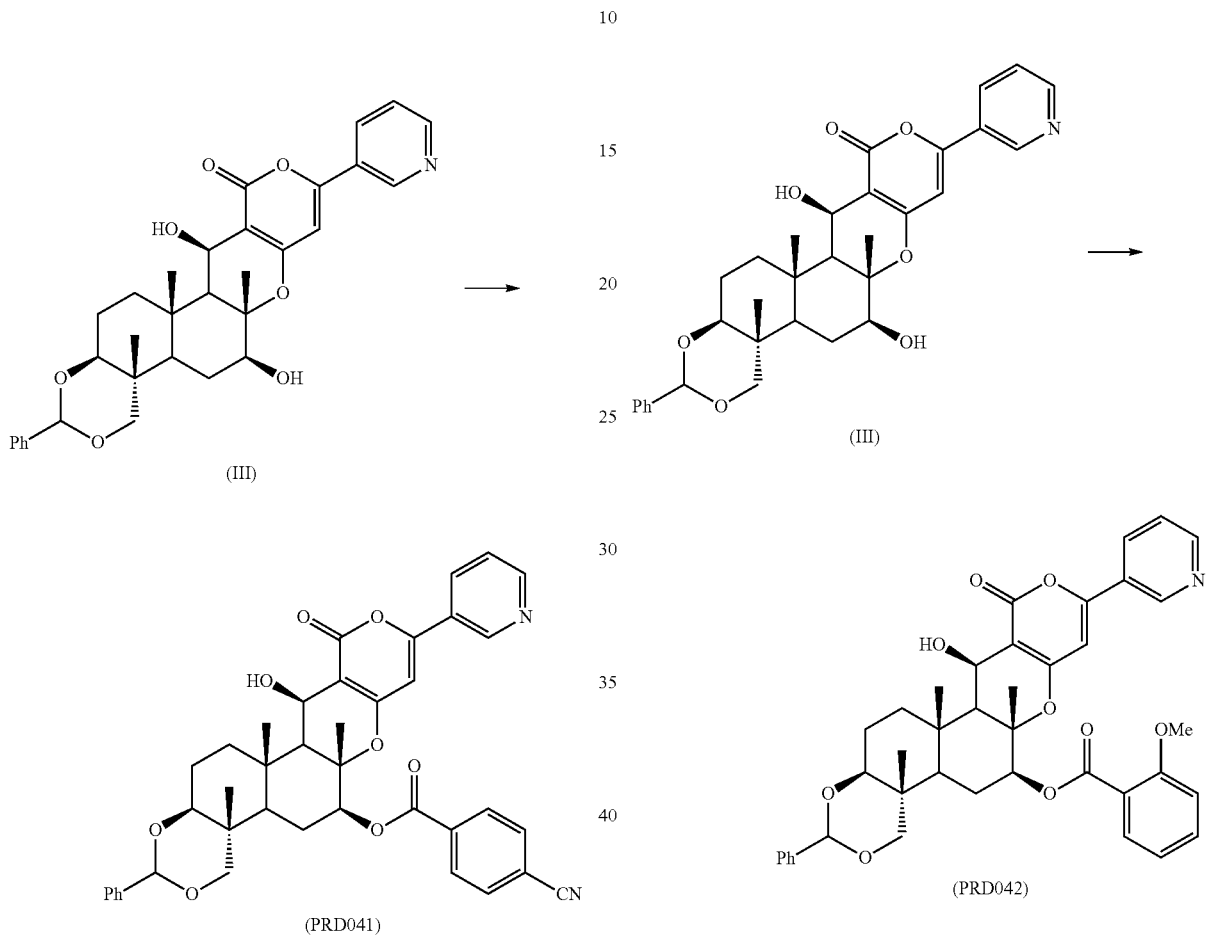

In the same manner as in Example 38, PRD 041 (8.0 mg, 65%) was obtained as a white solid from compound III (10 mg, 18.3 μmol).

$^1$H NMR (CDCl3, 300 MHz) δ 8.97 (d, 1H, H-2", J=2.1 Hz), 8.67 (dd, 1H, H-6", J=1.8, 4.8 Hz), 8.22 (d, 2H, H—Ar, J=8.4 Hz), 8.09-8.06 (m, 1H, H-4"), 7.80 (d, 2H, H—Ar, J=8.4 Hz), 7.53-7.49 (m, 2H, H—Ar), 7.49-7.34 (m, 4H, H-5", Ar), 6.42 (s, 1H, H-5'), 5.56 (s, 1H, H-benzyl), 5.31 dd, 1H, H-7, J=6.0, 11.4 Hz), 5.05 (d, 1H, H-13, J=4.2 Hz), 3.90 (d, 1H, H-11a, J=10.5 Hz), 3.57-3.51 (m, 2H, H-11b, 1), 3.12 (br s, 1H, OH-13), 2.29 (d, 1H, H-3a, J=12.9 Hz), 2.00-1.17 (m, 7H, H-2, 3b, 5, 8, 9), 1.86 (s, 3H, Me), 1.53 (s, 3H, Me), 1.26 (s, 3H, Me).

$^{13}$C NMR (CDCl3, 150 MHz) δ 164.04, 163.86, 161.97, 157.41, 151.52, 146.70, 138.15, 133.83, 133.03, 132.37, 130.25, 129.04, 128.37, 127.08, 126.25, 123.67, 117.81, 116.80, 103.00, 102.82, 99.24, 85.61, 83.36, 79.35, 78.16, 60.08, 54.68, 48.82, 40.29, 38.36, 37.05, 36.49, 29.67, 25.04, 23.09, 18.19, 17.23, 16.69, 13.26.

FAB-LRMS m/z 675 (MH+); FAB-HRMS (CHCl3) calcd. for C40H39N2O8 675.2706 (MH+). found 675.2678 (MH+).

In the same manner as in Example 38, PRD 042 (6.1 mg, 49%) was obtained as a white solid from compound III (10 mg, 18.3 μmol).

$^1$H NMR (CDCl3, 300 MHz) δ 8.99 (dd, 1H, H-2", J=0.9, 2.4 Hz), 8.67 (dd, 1H, H-6", J=1.8, 4.8 Hz), 8.10-8.07 (m, 1H, H-4"), 7.96 (dd, 1H, H—Ar, J=1.8, 7.8 Hz), 7.57-7.50 (m, 3H, H—Ar), 7.41-7.34 (m, 4H, H-5", Ar), 7.07-7.02 (m, 2H, H—Ar), 6.46 (s, 1H, H-5'), 5.55 (s, 1H, H-benzyl), 5.30-5.29 (m, 1H, H-7), 5.04 (d, 1H, H-13, J=1.5 Hz), 3.95-3.90 (m, 4H, H-11a, OMe), 3.55-3.49 (m, 2H, H-11b, 1), 2.94 (br s, 1H, OH-13), 2.26 (d, 1H, H-3a, J=12.9 Hz), 1.87-1.22 (m, 7H, H-2, 3b, 5, 8, 9), 1.85 (s, 3H, Me), 1.51 (s, 3H, Me), 1.26 (s, 3H, Me).

$^{13}$C NMR (CDCl3, 150 MHz) δ 164.98, 164.01, 162.28, 159.78, 157.31, 151.53, 146.83, 142.05, 138.27, 134.22, 132.95, 132.09, 129.02, 128.36, 127.17, 126.29, 123.62, 120.20, 119.27, 112.15, 102.89, 102.81, 99.48, 85.68, 83.70, 78.32, 78.15, 60.25, 55.93, 54.71, 48.88, 38.38, 37.11, 36.53, 29.69, 25.09, 23.15, 18.22, 16.67, 13.26.

FAB-LRMS m/z 680 (MH+); FAB-HRMS (CHCl3) calcd. for C40H42NO9 680.2860 (MH+). found 680.2864 (MH+).

Example 65

Preparation of 1,11-O-benzylidene-7-O-m-methoxybenzoyl-1,7,11-trideacetylpyripyropene A (PRD 043)

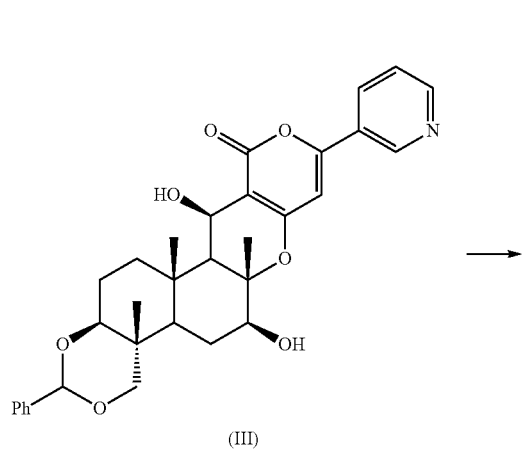

(III)

→

(PRD043)

In the same manner as in Example 38, PRD 043 (7.4 mg, 60%) was obtained as a white solid from compound III (10 mg, 18.3 μmol).

$^1$H NMR (CDCl$_3$, 300 MHz) δ 8.98 (dd, 1H, H-2", J=0.9, 2.4 Hz), 8.67 (dd, 1H, H-6", J=1.8, 5.1 Hz), 8.09-8.05 (m, 1H, H-4"), 7.74-7.70 (m, 1H, H—Ar), 7.64 (dd, 1H, H—Ar, J=1.5, 2.7 Hz), 7.53-7.50 (m, 2H, H—Ar), 7.41-7.34 (m, 5H, H-5", Ar), 7.18-7.14 (m, 1H, H—Ar), 6.43 (s, 1H, H-5'), 5.56 (s, 1H, H-benzyl), 5.30 (dd, 1H, H-7, J=6.0, 10.8 Hz), 5.04 (d, 1H, H-13, J=2.1 Hz), 3.93-3.87 (m, 4H, H-11a, OMe), 3.57-3.51 (m, 2H, H-11b, 1), 2.96 (br s, 1H, OH-13), 2.29 (d, 1H, H-3a, J=12.9 Hz), 1.86-1.26 (m, 7H, H-2, 3b, 5, 8, 9), 1.86 (s, 3H, Me), 1.52 (s, 3H, Me), 1.26 (s, 3H, Me).

$^{13}$C NMR (CDCl$_3$, 150 MHz) δ 165.53, 163.97, 162.16, 159.69, 157.37, 151.56, 146.82, 138.23, 132.95, 131.35, 129.60, 129.04, 128.37, 127.11, 126.28, 123.60, 122.06, 119.51, 114.57, 102.93, 102.82, 99.40, 85.67, 83.59, 78.44, 78.23, 60.19, 55.49, 54.73, 48.84, 38.38, 37.01, 36.52, 29.68, 25.10, 23.13, 18.21, 16.66, 13.26.

FAB-LRMS m/z 680 (MH$^+$); FAB-HRMS (CHCl$_3$) calcd. for C$_{40}$H$_{42}$NO$_9$ 680.2860 (MH$^+$). found 680.2880 (MH$^+$).

Example 66

Preparation of 1,11-O-benzylidene-7-O-p-methoxybenzoyl-1,7,11-trideacetylpyripyropene A (PRD 044)

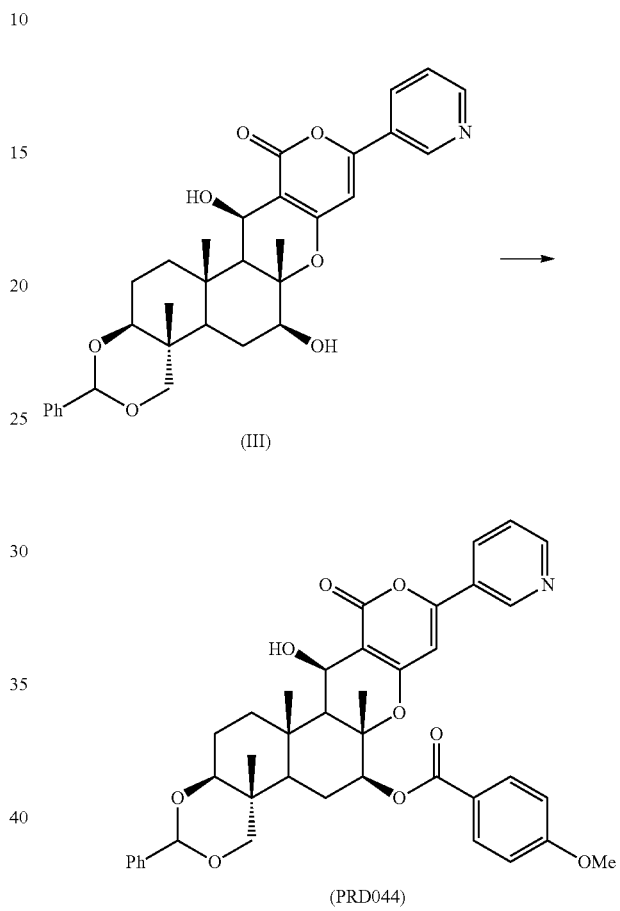

(III)

→

(PRD044)

In the same manner as in Example 38, PRD 044 (4.4 mg, 35%) was obtained as a white solid from compound III (10 mg, 18.3 μmol).

$^1$H NMR (CDCl$_3$, 300 MHz) δ 8.98 (dd, 1H, J=0.3, 2.1 Hz), 8.66 (dd, 1H, H-6", J=1.5, 4.8 Hz), 8.10-8.05 (m, 3H, H-4", Ar), 7.51 (dd, 2H, H—Ar, J=2.1, 7.8 Hz), 7.40-7.34 (m, 4H, H-5", Ar), 6.98 (d, 2H, H—Ar, J=9.0 Hz), 6.43 (s, 1H, H-5'), 5.55 (s, 1H, H-benzyl), 5.30-5.28 (m, 1H, H-7), 5.04 (d, 1H, H-13, J=2.7 Hz), 3.90 (d, 1H, H-11a, J=9.6 Hz), 3.89 (s, 3H, H-OMe), 3.55-3.50 (m, 2H, H-11b, 1), 2.94 (br s, 1H, OH-13), 2.31 (d, 1H, H-3a, J=13.0 Hz), 1.85-1.19 (m, 7H, H-2, 3b, 5, 8, 9), 1.85 (s, 3H, Me), 1.52 (s, 3H, Me), 1.26 (s, 3H, Me).

$^{13}$C NMR (CDCl$_3$, 150 MHz) δ 165.39, 164.00, 163.72, 162.22, 157.33, 151.54, 146.84, 138.26, 132.95, 131.81, 129.03, 128.37, 127.13, 126.29, 123.60, 122.41, 113.81, 102.92, 102.82, 99.45, 85.69, 83.67, 78.26, 77.97, 60.24, 55.52, 54.75, 48.84, 44.43, 38.38, 37.75, 37.12, 36.53, 29.69, 25.20, 23.78, 23.15, 18.22, 16.67, 13.27.

FAB-LRMS m/z 680 (MH$^+$); FAB-HRMS (CHCl$_3$) calcd. for C$_{40}$H$_{42}$NO$_9$ 680.2860 (MH$^+$). found 680.2853 (MH$^+$).

Example 67

Preparation of 1,11-O-benzylidene-7-O-p-nitrobenzoyl-1,7,11-trideacetylpyripyropene A (PRD 045)

Example 68

Preparation of 1,11-O-benzylidene-7-O-o-fluorobenzoyl-1,7,11-trideacetylpyripyropene A (PRD 046)

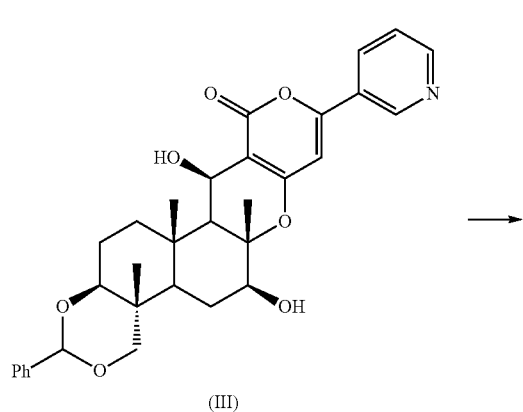

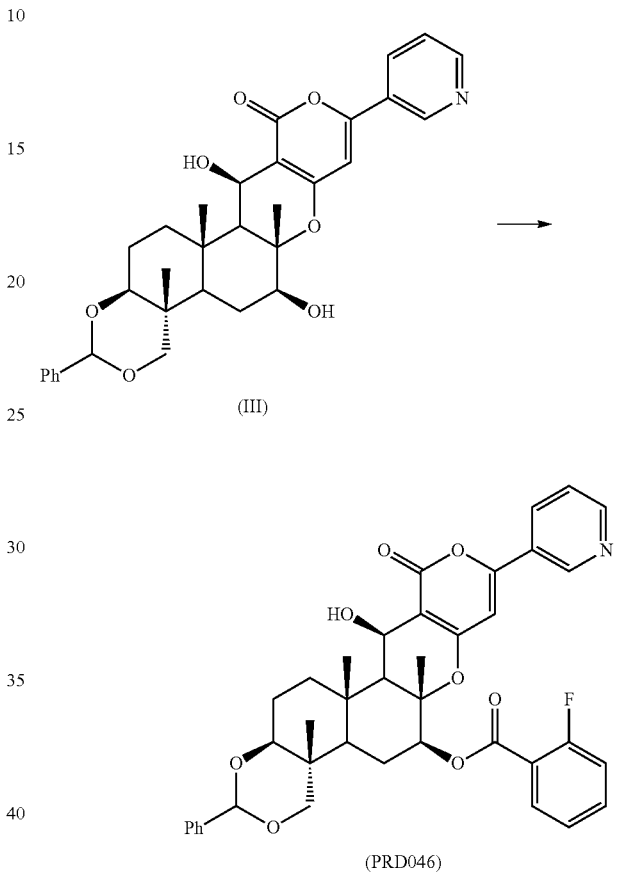

In the same manner as in Example 38, PRD 045 (6.6 mg, 52%) was obtained as a white solid from compound III (10 mg, 18.3 μmol).

$^1$H NMR (CDCl$_3$, 300 MHz) δ 8.98 (d, 1H, H-2", J=1.5 Hz), 8.67 (dd, 1H, H-6", J=1.5, 4.8 Hz), 8.35 (d, 2H, H—Ar, J=9.0 Hz), 8.29 (m, 2H, H—Ar), 8.11-8.07 (m, 1H, H-4"), 7.53-7.50 (m, 2H, H—Ar), 7.49-7.36 (m, 4H, H-5", Ar), 6.41 (s, 1H, H-5'), 5.56 (s, 1H, H-benzyl), 5.32 (dd, 1H, H-7, J=5.7, 11.1 Hz), 5.05 (d, 1H, H-13, J=4.2 Hz), 3.90 (d, 1H, H-11a, J=10.2 Hz), 3.57-3.52 (m, 2H, H-11b, 1), 3.00 (br s, 1H, OH-13), 2.30 (d, 1H, H-3a, J=12.9 Hz), 2.05-1.18 (m, 7H, H-2, 3b, 5, 8, 9), 1.87 (s, 3H, Me), 1.54 (s, 3H, Me), 1.27 (s, 3H, Me).

$^{13}$C NMR (CDCl$_3$, 150 MHz) δ 163.87, 163.82, 161.96, 157.45, 151.53, 150.78, 146.72, 138.16, 135.38, 133.06, 130.89, 129.08, 128.39, 127.10, 126.26, 123.72, 103.02, 102.85, 99.23, 85.62, 83.36, 79.53, 78.17, 62.13, 60.60, 60.11, 54.71, 49.83, 48.86, 43.52, 38.39, 37.07, 36.52, 29.69, 25.06, 23.10, 18.21, 16.72, 13.28.

FAB-LRMS m/z 695 (MH$^+$); FAB-HRMS (CHCl$_3$) calcd. for C$_{39}$H$_{39}$N$_2$O$_{10}$ 695.2605 (MH$^+$). found 695.2599 (MH$^+$).

In the same manner as in Example 38, PRD 046 (11.6 mg, 95%) was obtained as a white solid from compound III (10 mg, 18.3 μmol).

$^1$H NMR (CDCl$_3$, 300 MHz) δ 9.00 (dd, 1H, H-2", J=0.9, 2.4 Hz), 8.68 (dd, 1H, H-6", J=1.5, 4.8 Hz), 8.13-8.02 (m, 3H, H-4", Ar), 7.60-7.50 (m, 4H, H—Ar), 7.43-7.30 (m, 4H, H-5", Ar), 6.47 (s, 1H, H-5'), 5.56 (s, 1H, H-benzyl), 5.30 (dd, 1H, H-7, J=5.7, 11.1 Hz), 5.05 (d, 1H, H-13, J=4.2 Hz), 3.92 (d, 1H, H-11a, J=10.2 Hz), 3.57-3.51 (m, 2H, H-11b, 1), 3.05 (br s, 1H, OH-13), 2.29 (d, 1H, H-3a, J=13.2 Hz), 1.87-1.25 (m, 7H, H-2, 3b, 5, 8, 9), 1.84 (s, 3H, Me), 1.52 (s, 3H, Me), 1.26 (s, 3H, Me).

$^{13}$C NMR (CDCl$_3$, 150 MHz) δ 163.98, 163.65, 162.21, 161.30, 157.23, 151.29, 146.62, 138.23, 134.96 (J=8.7 Hz), 133.17, 132.33, 129.03, 128.36, 127.25, 126.28, 124.13, 123.71, 118.42, 117.29, 117.13, 103.00, 102.82, 99.51, 85.67, 83.52, 78.96, 78.24, 60.16, 54.69, 48.87, 38.38, 37.09, 37.09, 36.52, 29.68, 25.02, 23.12, 18.21, 16.61, 13.26.

FAB-LRMS ink 668 (MH$^+$); FAB-HRMS (CHCl$_3$) calcd. for C$_{39}$H$_{39}$FNO$_8$ 668.2660 (MH$^+$). found 668.2664 (MH$^+$).

Example 69

Preparation of 1,11-O-benzylidene-7-O-m-fluorobenzoyl-1,7,11-trideacetylpyripyropene A (PRD 047)

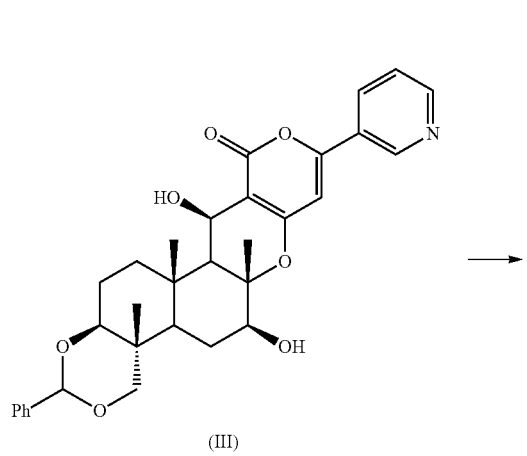

(PRD047)

In the same manner as in Example 38, PRD 047 (11.6 mg, 95%) was obtained as a white solid from compound III (10 mg, 18.3 µmol).

$^1$H NMR (CDCl$_3$, 300 MHz) δ 8.98 (d, 1H, H-2", J=2.4 Hz), 8.67 (dd, 1H, H-6", J=1.5, 4.8 Hz), 8.10-8.06 (m, 1H, H-4"), 7.94-7.91 (m, 1H, H—Ar), 7.81-7.77 (m, 1H, H—Ar), 7.53-7.45 (m, 3H, Ar), 7.41-7.32 (m, 5H, H-5", Ar), 6.43 (s, 1H, H-5'), 5.56 (s, 1H, H-benzyl), 5.32-5.27 (m, 1H, H-7), 5.04 (d, 1H, H-13, J=3.9 Hz), 3.90 (d, 1H, H-11a, J=10.5 Hz), 3.57-3.51 (m, 2H, H-11b, 1), 3.01 (br s, 1H, OH-13), 2.30 (d, 1H, H-3a, J=13.2 Hz), 1.96-1.26 (m, 7H, H-2, 3b, 5, 8, 9), 1.86 (s, 3H, Me), 1.53 (s, 3H, Me), 1.26 (s, 3H, Me).

$^{13}$C NMR (CDCl$_3$, 150 MHz) δ 164.55, 163.93, 163.43, 162.09, 161.79, 157.41, 151.57, 146.81, 138.21, 132.96, 130.23 (J=7.7 Hz), 129.04, 128.37, 127.09, 126.27, 125.48, 123.60, 120.51, 120.38, 116.72, 116.57, 102.95, 102.82, 99.33, 85.65, 83.48, 78.81, 78.21, 60.15, 54.71, 48.84, 38.37, 37.08, 36.51, 25.07, 23.12, 18.20, 16.67, 13.26.

FAB-LRMS m/z 668 (MH$^+$), FAB-HRMS (CHCl$_3$) calcd. for C$_{39}$H$_{39}$FNO$_8$ 668.2660 (MH$^+$). found 668.2664 (MH$^+$).

Example 70

Preparation of 1,11-O-benzylidene-7-O-p-fluorobenzoyl-1,7,11-trideacetylpyripyropene A (PRD 048)

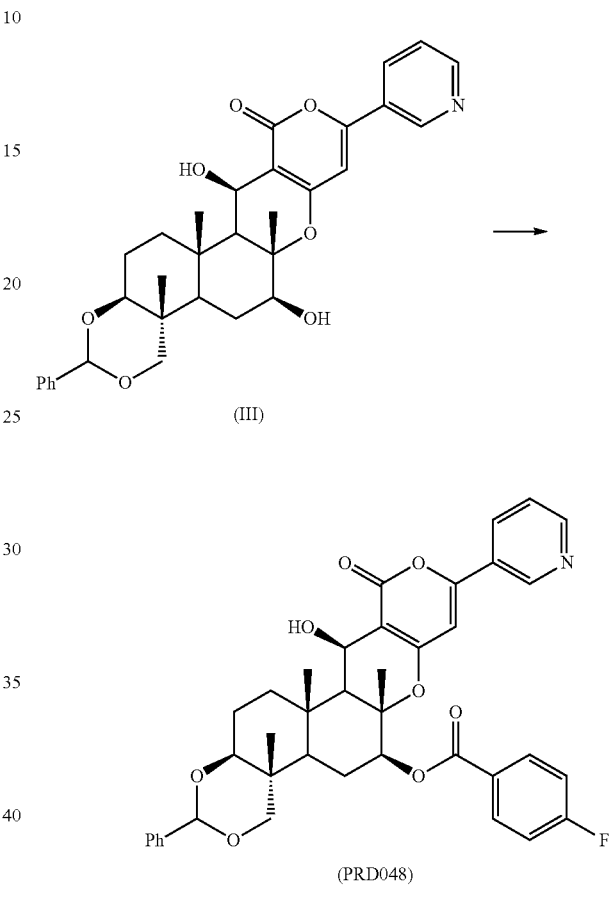

(PRD048)

In the same manner as in Example 38, PRD 048 (12.2 mg, 99%) was obtained as a white solid from compound III (10 mg, 18.3 µmol).

$^1$H NMR (CDCl$_3$, 150 MHz) δ 8.98 (d, 1H, H-2", J=2.4 Hz), 8.67 (dd, 1H, H-6", J=1.5, 4.8 Hz), 8.16-8.12 (m, 2H, H—Ar), 8.09-8.05 (m, 1H, H-4"), 7.53-7.49 (m, 2H, H—Ar), 7.41-7.35 (m, 4H, H-5", Ar), 7.21-7.15 (m, 2H, Ar), 6.42 (s, 1H, H-5'), 5.55 (s, 1H, H-benzyl), 5.30 (dd, 1H, H-7, J=6.3, 11.1 Hz), 5.04 (d, 1H, H-13, J=4.2 Hz), 3.90 (d, 1H, H-11a, J=10.5 Hz), 3.57-3.51 (m, 2H, H-11b, 1), 3.01 (br s, 1H, OH-13), 2.30 (d, 1H, H-3a, J=12.9 Hz), 1.96-1.26 (m, 7H, H-2, 3b, 5, 8, 9), 1.85 (s, 3H, Me), 1.52 (s, 3H, Me), 1.26 (s, 3H, Me).

$^{13}$C NMR (CDCl$_3$, 300 MHz) δ 165.15, 164.69, 163.94, 162.12, 157.40, 151.57, 146.81, 138.21, 132.94, 132.32 (J=9.3 Hz), 129.04, 128.37, 127.08, 126.27, 123.60, 115.82, 115.67, 102.94, 102.82, 99.34, 85.65, 83.52, 78.53, 78.21, 60.16, 54.71, 48.83, 38.37, 37.09, 36.51, 29.68, 25.12, 23.12, 18.20, 16.67, 13.26.

FAB-LRMS m/z 668 (MH$^+$); FAB-HRMS (CHCl$_3$) calcd. for C$_{39}$H$_{39}$FNO$_8$ 668.2660 (MH$^+$). found 668.2635 (MH$^+$).

Example 71

Preparation of 1,11-O-benzylidene-7-O-o-chlorobenzoyl-1,7,11-trideacetylpyripyropene A (PRD 049)

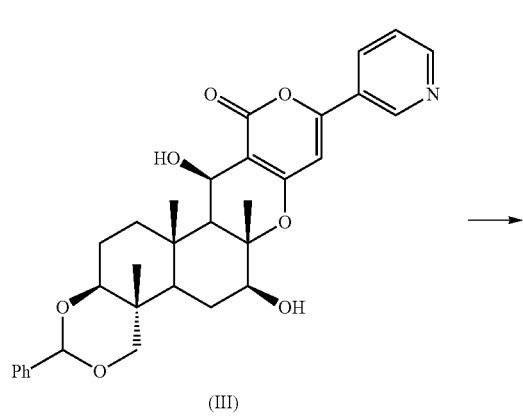

(III)

(PRD049)

In the same manner as in Example 38, PRD 049 (10.4 mg, 83%) was obtained as a white solid from compound III (10 mg, 18.3 μmol).

$^1$H NMR (CDCl$_3$, 300 MHz) δ 9.01 (dd, 1H, H-2″, J=0.9, 2.4 Hz), 8.70 (dd, 1H, H-6″, J=1.5, 3.3 Hz), 8.13-8.09 (m, 1H, H-4″), 7.97-7.94 (m, 1H, H—Ar), 7.54-7.34 (m, 9H, H-5‴, Ar), 6.47 (s, 1H, H-5′), 5.56 (s, 1H, H-benzyl), 5.29 (dd, 1H, H-7, J=7.5, 9.0 Hz), 5.04 (d, 1H, H-13, J=4.2 Hz), 3.93 (d, 1H, H-11a, J=10.2 Hz), 3.57-3.52 (m, 2H, H-11b, 1), 2.71 (br s, 1H, OH-13), 2.29 (d, 1H, H-3a, J=12.9 Hz), 1.90-1.24 (m, 7H, H-2, 3b, 5, 8, 9), 1.83 (s, 3H, Me), 1.51 (s, 3H, Me), 1.27 (s, 3H, Me).

$^{13}$C NMR (CDCl$_3$, 150 MHz) δ 164.78, 163.95, 162.14, 157.32, 151.38, 146.68, 138.24, 134.02, 133.13, 132.98, 131.69, 131.39, 129.72, 129.03, 128.36, 127.21, 126.74, 126.28, 123.70, 102.98, 102.81, 99.44, 85.66, 83.42, 79.34, 78.25, 60.15, 54.71, 48.94, 38.39, 37.07, 36.52, 24.93, 23.12, 18.23, 16.81, 13.28.

FAB-LRMS m/z 684 (MH$^+$); FAB-HRMS (CHCl$_3$) calcd. for C$_{39}$H$_{39}$ClNO$_8$ 684.2364 (MH$^+$). found 684.2363 (MH$^+$).

Example 72

Preparation of 1,11-O-benzylidene-7-O-m-chlorobenzoyl-1,7,11-trideacetylpyripyropene A (PRD 050)

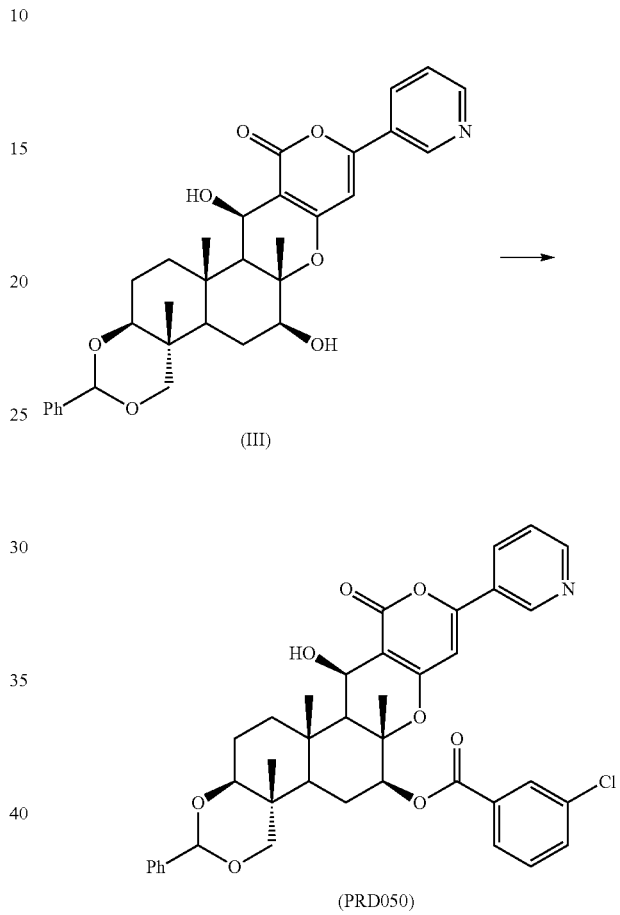

(III)

(PRD050)

In the same manner as in Example 38, PRD 050 (12.0 mg, 96%) was obtained as a white solid from compound III (10 mg, 18.3 μmol).

$^1$H NMR (CDCl$_3$, 300 MHz) δ 8.99 (dd, 1H, H-2″, J=0.6, 2.4 Hz), 8.67 (dd, 1H, H-6″, J=1.8, 4.8 Hz), 8.10-8.06 (m, 2H, H—Ar), 8.03-7.99 (m, 1H, H-4″), 7.62-7.58 (m, 1H, H-5″), 7.58-7.34 (m, 7H, Ar), 6.43 (s, 1H, H-5′), 5.56 (s, 1H, H-benzyl), 5.29 (dd, 1H, H-7, J=6.3, 11.7 Hz), 5.04 (d, 1H, H-13, J=3.9 Hz), 3.90 (d, 1H, H-11a, J=10.5 Hz), 3.57-3.51 (m, 2H, H-11b, 1), 2.98 (br s, 1H, OH-13), 2.29 (d, 1H, H-3a, J=12.9 Hz), 2.02-1.18 (m, 7H, H-2, 3b, 5, 8, 9), 1.86 (s, 3H, Me), 1.53 (s, 3H, Me), 1.26 (s, 3H, Me).

$^{13}$C NMR (CDCl$_3$, 150 MHz) δ 167.46, 163.92, 162.07, 157.41, 151.56, 146.81, 138.20, 134.73, 133.37, 132.95, 131.79, 129.88, 129.79, 129.04, 128.37, 127.87, 127.08, 126.26, 123.60, 102.94, 102.82, 99.33, 85.64, 83.48, 78.82, 78.20, 60.15, 50.79, 54.70, 48.84, 38.37, 37.08, 36.50, 30.90, 25.08, 23.12, 18.20, 26.29, 13.26.

FAB-LRMS m/z 684 (MH$^+$); FAB-HRMS (CHCl$_3$) calcd. for C$_{39}$H$_{39}$ClNO$_8$ 684.2364 (MH$^+$). found 684.2368 (MH$^+$).

Example 73

Preparation of 1,11-O-benzylidene-7-O-p-chlorobenzoyl-1,7,11-trideacetylpyripyropene A (PRD 051)

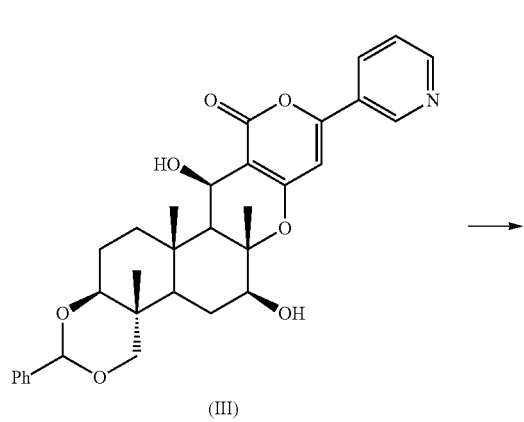

(III)

(PRD051)

In the same manner as in Example 38, PRD 051 (10.9 mg, 87%) was obtained as a white solid from compound III (10 mg, 18.3 μmol).

$^1$H NMR (CDCl$_3$, 300 MHz) δ 8.98 (dd, 1H, H-2", J=0.6, 2.4 Hz), 8.67 (dd, 1H, H-6", J=1.8, 3.9 Hz), 8.09-8.03 (m, 3H, H-4", Ar), 7.53-7.47 (m, 4H, H-5", Ar), 7.41-7.34 (m, 4H, H—Ar), 6.42 (s, 1H, H-5'), 5.56 (s, 1H, H-benzyl), 5.29 (dd, 1H, H-7, J=6.3, 11.1 Hz), 5.04 (d 1H, H-13, J=3.9 Hz), 3.90 (d, 1H, H-11a, J=10.5 Hz), 3.57-3.51 (m, 2H, H-11b, 1), 2.99 (br s, 1H, OH-13), 2.28 (d, 1H, H-3a, J=12.9 Hz), 1.96-1.26 (m, 7H, H-2, 3b, 5, 8, 9), 1.85 (s, 3H, Me), 1.52 (s, 3H, Me), 1.26 (s, 3H, Me).

$^{13}$C NMR (CDCl$_3$, 150 MHz) δ 164.82, 163.93, 162.09, 157.41, 151.57, 146.81, 139.89, 138.20, 132.94, 131.12, 131.12, 129.05, 128.92, 128.48, 128.37, 127.08, 126.27, 123.60, 102.94, 102.82, 99.32, 85.65, 83.50, 78.66, 78.21, 60.15, 54.71, 48.84, 38.37, 37.08, 36.51, 30.15, 29.68, 25.10, 23.12, 21.12, 18.20, 16.67, 13.28, 12.26.

FAB-LRMS m/z 684 (MH$^+$); FAB-HRMS (CHCl$_3$) calcd. for C$_{39}$H$_{39}$ClNO$_8$ 684.2364 (MH$^+$). found 684.2363 (MH$^+$).

Example 74

Preparation of 1,11-O-benzylidene-7-O-m-bromobenzoyl-1,7,11-trideacetylpyripyropene A (PRD 052)

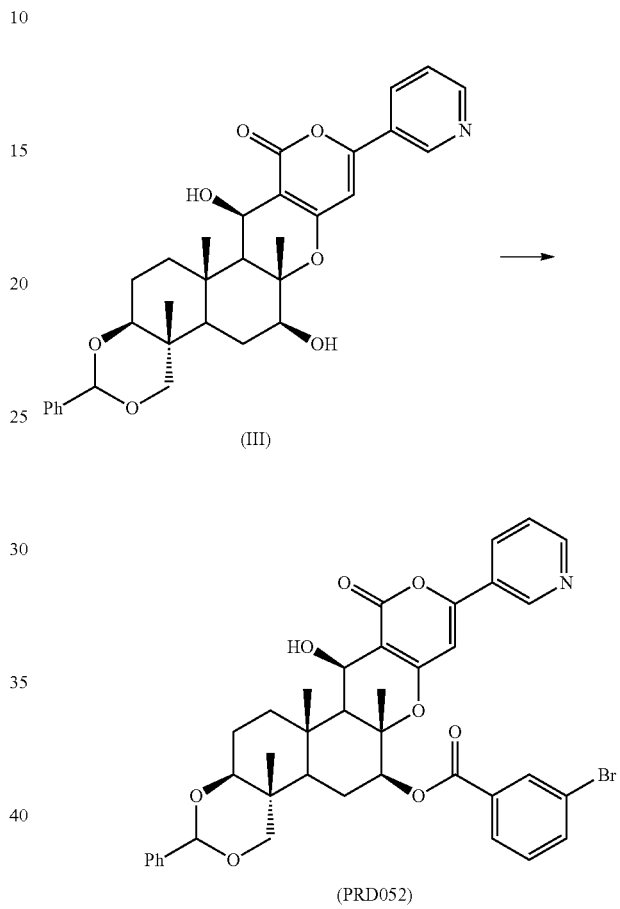

(III)

(PRD052)

In the same manner as in Example 38, PRD 052 (8.6 mg, 58%) was obtained as a white solid from compound III (10 mg, 18.3 μmol).

$^1$H NMR (CDCl$_3$, 300 MHz) δ 8.98 (d, 1H, H-2", J=2.1 Hz), 8.67 (dd, 1H, H-6", J=1.5, 4.8 Hz), 8.24 (t, 1H, H—Ar, J=1.8 Hz), 8.09-8.04 (m, 2H, H-4", Ar), 7.79-7.73 (m, 1H, H—Ar), 7.53-7.50 (m, 2H, Ar), 7.42-7.34 (m, 5H, H-5", Ar), 6.43 (s, 1H, H-5'), 5.56 (s, 1H, H-benzyl), 5.30 (dd, 1H, H-7, J=5.7, 11.4 Hz), 5.04 (s, 1H, H-13), 3.90 (d, 1H, H-11a, J=10.5 Hz), 3.57-3.51 (m, 2H, H-11b, 1), 2.97 (br s, 1H, OH-13), 2.29 (d, 1H, H-3a, J=13.2 Hz), 1.90-1.26 (m, 7H, H-2, 3b, 5, 8, 9), 1.86 (s, 3H, Me), 1.53 (s, 3H, Me), 1.26 (s, 3H, Me).

$^{13}$C NMR (CDCl$_3$, 150 MHz) δ 164.34, 163.94, 162.08, 157.43, 151.59, 146.84, 138.21, 136.30, 132.95, 132.73, 131.99, 130.13, 129.05, 128.37, 128.33, 127.08, 126.27, 124.09, 123.60, 122.65, 102.94, 102.83, 99.33, 85.65, 83.49, 78.84, 78.20, 60.15, 54.71, 54.12, 48.86, 38.38, 37.09, 36.93, 36.52, 29.68, 25.09, 23.12, 18.21, 16.69, 13.26.

FAB-LRMS m/z 728 (MH$^+$); FAB-HRMS (CHCl$_3$) calcd. for C$_{39}$H$_{39}$BrNO$_8$ 728.1859 (MH$^+$). found 728.1861 (MH$^+$).

Example 75

Preparation of 1,11-O-benzylidene-7-O-p-bromobenzoyl-1,7,11-trideacetylpyripyropene A (PRD 053)

Example 76

Preparation of 1,11-O-benzylidene-7-O-p-formylbenzoyl-1,7,11-trideacetylpyripyropene A (PRD 054)

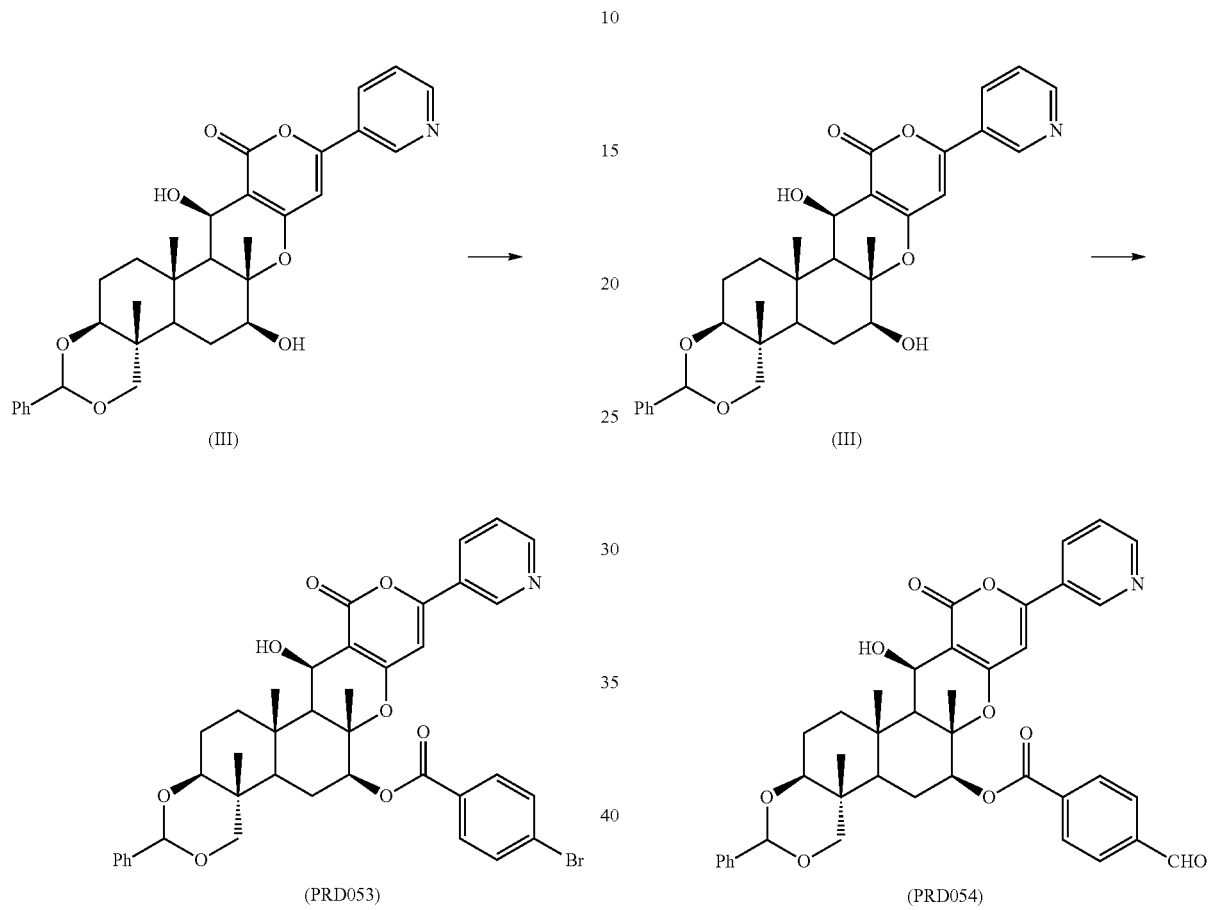

In the same manner as in Example 38, PRD 053 (12.6 mg, 96%) was obtained as a white solid from compound III (10 mg, 18.3 μmol).

$^1$H NMR (CDCl$_3$, 300 MHz) δ 8.98 (d, 1H, H-2", J=2.1 Hz), 8.67 (dd, 1H, H-6", J=1.5, 4.8 Hz), 8.09-8.05 (m, 1H, H-4"), 7.98 (d, 2H, H—Ar, J=8.7 Hz), 7.64 (d, 2H, H—Ar, J=8.7 Hz), 7.53-7.41 (m, 2H, Ar), 7.41-7.33 (m, 4H, H-5", Ar), 6.42 (s, 1H, H-5'), 5.55 (s, 1H, H-benzyl), 5.28 (dd, 1H, H-7, J=5.1, 10.8 Hz), 5.04 (d, 1H, H-13, J=3.9 Hz), 3.90 (d, 1H, H-11a, J=10.5 Hz), 3.56-3.50 (m, 2H, H-11b, 1), 2.97 (br s, 1H, OH-13), 2.28 (d, 1H, H-3a, J=12.5 Hz), 2.05-1.17 (m, 7H, H-2, 3b, 5, 8, 9), 1.85 (s, 3H, Me), 1.52 (s, 3H, Me), 1.26 (s, 3H, Me).

$^{13}$C NMR (CDCl$_3$, 150 MHz) δ 164.95, 163.93, 162.09, 157.39, 151.55, 146.79, 138.20, 134.04, 132.99, 131.92, 131.24, 129.05, 128.93, 128.55, 128.37, 127.10, 126.26, 123.62, 102.95, 102.82, 99.34, 85.65, 83.50, 78.68, 78.20, 60.15, 54.71, 48.84, 38.37, 37.08, 36.51, 31.90, 29.68, 25.09, 23.12, 18.20, 16.91, 16.67, 13.26.

FAB-LRMS m/z 728 (MH$^+$); FAB-HRMS (CHCl$_3$) calcd. for C$_{39}$H$_{39}$BrNO$_8$ 728.1859 (MH$^+$). found 728.1861 (MH$^+$).

In the same manner as in Example 38, PRD 054 (7.7 mg, 62%) was obtained as a white solid from compound III (10 mg, 18.3 μmol).

$^1$H NMR (CDCl$_3$, 300 MHz) δ 10.14 (s, 1H, aldehyde), 8.98 (d, 1H, H-2", J=2.4 Hz), 8.67 (dd, 1H, H-6", J=1.5, 4.8 Hz), 8.28 (d, 2H, H—Ar, J=8.4 Hz), 8.09-8.05 (m, 1H, H-4"), 8.02 (d, 2H, H—Ar, J=8.4 Hz), 7.53-7.50 (m, 2H, Ar), 7.41-7.34 (m, 4H, H-5", Ar), 6.42 (s, 1H, H-5'), 5.56 (s, 1H, H-benzyl), 5.32 (dd, 1H, H-7, J=5.1, 10.8 Hz), 5.05 (d, 1H, H-13, J=3.9 Hz), 3.90 (d, 1H, H-11a, J=10.2 Hz), 3.57-3.52 (m, 2H, H-11b, 1), 2.99 (br s, 1H, OH-13), 2.30 (d, 1H, H-3a, J=13.2 Hz), 2.05-1.24 (m, 7H, H-2, 3b, 5, 8, 9), 1.88 (s, 3H, Me), 1.54 (s, 3H, Me), 1.27 (s, 3H, Me).

$^{13}$C NMR (CDCl$_3$, 150 MHz) δ 191.47, 164.65, 163.91, 162.04, 157.44, 151.57, 146.78, 139.44, 138.18, 134.96, 132.96, 130.36, 129.63, 129.06, 128.37, 127.07, 126.26, 123.62, 102.97, 102.83, 99.28, 85.64, 83.45, 79.11, 78.19, 60.31, 60.13, 58.82, 54.71, 49.73, 48.85, 45.12, 38.38, 37.08, 36.52, 25.08, 23.11, 18.21, 16.71, 13.27.

FAB-LRMS m/z 678 (MH$^+$); FAB-HRMS (CHCl$_3$) calcd. for C$_{40}$H$_{40}$NO$_9$ 678.2703 (MH$^+$). found 678.2703 (MH$^+$).

Example 77

Preparation of 7-(R)-azide-7-(S)-deacetylpyripyropene A (PRD 062)

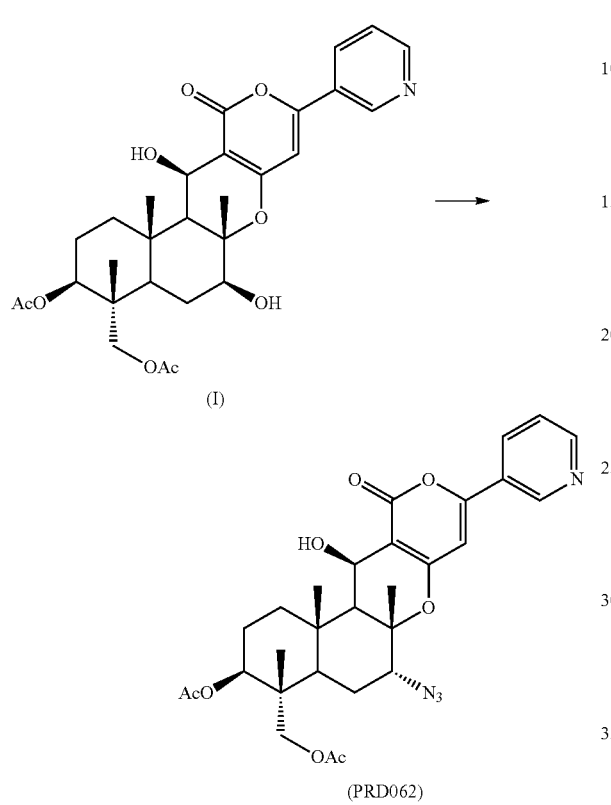

(PRD062)

Example 78

Preparation of 7-(R)-pyripyropene A (PRD 063)

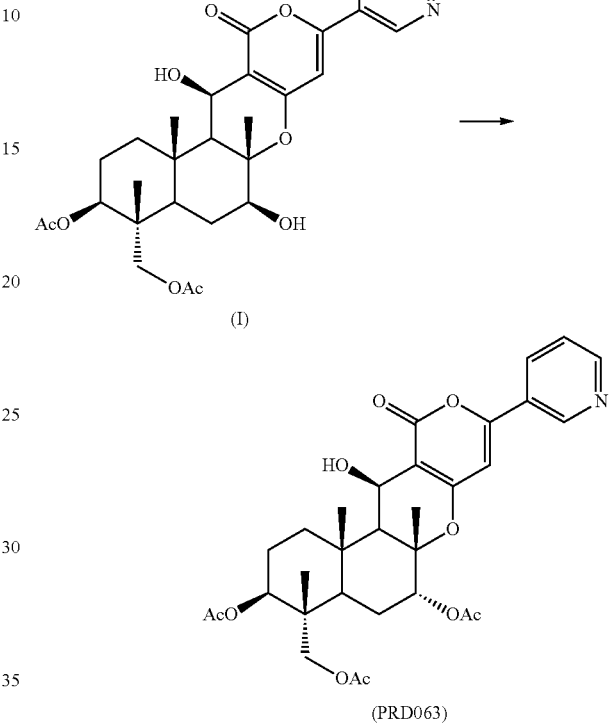

(PRD063)

In an argon atmosphere, Tf$_2$O (7 μl, 41.6 μmol) and DMAP (10.2 mg, 83.1 μmol) were added to a solution of compound I (15 mg, 27.7 μmol) in CH$_2$Cl$_2$ (0.5 mL) at 0° C. and stirred for 3 hours at room temperature. The reaction was terminated by addition of a sodium hydrogen carbonate solution. EtOAc was added to the reaction mixture, and the organic layer was washed with water and dried over anhydrous sodium sulfate. The solution was filtered, and the filtrate was concentrated at a reduced pressure. The resulting residue was dissolved in DMF (0.5 mL), and the resulting solution was stirred for 20 hours at room temperature after addition of NaN$_3$ (9 mg, 139 μmol) thereto. The reaction mixture was diluted with EtOAc, washed with water, and dried over anhydrous sodium sulfate. The resulting residue was purified by neutral flash silica gel column chromatography (0.7×6, MeOH in CH$_2$Cl$_2$ 0.75-1.5%) to give PRD 062 (14 mg, 2 steps, 89%) as a white solid.

$^1$H NMR (CDCl$_3$, 300 MHz) δ 9.03 (dd, 1H, H-2", J=0.6, 2.1 Hz), 8.70 (dd, 1H, H-6", J=1.8, 4.8 Hz), 8.13-8.09 (m, 1H, H-4"), 7.44-7.40 (m, 1H, H-5"), 6.51 (s, 1H, H-5'), 5.03 (d, 1H, H-13, J=3.9 Hz), 4.86 (dd, 1H, H-1, J=4.8, 11.7 Hz), 3.95 (d, 1H, H-11a, J=11.7 Hz), 3.93-3.91 (m, 1H, H-7), 3.57 (d, 1H, H-11b, J=12.0 Hz), 2.89 (br s, 1H, OH-13), 2.11-1.25 (m, 8H, H-2, 3, 5, 8, 9), 2.08 (s, 3H, Ac), 2.05 (s, 3H, Ac), 1.74 (s, 3H, Me), 1.40 (s, 3H, Me), 0.86 (s, 3H, Me).

FAB-LRMS m/z 567 (MTV); FAB-HRMS (CHCl$_3$) calcd. for C$_{29}$H$_{35}$N$_4$O$_8$ 567.2455 (MH$^+$). found 567.2464 (MH$^+$).

In an argon atmosphere, TfCl (4 μl, 41.6 μmol) and DMAP (9.0 mg, 73.2 μmol) were added to a solution of compound I (10 mg, 18.3 μmol) in CH$_2$Cl$_2$ (0.5 mL) and stirred for 1 hour at 0° C. The reaction was terminated by addition of a sodium hydrogen carbonate solution. EtOAc was added to the reaction mixture, and the organic layer was washed with water and dried over anhydrous sodium sulfate. The solution was filtered, and the filtrate was concentrated at a reduced pressure. The resulting residue was dissolved in DMF (0.25 mL) and HMPA (0.25 mL), and the resulting solution was stirred for 18 hours at room temperature after addition of LiOAc (12 mg, 183 μmol) thereto. The reaction mixture was diluted with EtOAc, washed with water, dried over anhydrous sodium sulfate, and then concentrated. The resulting residue was purified by PTLC (hexane:EtOAc=1:2) to give PRD 063 (8.9 mg, 2 steps, 83%) as a white solid.

$^1$H NMR (CDCl$_3$, 300 MHz) δ 8.95 (dd, 1H, H-2", J=0.9, 1.8 Hz), 8.62 (dd, 1H, H-6", J=1.5, 4.8 Hz), 8.06-8.02 (m, 1H, H-4"), 7.37-7.32 (m, 1H, H-5"), 6.64 (s, 1H, H-5'), 4.98 (d, 1H, H-13, J=2.4 Hz), 4.84 (dd, 1H, H-1, J=4.8, 11.4 Hz), 4.37 (t, 1H, H-7, J=3.0 Hz), 3.84 (d, 1H, H-11a, J=12.0 Hz), 3.53 (d, 1H, H-11b, J=12.0 Hz), 2.81 (br s, 1H, OH-13), 2.18-1.36 (m, 8H, H-2, 3, 5, 8, 9), 1.99 (s, 3H, Ac), 1.98 (s, 3H, Ac), 1.71 (s, 3H, Me), 1.38 (s, 3H, Me), 0.82 (s, 3H, Me).

ESI-LRMS m/z 584 (MH$^+$). ESI-HRMS (MeOH) calcd. for C$_{31}$H$_{37}$NNaO$_9$ 583.2417 (M+Na$^+$). found 583.2432 (M+Na$^+$) □.

Example 79

Preparation of 7-(R)-iodo-7-(S)-deacetylpyripyropene A (PRD 064)

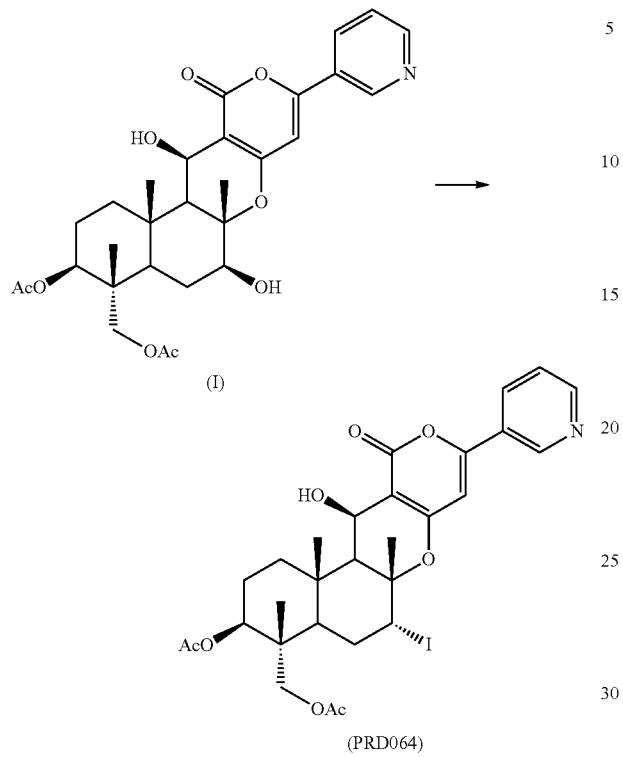

In the same manner as in Example 54, PRD 064 (18 mg, 2 steps, quant.) was obtained as a white solid from compound I (15 mg, 27.5 μmol).

$^1$H NMR (CDCl$_3$, 300 MHz) δ 9.03 (d, 1H, J=2.1 Hz), 8.70 (dd, 1H, H-6", J=1.5, 4.5 Hz), 8.14-8.10 (m, 1H, H-4"), 7.41 (dd, 1H, H-5", J=4.8, 8.1 Hz), 6.51 (s, 1H, H-5'), 5.03 (d, 1H, H-13, J=2.7 Hz), 4.95 (dd, 1H, H-1, J=5.1, 11.4 Hz), 4.85 (t, 1H, H-7, J=3.0 Hz), 3.78 (d, 1H, H-11a, J=12.0 Hz), 3.71 (d, 1H, H-11b, J=12.0 Hz), 2.92 (br s, 1H, OH-13), 2.23-1.45 (m, 8H, H-2, 3, 5, 8, 9), 2.11 (s, 3H, Ac), 2.06 (s, 3H, Ac), 1.83 (s, 3H, Me), 1.47 (s, 3H, Me), 0.91 (s, 3H, Me).

ESI-LRMS m/z 674 (M+Na$^+$). ESI-HRMS (MeOH) calcd. for C$_{29}$H$_{34}$INNaO$_8$ 674.1227 (M+Na$^+$). found 674.1205 (M+Na$^+$).

Example 80

Preparation of 7-(R)-chloro-7-(S)-deacetylpyripyropene A (PRD 065)

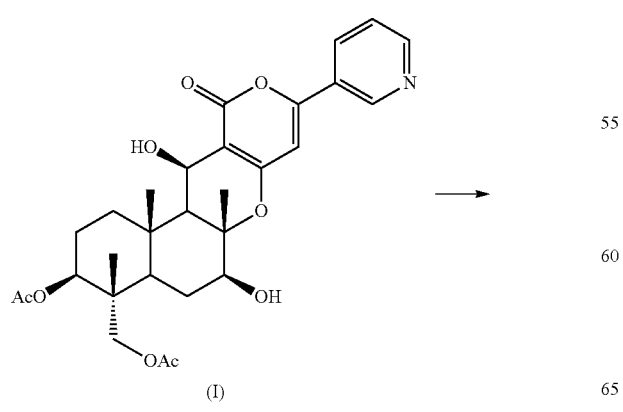

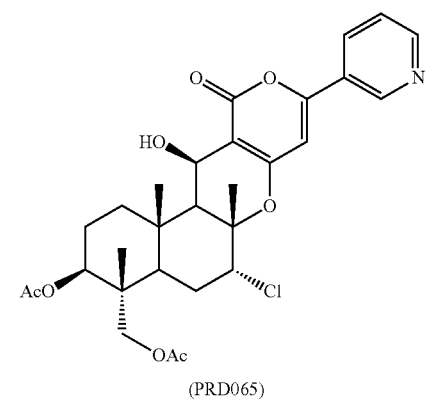

In the same manner as in Example 54, PRD 065 (13.3 mg, 2 steps, 72%) was obtained as a white solid from compound I (15 mg, 27.5 μmol).

$^1$H NMR (CDCl$_3$, 300 MHz) δ 9.02 (dd, 1H, H-2", J=0.9, 2.4 Hz), 8.69 (dd, 1H, H-6", J=1.5, 4.8 Hz), 8.13-8.09 (m, 1H, H-4"), 7.43-7.39 (m, 1H, H-5"), 6.53 (s, 1H, H-5'), 5.05 (d, 1H, H-13, J=3.0 Hz), 4.92 (dd, 1H, H-1, J=4.8, 11.7 Hz), 4.44 (dd, 1H, H-7, J=2.4, 3.0 Hz), 3.91 (d, 1H, H-11a, J=12.0 Hz), 3.60 (d, 1H, H-11b, J=12.0 Hz), 2.92 (br d, 1H, OH-13, J=1.5 Hz), 2.12-1.25 (m, 8H, H-2, 3, 5, 8, 9), 2.06 (s, 3H, Ac), 2.05 (s, 3H, Ac), 1.78 (s, 3H, Me), 1.45 (s, 3H, Me), 0.89 (s, 3H, Me).

ESI-LRMS m/z 582 (M+Na$^+$). ESI-HRMS (MeOH) calcd. for C$_{29}$H$_{34}$ClNNaO$_8$ 582.1871 (M+Na$^+$). found 582.1898 (M+Na$^+$).

Example 81

Preparation of 7-(R)-{sulfinyl-5-(p-methoxyphenyl)tetrazol-1-yl}-7-(S)-deacetylpyripyropene A (PRD 066)

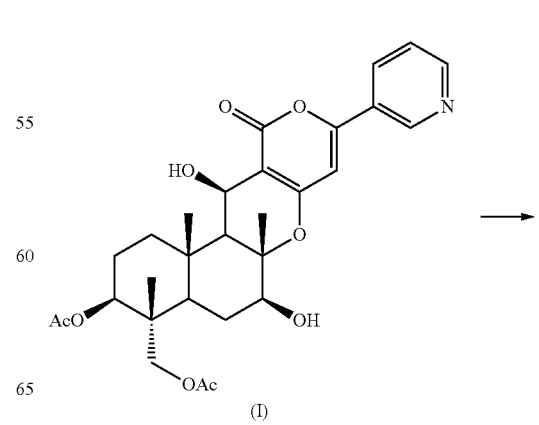

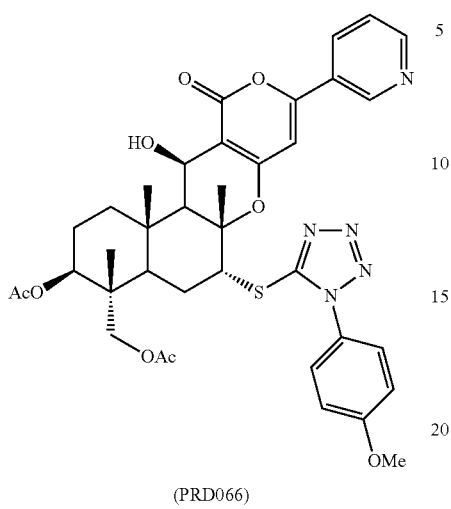

(PRD066)

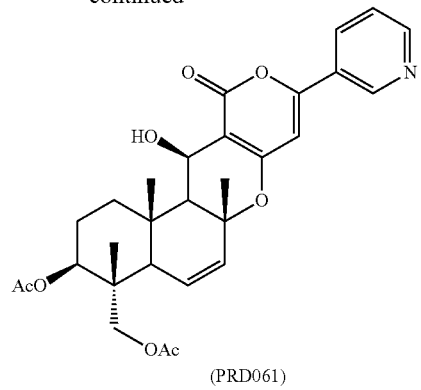

(PRD061)

In the same manner as in Example 54, PRD 066 (10.4 mg, 2 steps, 77%) was obtained as a white solid from compound I (10 mg, 18.3 μmol).

$^1$H NMR (CDCl$_3$, 300 MHz) δ 9.02 (d, 1H, H-2", J=1.8 Hz), 8.70 (dd, 1H, H-6", J=1.5, 4.8 Hz), 8.05-8.01 (m, 1H, H-4"), 7.42-7.37 (m, 4H, H-5", Ar), 7.00 (dd, 1H, H—Ar, J=2.1, 6.9 Hz), 6.06 (s, 1H, H-5'), 5.00 (d, 1H, H-13, J=2.4 Hz), 4.85 (t, 1H, H-7, J=3.0 Hz), 4.77 (dd, 1H, H-1, J=5.7, 11.1 Hz), 3.69 (d, 2H, H-11), 2.84 (br d, 1H, OH-13, J=1.8 Hz), 2.19-1.43 (m, 8H, H-2, 3, 5, 8, 9), 2.04 (s, 3H, Ac), 1.87 (s, 3H, Ac), 1.75 (s, 3H, Me), 1.47 (s, 3H, Me), 0.89 (s, 3H, Me).

ESI-LRMS m/z 754 (M+Na$^+$). ESI-HRMS (MeOH) calcd. for C$_{37}$H$_{41}$N$_5$NaO$_9$S 754.2523 (M+Na$^+$). found 754.2556 (M+Na$^+$).

In an argon atmosphere, 15-crown-5 (1 drop) and NaN$_3$ (14 mg, 207 μmol) were added to a solution of PRD 064 (9 mg, 13.8 μmol) in DMF (0.3 mL) and stirred for 18 hours at 75° C. EtOAc was added to the reaction mixture, and the organic layer was washed with water and dried over anhydrous sodium sulfate. The solution was filtered, and the filtrate was dried over anhydrous sodium sulfate and concentrated. The resulting residue was purified by neutral flash silica gel column chromatography (1×4, MeOH in CH$_2$Cl$_2$ 0.5-1.5%) to give PRD 061 (5.8 mg, 81%) as a white solid.

$^1$H NMR (CDCl$_3$, 300 MHz) δ 9.00 (d, 1H, H-2", J=2.4 Hz), 8.69 (dd, 1H, H-6", J=1.5, 4.8 Hz), 8.13-8.09 (m, 1H, H-4"), 7.41 (dd, 1H, H-5", J=4.8, 8.1 Hz), 6.48 (s, 1H, H-5'), 5.87 (s, 2H, H-7, 8), 4.98 (d, 1H, H-13, J=3.6 Hz), 4.87 (dd, 1H, H-1, J=5.4, 11.4 Hz), 3.88 (d, 1H, H-11a, J=12.0 Hz), 3.81 (d, 1H, H-11b, J=12.0 Hz), 2.78 (br s, 1H, OH-13), 2.33 (s, 1H, H-9), 2.23-1.45 (m, 5H, H-2, 3, 5), 2.05 (s, 3H, Ac), 2.04 (s, 3H, Ac), 1.70 (s, 3H, Me), 1.32 (s, 3H, Me), 0.92 (s, 3H, Me).

ESI-LRMS m/z 546 (M+Na$^+$). ESI-HRMS (MeOH) calcd. for C$_{29}$H$_{33}$NNaO$_8$ 546.2104, (M+Na$^+$). found 546.2087 (M+Na$^+$).

Example 82

Preparation of 7,8-olefinpyripyropene A (PRD 061)

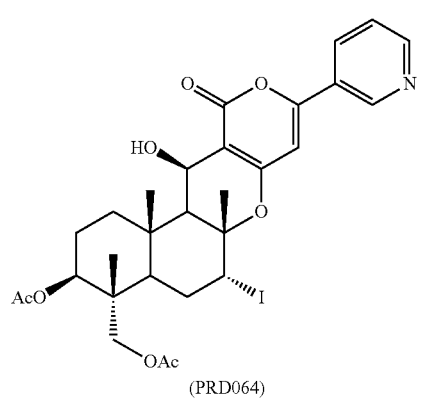

(PRD064)

Example 83

Preparation of 7-deacetyl-7-O-methoxyethoxymethylpyripyropene A (PRD 055)

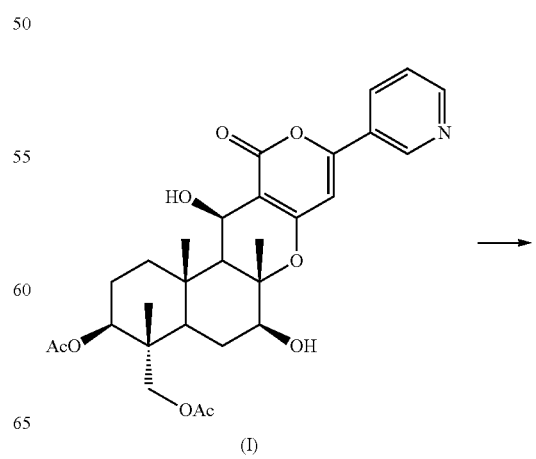

(I)

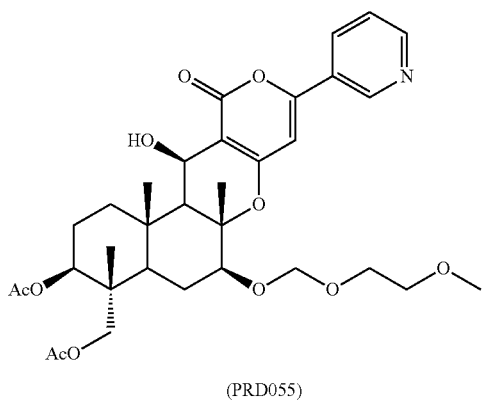

(PRD055)

In an argon atmosphere, DIPEA (6 μL, 37.0 μmol) and MEMCl (3 mL, 22.2 μmol) were added to a solution of compound I (10 mg, 18.5 μmol) in CH$_2$Cl$_2$ (0.5 mL) at 0° C. and stirred for 5 hours at room temperature. MeOH was added to stop the reaction, and the reaction mixture was concentrated at a reduced pressure. The resulting residue was purified by PTLC (MeOH:CH$_2$Cl$_2$=10:1) to give PRD 055 (5.4 mg, 54%) as a white solid.

$^1$H NMR (CDCl$_3$, 300 MHz) δ 9.02 (d, 1H, H-2", J=2.1 Hz), 8.69 (dd, 1H, H-6", J=1.8, 4.8 Hz), 8.13-8.09 (m, 1H, H-4"), 7.43-7.39 (m, 1H, H-5"), 6.55 (s, 1H, H-5'), 4.98 (d, 1H, H-13, J=1.5 Hz), 4.94 (d, 1H, ½OCH$_2$O, J=6.9 Hz), 4.88 (d, 1H, ½OCH$_2$O, J=6.9 Hz), 4.80 (dd, 1H, H-1, J=5.4, 10.8 Hz), 3.91 (dd, 1H, H-7, J=5.1, 9.3 Hz), 3.84 (d, 1H, H-11a, J=11.7 Hz), 3.82-3.71 (m, 3H, H-11b, OCH$_2$CH$_2$OMe), 3.64-3.42 (m, 2H, OCH$_2$CH$_2$OMe), 3.42 (s, 3H, OMe), 2.87 (br s, 1H, OH-13), 2.17-1.31 (m, 8H, H-2, 3, 5, 8, 9), 2.07 (s, 3H, Ac), 2.05 (s, 3H, Ac), 1.65 (s, 3H, Me), 1.42 (s, 3H, Me), 0.90 (s, 3H, Me).

FAB-LRMS m/z 630 (MH$^+$); FAB-HRMS (CHCl$_3$) calcd. for C$_{33}$H$_{44}$NO$_{11}$ 630.2914 (MH$^+$). found 630.2905 (MH$^+$).

Example 84

Preparation of 7-deacetyl-7-O-phenoxycarbonylpyripyropene A (PRD 057)

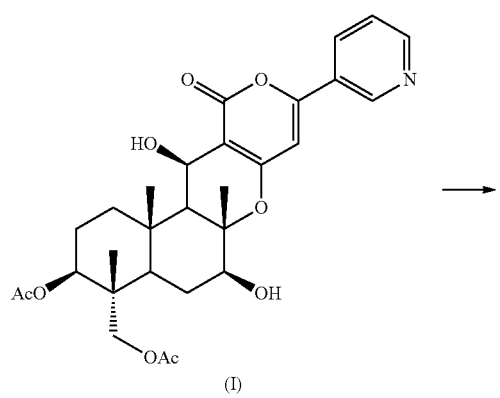

(I)

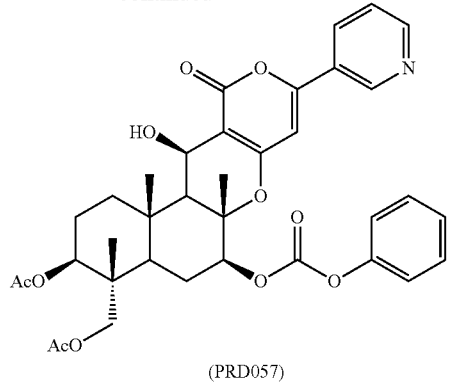

(PRD057)

In an argon atmosphere, Et$_3$N (8 μL, 55.5 μmol), DMAP (2.3 mg, 18.5 μmol), and phenyl chloroformate (4 μL, 27.8 μmol) were added to a solution of compound I (10 mg, 18.5 μmol) in CH$_2$Cl$_2$ (0.5 mL) at 0° C. and stirred for 1.5 hours at room temperature. MeOH was added to stop the reaction. EtOAc was then added to the reaction mixture, and the organic layer was washed with 1N HCl and water and dried over anhydrous sodium sulfate. The solution was filtered, and the filtrate was dried over anhydrous sodium sulfate and then concentrated. The resulting residue was purified by neutral flash silica gel column chromatography (0.7×6, MeOH in CH$_2$Cl$_2$ 0-1.5%) to give PRD 057 (9.7 mg, 80%) as a white solid.

$^1$H NMR (CDCl$_3$, 300 MHz) δ 9.03 (dd, 1H, H-2", J=0.9, 2.4 Hz), 8.70 (dd, 1H, H-6", J=1.5, 4.8 Hz), 8.14-8.10 (m, 1H, H-4"), 7.46-7.40 (m, 3H, H-5", Ar), 7.31-7.24 (m, 3H, Ar), 6.52 (s, 1H, H-5'), 5.02 (d, 1H, H-13, J=1.8 Hz), 4.92 (dd, 1H, H-1, J=5.1, 11.1 Hz), 4.79 (dd, 1H, H-7, J=5.1, 11.1 Hz), 3.86 (d, 1H, H-11a, J=12.0 Hz), 3.69 (d, 1H, H-11b, J=12.0 Hz), 2.98 (br d, 1H, OH-13, J=1.5 Hz), 2.21-1.47 (m, 8H, H-2, 3, 5, 8, 9), 2.05 (s, 6H, Ac), 1.77 (s, 3H, Me), 1.47 (s, 3H, Me), 0.92 (s, 3H, Me).

FAB-LRMS m/z 662 (MH$^+$); FAB-HRMS (CHCl$_3$) calcd. for C$_{36}$H$_{40}$NO$_{11}$ 662.2601 (MH$^+$). found 662.2625 (MH$^+$).

Example 85

Preparation of 7-O-p-chlorophenoxycarbonyl-7-deacetylpyripyropene A (PRD 058)

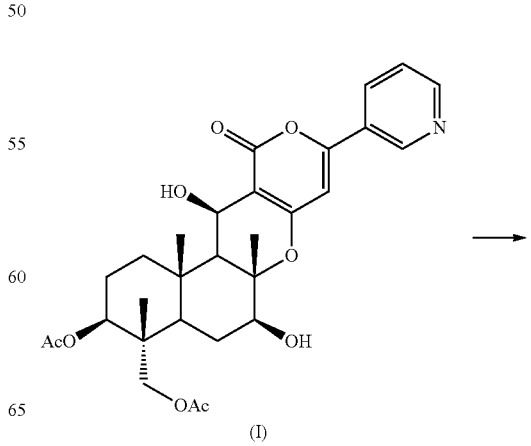

(I)

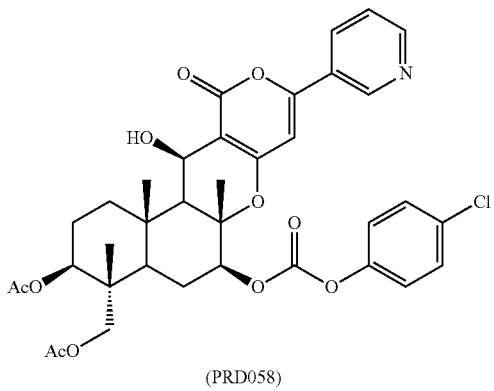

(PRD058)

In the same manner as in Example 59, PRD 058 (8.7 mg, 67%) was obtained as a yellow solid from compound I (10 mg, 18.3 μmol).

$^1$H NMR (CDCl$_3$, 300 MHz) δ 9.02 (dd, 1H, H-2″, J=0.6, 2.4 Hz), 8.70 (dd, 1H, H-6″, J=1.8, 5.1 Hz), 8.14-8.10 (m, 1H, H-4″), 7.45-7.36 (m, 3H, H-5″, Ar), 7.24-7.20 (m, 2H, Ar), 6.51 (s, 1H, H-5′), 5.02 (d, 1H, H-13, J=3.0 Hz), 4.91 (dd, 1H, H-1, J=5.1, 11.7 Hz), 4.80 (dd, 1H, H-7, J=4.8, 11.1 Hz), 3.84 (d, 1H, H-11a, J=12.0 Hz), 3.71 (d, 1H, H-11b, J=12.0 Hz), 2.97 (br s, 1H, OH-13), 2.21-1.26 (m, 8H, H-2, 3, 5, 8, 9), 2.05 (s, 6H, Ac), 1.77 (s, 3H, Me), 1.47 (s, 3H, Me), 0.92 (s, 3H, Me).

FAB-LRMS m/z 696 (MH$^+$); FAB-HRMS (CHCl$_3$) calcd. for C$_{36}$H$_{39}$ClNO$_{11}$ 696.2212 (MH$^+$). found 696.2235 (MH$^+$).

Example 86

Preparation of 7-O-p-cyanobenzoyl-1,1′-O-(di-tert-butylsilylene)-1,7,11-trideacetylpyripyropene A (PRD 059) and 7,13-di-(O-p-cyanobenzoyl)-1,1′-O-(di-tert-butylsilylene)-1,7,11-trideacetylpyripyropene A (PRD 060)

a) Preparation of 1,11-O-(di-tert-butylsilylene)-1,7,11-trideacetylpyripyropene A

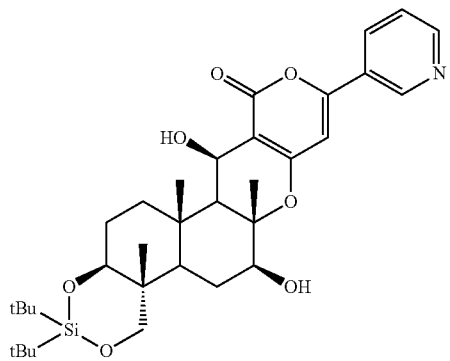

In an argon atmosphere, 2,6-lutidine (103 mL, 0.88 mmol) and $^t$Bu$_2$Si(OTf)$_2$ (161 ml, 0.44 mmol) were added to a solution in dried DMF (4 mL) of 1,7,11-trideacetylpyripyropene A (168 mg, 0.367 mmol) prepared by the method of Obata et al., (J. Antibiot., vol. 49, pp. 11494156, 1996) and stirred for 0.5 hours at 0° C. MeOH was added to stop the reaction. EtOAc was added to the reaction mixture, and the organic layer was washed with 1N HCl and water and dried over anhydrous sodium sulfate. The solution was filtered, and the filtrate was dried over anhydrous sodium sulfate and concentrated. The resulting residue was purified by neutral flash silica gel column chromatography (3×10, MeOH in CH$_2$Cl$_2$ 0-3%) to give 1,11-O-(di-tert-butylsilylene)-1,7,11-trideacetylpyripyropene A (220 mg, quant.) as a white foam.

$^1$H NMR (CDCl$_3$, 300 MHz) δ 8.99 (d, 1H, H-2″, J=2.4 Hz), 8.68 (dd, 1H, H-6″, J=1.5, 4.8 Hz), 8.13-8.09 (m, 1H, H-4″), 7.44-7.40 (m, 1H, H-5″), 6.50 (s, 1H, H-5′), 5.31 (t, 1H, H-13, J=3.0 Hz), 3.93-3.73 (m, 4H, H-1, 7, 11), 3.26 (br s, 1H, OH-13), 2.85 (br s, 1H, OH-7), 2.18-1.26 (m, 8H, H-2, 3, 5, 8, 9), 1.66 (s, 3H, Me), 1.40 (s, 3H, Me), 1.14 (s, 3H, Me), 1.09 (s, 9H, $^t$Bu), 1.05 (s, 9H, $^t$Bu).

b) Preparation of 7-O-p-cyanobenzoyl-1,11-O-(di-tert-butylsilylene)-1,7,11-trideacetylpyripyropene A (PRD 059) and 7,13-di-(O-p-cyanobenzoyl)-1,11-O-(di-tert-butylsilylene)-1,7,11-trideacetylpyripyropene A (PRD 060)

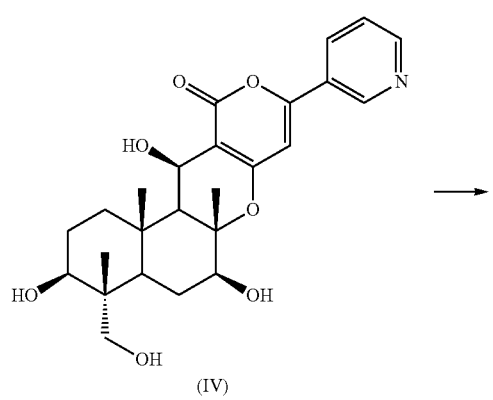

(IV)

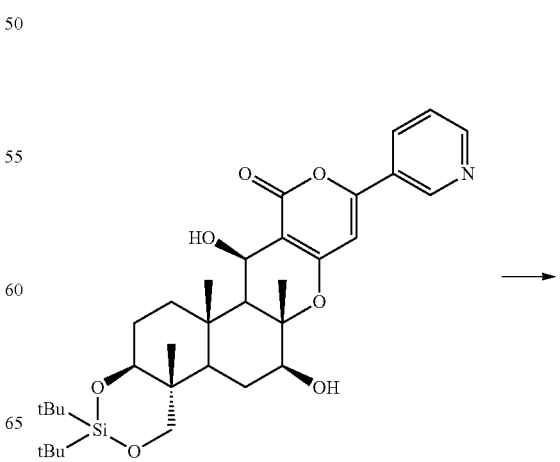

-continued

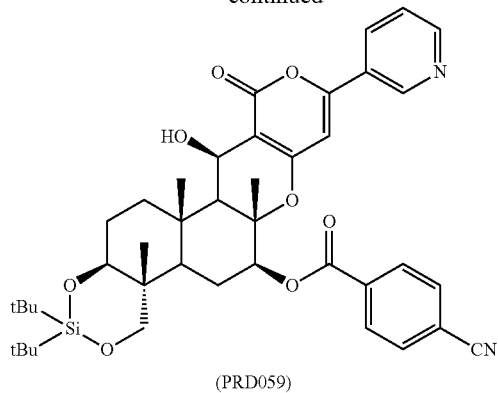

(PRD059)

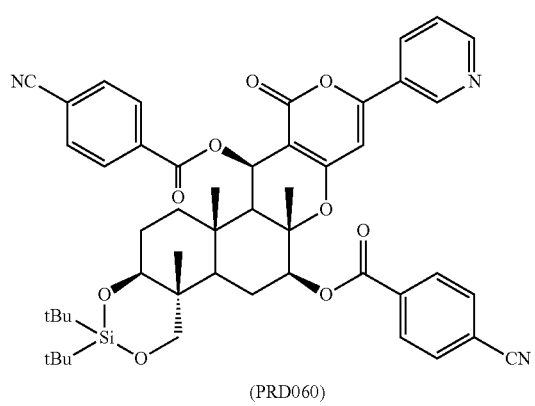

(PRD060)

In the same manner as in Example 17, PRD 059 (220 mg, 71%) and PRD 060 (17 mg, 5%) were obtained as a white foam from 1,11-O-(di-tert-butylsilylene)-1,7,11-trideacetylpyripyropene A (256 mg, 0.429 mmol).

Data for PRD059

$^1$H NMR (CDCl$_3$, 300 MHz) δ 8.97 (dd, 1H, H-2", J=0.6, 1.5 Hz), 8.67 (dd, 1H, H-6", J=1.8, 4.8 Hz), 8.22 (d, 2H, H—Ar, J=8.4 Hz), 8.09-8.05 (m, 1H, H-4"), 7.81 (d, 2H, H—Ar, J=8.4 Hz), 7.41-7.29 (m, 1H, H-5"), 6.40 (s, 1H, H-5'), 5.28-5.25 (m, 1H, H-7), 5.03 (d, 1H, H-13, J=4.2 Hz), 3.95 (dd, 1H, H-1, J=4.5, 11.4 Hz), 3.82 (d, 2H, H-11), 3.23 (br s, 1H, OH-13), 2.23-1.37 (m, 8H, H-2, 3, 5, 8, 9), 1.85 (s, 3H, Me), 1.48 (s, 3H, Me), 1.15 (s, 3H, Me), 1.10 (s, 9H, $^t$Bu), 1.04 (s, 9H, $^t$Bu).

FAB-LRMS m/z 727 (MH$^+$); FAB-HRMS (CHCl$_3$) calcd. for C$_{41}$H$_{50}$N$_2$O$_8$Si 727.3415 (MH$^+$). found 727.3428 (MH$^+$).

Data for PRD060

$^1$H NMR (CDCl$_3$, 300 MHz) δ 8.98 (dd, 1H, H-2", J=0.6, 1.5 Hz), 8.69 (dd, 1H, H-6", J=1.5, 3.1 Hz), 8.25-8.08 (m, 5H, H-4", Ar), 7.83 (d, 2H, H—Ar, J=8.4 Hz), 7.46 (d, 2H, H—Ar, J=8.4 Hz), 7.41 (dd, 1H, H-5", J=4.8, 12.9 Hz), 6.68 (d 1H, H-13, J=5.5 Hz), 6.42 (s, 1H, H-5'), 5.36 (dd, 1H, H-7, J=5.4, 11.1 Hz), 3.95 (dd, 1H, H-1, J=5.4, 9.6 Hz), 3.82 (d, 2H, H-11), 2.50-0.81 (m, 8H, H-2, 3, 5, 8, 9), 1.99 (s, 3H, Me), 1.25 (s, 3H, Me), 1.10 (s, 9H, $^t$Bu), 1.08 (s, 3H, Me), 1.03 (s, 9H, $^t$Bu).

ESI-LRMS m/z 749 (M+Na$^+$). ESI-HRMS (MeOH) calcd. for C$_{41}$H$_{50}$N$_2$NaO$_8$Si 749.3234 (M+Na$^+$). found 749.3227 (M+Na$^+$).

Example 87

Preparation of 7-O-p-cyanobenzoyl-1,11-di-(O-isobutyryl)-1,7,11-trideacetylpyripyropene A a) Preparation of 7-O-p-cyanobenzoyl-1,7,11-trideacetylpyripyropene A

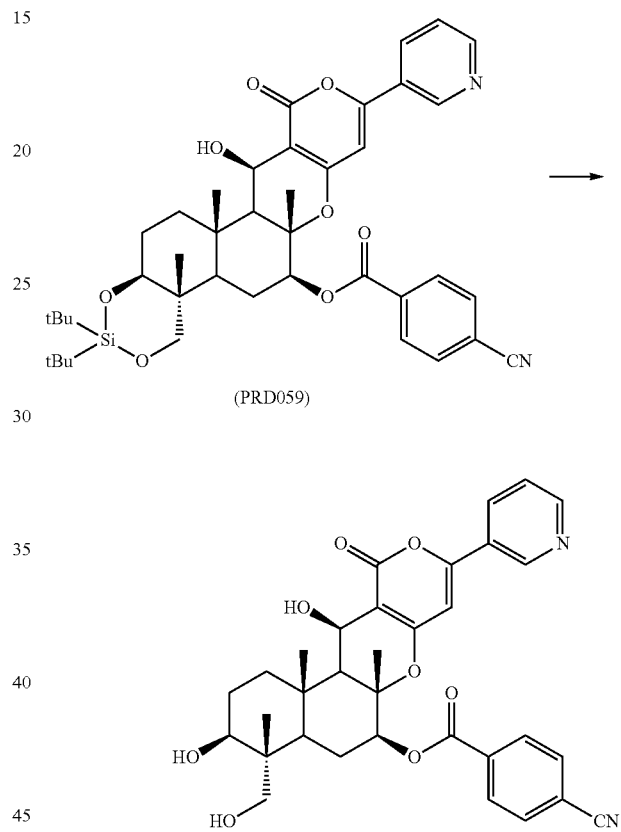

In the same manner as in Example 30, 7-O-p-cyanobenzoyl-1,7,11-trideacetylpyripyropene A (136 mg, 79%) was obtained as a white solid from PRD 059 (215 mg, 0.296 mmol).

$^1$H NMR (DMSO-d6, 300 MHz) δ 9.00 (dd, 1H, H-2", J=0.6, 2.4 Hz), 8.62 (dd, 1H, H-6", J=1.5, 4.5 Hz), 8.22-8.17 (m, 3H, H-4", Ar), 8.07-8.03 (m, 2H, H—Ar), 7.49-7.44 (m, 1H, H-5"), 6.84 (s, 1H, H-5'), 5.44 (d, 1H, OH-11, J=4.5 Hz), 5.18 (dd, 1H, H-7, J=4.8, 11.4 Hz), 4.80 (dd, 1H, H-13, J=3.3, 5.4 Hz), 4.52 (t, 1H, OH-1, J=1.5 Hz), 4.26 (d, 1H, OH-13, J=2.1 Hz), 3.46 (dd, 1H, H-11a, J=5.4, 10.8 Hz), 3.36-3.27 (m, 1H, H-1), 3.01 (dd, 1H, H-11b, J=4.5, 10.8 Hz), 2.07-1.32 (m, 8H, H-2, 3, 5, 8, 9), 1.80 (s, 3H, Me), 1.34 (s, 3H, Me), 0.58 (s, 3H, Me).

ESI-LRMS m/z 609 (M+Na$^+$). ESI-HRMS (MeOH) calcd. for C$_{33}$H$_{34}$N$_2$NaO$_8$ 609.2213 (M+Na$^+$). found 609.2221 (M+Na$^+$).

b) Preparation of 7-O-p-cyanobenzoyl-1,11-di-(O-isobutyryl)-1,7,11-trideacetylpyripyropene A (PRD 056)

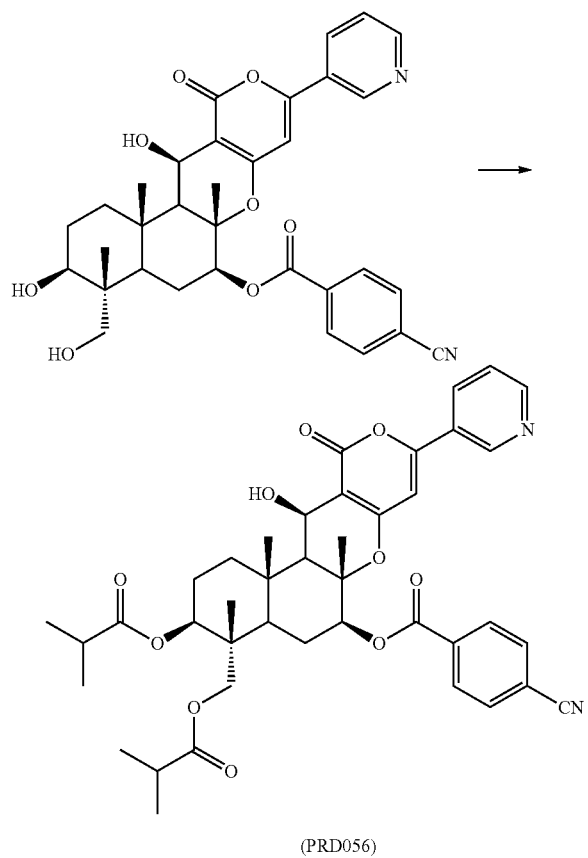

(PRD056)

In an argon atmosphere, Et$_3$N (16 μL, 113 μmol), DMAP (2.3 mg, 18.8 μmol), and isobutyric anhydride (9 μL, 56.3 μmol) were added to a solution of 7-O-p-cyanobenzoyl-1,7,11-trideacetylpyripyropene A (11 mg, 18.8 μmol) in dried DMF (0.5 mL) at 0° C. and stirred for 10 minutes at room temperature. MeOH was added to stop the reaction. EtOAc was then added to the reaction mixture, and the organic layer was washed with 1N HCl, an aqueous saturated sodium hydrogen carbonate solution, and water and dried over anhydrous sodium sulfate. The solution was filtered, and the filtrate was dried over anhydrous sodium sulfate and concentrated. The resulting residue was purified by neutral flash silica gel column chromatography (0.7×5, MeOH in CH$_2$Cl$_2$ 0-2%) to give PRD 056 (11.1 mg, 81%) as a white solid.

$^1$H NMR (CDCl$_3$, 300 MHz) δ 8.96 (dd, 1H, H-2", J=0.6, 2.1 Hz), 8.67 (dd, 1H, H-6", J=1.5, 4.5 Hz), 8.20 (d, 2H, H—Ar, J=8.1 Hz), 8.08-8.04 (m, 1H, H-4"), 7.80 (d, 2H, H—Ar, J=8.1 Hz), 7.41-7.36 (m, 1H, H-5"), 6.40 (s, 1H, H-5'), 5.25 (dd, 1H, H-7, J=5.1, 10.8 Hz), 5.05 (dd, 1H, H-13, J=1.2, 3.0 Hz), 4.83 (dd, 1H, H-1, J=4.5, 11.1 Hz), 3.75 (d, 2H, H-11, J=1.2 Hz), 3.02 (br s, 1H, OH-13), 2.61 (q, 1H, CH(Me)$_2$, J=7.2 Hz), 2.54 (q, 1H, CH(Me)$_2$, J=7.2 Hz), 2.23-1.13 (m, 8H, H-2, 3, 5, 8, 9), 1.85 (s, 3H, Me), 1.51 (s, 3H, Me), 1.26-1.14 (m, 12H, $^i$Pr×2), 0.93 (s, 3H, Me).

FAB-LRMS m/z 727 (MH$^+$); FAB-HRMS (CHCl$_3$) calcd. for C$_{41}$H$_{47}$N$_2$O$_{10}$ 727.3231 (MH$^+$). found 727.3237 (MH$^+$).

Test 1

Preparation of Source of ACAT 2 Enzyme

A partial modification of the method of Uelmen et al (J. Biol. Chem., vol. 270, pp. 26192-26201, 1995) was employed. The source of ACAT 2 enzyme used was a membrane fraction derived from mouse liver microsome. Mouse liver was homogenized in buffer solution A (50 mM Tris-HCl (pH 7.8), 1 mM ethylenediamine tetraacetate, and 1 mM phenylmethanesulfonyl fluoride) using a homogenizer of the Potter type (Tokyo-RIKO). The homogenate was centrifuged at 12000×g, and the supernatant was ultracentrifuged at 100000×g. The sediment was taken as a microsome fraction, and this fraction was adjusted to have a protein concentration of 5 mg/ml using buffer solution A.

Measurement of ACAT-Inhibiting Activity and Assessment of Specific Activity Relative to Pyripyropene A Measurement of ACAT-inhibiting activity was carried out by adding 200 μg as protein of the enzyme source, 200 mM bovine serum albumin, [1-$^{14}$C] oleoyl coenzyme A (final concentration 170 μM, 0.09 μCi), and the particular pyripyropene A derivative to be tested to buffer solution A in an amount sufficient to make a total volume of 200 μL and allowing the mixture to react for 5 minutes at 37° C. As a control, 10 μL of methanol were used in place of the pyripyropene A derivative.

Thereafter, the reaction was terminated by adding 1.2 mL of chloroform/methanol (1:2), and the lipid was recovered by the method of Bligh & Dyer (Can. J. Biochem. Physiol., vol. 37, pp, 911-917, 1959). The chloroform layer was evaporated to dryness and was used to spot a thin layer chromatography plate (silica gel plate, Merck, 0.5 mm thickness). Elution for separation was carried out using a solvent of hexane/diethyl ether/acetic acid (70:30:1, v/v). Subsequently, the amount of [$^{14}$C]cholesteryl oleate which was formed was determined by a BAS 2000 bio-image analyzer (Fuji Film), and the inhibitory activity of the test compound was calculated by the following equation by comparison with the result in the control:

% Inhibition=100−[(radioactivity when the test compound was added)−(background)]/[(radioactivity in the control)−(background)]

wherein the background is the radioactivity of a thin layer chromatography plate which was not spotted.

The concentration at which 50% inhibition of the enzyme activity was achieved (IC$_{50}$) was calculated. In addition, the specific activity relative to pyripyropene A was calculated by the following equation:

Specific activity=(IC$_{50}$ of the test compound)/(IC$_{50}$ of pyripyropene A).

The derivative of Example 23 (PRD 024) showed a specific activity which is equal to or greater than 100 with respect to inhibition of ACAT 2.

The results of inhibitory activity and specific activity are shown in Table 1.

TABLE 1

| | Inhibitory activity | Specific activity |
|---|---|---|
| PRD 001 | ** | + |
| PRD 002 | ** | +++ |
| PRD 003 | *** | +++ |
| PRD 004 | ** | +++ |
| PRD 005 | ** | +++ |
| PRD 006 | ** | ++ |
| PRD 007 | *** | ++++ |
| PRD 008 | *** | +++ |
| PRD 009 | *** | ++++ |

TABLE 1-continued

| | Inhibitory activity | Specific activity |
|---|---|---|
| PRD 010 | ** | +++ |
| PRD 011 | ** | +++ |
| PRD 012 | *** | +++ |
| PRD 013 | *** | +++ |
| PRD 014 | ** | ++ |
| PRD 015 | * | + |
| PRD 016 | ** | +++ |
| PRD 017 | ** | +++ |
| PRD 018 | ** | + |
| PRD 019 | ** | +++ |
| PRD 020 | *** | +++ |
| PRD 021 | *** | ++++ |
| PRD 022 | *** | +++ |
| PRD 023 | ** | +++ |
| PRD 024 | *** | +++++ |
| PRD 025 | *** | ++++ |
| PRD 026 | *** | ++++ |
| PRD 027 | ** | +++ |
| PRD 028 | ** | +++ |
| PRD 029 | ** | + |
| PRD 030 | ** | ++ |
| PRD 031 | * | + |
| PRD 032 | * | + |
| PRD 034 | * | + |
| PRD 035 | * | + |
| PRD 036 | ** | ++ |
| PRD 037 | * | + |
| PRD 038 | ** | ++ |
| PRD 039 | ** | +++ |
| PRD 040 | ** | +++ |
| PRD 041 | ** | + |
| PRD 042 | ** | +++ |
| PRD 043 | ** | +++ |
| PRD 044 | ** | +++ |
| PRD 045 | ** | ++ |
| PRD 046 | ** | +++ |
| PRD 047 | ** | +++ |
| PRD 048 | ** | ++ |
| PRD 049 | ** | +++ |
| PRD 050 | ** | +++ |
| PRD 051 | ** | ++ |
| PRD 052 | ** | ++ |
| PRD 053 | ** | + |
| PRD 054 | ** | + |
| PRD 055 | ** | +++ |
| PRD 056 | ** | +++ |
| PRD 057 | ** | + |
| PRD 058 | ** | +++ |
| PRD 059 | * | + |
| PRD 060 | * | + |
| PRD 061 | * | + |
| PRD 062 | * | + |
| PRD 063 | * | + |
| PRD 064 | * | + |
| PRD 065 | * | + |
| PRD 066 | * | + |
| PRD 075 | ** | ++ |
| PRD 084 | ** | +++ |
| PRD 085 | ** | + |
| PRD 087 | * | + |
| PRD 090 | * | + |
| PRD 092 | * | + |
| PRD 093 | * | + |
| PRD 095 | * | + |
| PRD 096 | * | + |
| PRD 098 | * | + |
| PRD 100 | *** | +++ |
| PRD 102 | * | + |
| PRD 103 | *** | +++ |
| PRD 104 | * | + |
| PRD 105 | *** | +++ |
| PRD 106 | * | + |
| PRD 107 | * | + |
| PRD 108 | * | + |
| PRD 109 | *** | +++ |
| PRD 110 | *** | +++ |
| PRD 111 | * | + |
| PRD 112 | *** | +++ |
| Pyripyropene A | * | 1 |

Inhibitory activity: Concentration required for 50% inhibition of ACAT 2
***: 0.01 μM > Inhibitory activity
**: 0.1 μM > Inhibitory activity > 0.01 μM
*: 1 μM > Inhibitory activity > 0.1 μM
Specific activity: (inhibitory activity of test compound)/(inhibitory activity of pyripyropene A)
+++++: specific activity > 100
++++: 100 > specific activity > 50
+++: 50 > specific activity > 10
++: 10 > specific activity > 5
+: 5 > specific activity > 1

A method for testing the ACAT 2-inhibiting activity is not limited to the above-described method, and a microsome prepared by the small intestine or liver of an animal such as a rat or monkey may be used as a source of ACAT 2 enzyme. Alternatively, cultured cells (such as Caco-2 intestinal cells, primarily cultured hepatic cells, or HepG 2 hepatic cells) or a microsome prepared from cultured cells having highly expressed ACAT 2 can be used as a source of ACAT 2 enzyme.

Test 2

Ten-week old apolipoprotein E-deficient mice (males, purchased from Jackson Laboratories) were kept under cycles of artificial light (day) for 12 hours and dark (night) for 12 hours by appropriately feeding a standard high-fat feed (D12079B, Research Diet). Before starting a test for each test compound, 100 μL of blood were collected from the caudal vein of each animal to measure the total cholesterol concentration in plasma using a commercially available kit (Determiner TC 555, Kyowa Medex). Based on the measured concentration, mice were grouped such that there was no difference between mouse groups to which the respective test compounds were administered. Pyripyropene A and its derivatives of Examples 17 (PRD 017), 63 (PRD 041), and 86 (PRD 059) were each dissolved in a 0.5% (w/v) solution of carboxymethyl cellulose in physiological saline and the resulting solutions were administered to mice at a dose of 10 mg/kg or 50 mg/kg for pyripyropene A and 1 mg/kg, 10 mg/kg, or 50 mg/kg for PRD 017, PRD 041, and PRD 056 with an amount of administration of 2.5 mL/kg. The test compound was orally administered daily at the start of the artificial light cycle of each day.

Blood was collected at the start of the artificial light cycle on day 14 of administration of the test compound to measure the total plasma cholesterol. The total plasma cholesterol before administration of the test compound (on day 0) was taken as 100%, and the percent increase in total plasma cholesterol on day 14 after administration of the test compound started was calculated.

The percent increase in total plasma cholesterol is shown in Table 2. In the control group in which only the solvent was administered with no drug, the total plasma cholesterol was increased to 212.2%, and this value was decreased to 177.3% (10 mg/kg) and 174.0% (50 mg/kg) in the group to which pyripyropene A (PPA) was administered. In contrast, this value was decreased to 161.6% (1 mg/kg), 149.7% (10 mg/kg), and 132.5% (50 mg/kg) in the group to which PRD 017 was administered, to 102.4% (1 mg/kg), 88.2% (10 mg/kg), and 101.1% (50 mg/kg) in the group to which PRD 041 was administered, and to 148.0% (1 mg/kg), 114.8% (10 mg/kg), and 86.1% (50 mg/kg) in the group to which PRD 056 was administered. Namely, PRD 017, PRD 041, and PRD 056 suppressed an increase in the total plasma cholesterol of apolipoprotein E-deficient mice by oral administration to a greater degree than did pyripyropene A.

TABLE 2

| Test compound | Dose (mg/kg) | % increase in total plasma cholesterol |
| --- | --- | --- |
| None | 0 | 212.2 |
| PPA | 10 | 177.3 |
|  | 50 | 174.0 |
| PRD 017 | 1 | 161.6 |
|  | 10 | 149.7 |
|  | 50 | 132.5 |
| PRD 041 | 1 | 102.4 |
|  | 10 | 88.2 |
|  | 50 | 101.1 |
| PRD 056 | 1 | 148.0 |
|  | 10 | 114.8 |
|  | 50 | 86.1 |

As can be seen from the above results, a compound according to the present invention has an improved ACAT 2-inhibiting activity and is useful as a therapeutic or prophylactic agent for obesity, adiposis, hyperlipidemia, hypercholesterolemia, disorder of lipid metabolism, and arteriosclerosis, as well as obesity-derived hyperlipidemia, hypercholesterolemia, disorder of lipid metabolism, arteriosclerosis, and hypertension.

INDUSTRIAL APPLICABILITY

A pyripyropene derivative according to the present invention or its pharmacologically acceptable salt has an improved ACAT 2-inhibiting activity. A pharmaceutical composition containing a compound according to the present invention, its pharmacologically acceptable salt, its pharmacologically acceptable ester, or other pharmacologically acceptable derivative thereof as an active ingredient is useful as a prophylactic or therapeutic agent (drug) for diseases relating to arteriosclerosis. Accordingly, a compound according to the present invention can be widely used in prevention and treatment of arteriosclerosis of animals including human beings.

The invention claimed is:
1. A compound represented by the following formula (II):

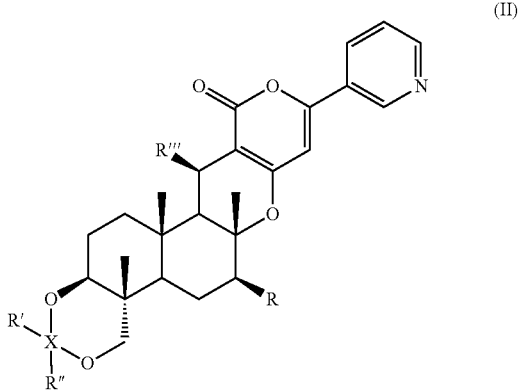

wherein R represents a benzoyloxy having a cyano substitutent or a halo substitutent at the 2-, 3-, or 4-position, R''' represents hydroxyl, one of R' and R'' represents a hydrogen atom, the other R' and R'' represents an aromatic ring, and X represents a carbon atom, or a pharmaceutically acceptable salt thereof.

2. An ACAT 2 inhibitor composition comprising as an active ingredient a compound selected from the compound group of claim 1 or a pharmaceutically acceptable salt thereof.

* * * * *

UNITED STATES PATENT AND TRADEMARK OFFICE
CERTIFICATE OF CORRECTION

PATENT NO.         : 8,519,128 B2
APPLICATION NO.    : 12/810545
DATED              : August 27, 2013
INVENTOR(S)        : Hiroshi Tomoda et al.

Page 1 of 1

It is certified that error appears in the above-identified patent and that said Letters Patent is hereby corrected as shown below:

On the Title Page, Column 2, item (56) OTHER PUBLICATIONS, Line 19, delete "Nenkai" and insert -- Nankai --

In the Claims

Column 104, Lines 26-27, Claim 1, delete "substitutent" and insert -- substituent --

Column 104, Line 27, Claim 1, delete "substitutent" and insert -- substituent --

Signed and Sealed this
Second Day of June, 2015

Michelle K. Lee
*Director of the United States Patent and Trademark Office*